US006429291B1

(12) United States Patent
Turley et al.

(10) Patent No.: US 6,429,291 B1
(45) Date of Patent: Aug. 6, 2002

(54) HYALURONAN RECEPTOR PROTEIN

(76) Inventors: Eva Ann Turley, #5 - 375 Wellington Crescent, Winnipeg, Manitoba (CA), L2M 0A1; Shuwen Zhang, 143 Branson Crescent, Winnipeg, Manitoba (CA), R2P 9N9; Jocelyn Entwistle, 380 Linden Wood Drive East, Winnipeg, Manitoba (CA), R3P 2H1

( * ) Notice: Subject to any disclaimer, the term of this patent is extended or adjusted under 35 U.S.C. 154(b) by 0 days.

(21) Appl. No.: 08/477,831

(22) Filed: Jun. 7, 1995

(30) Foreign Application Priority Data

Oct. 14, 1994 (GB) ............................................... 9420740

(51) Int. Cl.[7] ............................................. C07K 14/705
(52) U.S. Cl. ......................... 530/350; 530/300; 530/324
(58) Field of Search ................................. 530/350, 308, 530/300, 324; 514/2, 12; 435/69.1

(56) References Cited

FOREIGN PATENT DOCUMENTS

WO        WO 93/21312        * 10/1993

OTHER PUBLICATIONS

Aruffo, A. et al. (1990) "CD44 Is the Principal Cell Surface Receptor for Hyaluronate." *Cell,* 61, pp. 1303–1313.
Boudreau, N. et al. (1991) "Fibronectin, Hyaluronan and a Hyaluronan Binding Protein Contribute to Increased Ductus Arteriosus Smooth Muscle Cell Migration." *Devel. Biol.,* 143, pp. 235–247.
Dalchau, R. et al. (1980) "Monoclonal Antibody To A Human Brain–Granulocyte–T Lymphocyte Antigen Probably Homologous To The W 3/13 Antigen Of The Rat." *Eur. J. Immunol.,* 10, pp. 745–749.
Forsberg, et al. (1991) "Characterization and Purification of the Hyaluronan–Receptor on Liver Endothelial Cells." *Biochimica et Biophysica Acta,* 1078, pp. 12–18.
Hardwick, C., Hoare, K., Owens, R., Hohn, H.P., Hook, M., Moore, D., Cripps, V., Austen, L., Nance D.M. and Turley, E.A. (1992) "Molecular Cloning of a Novel Hyaluronan Receptor That Mediates Tumor Cell Motility." *J. Cell Biol.,* 117, pp. 1343–1350.
Iozzo, R.V. (1985) "Biology of Disease." *Lab. Invest.,* 53, pp. 373–396.
Raja, P.H., McGary, C.T. and Weigel, P.H. (1988) "Affinity and Distribution of Surface and Intracellular Hyaluronic Acid Receptors in Isolated Rat Liver Endothelial Cells." *J. Biol. Chem.,* 263, pp. 16661–16668.
Stemenkovic, I., Aruffo, A., Amist, M. and Seed, B. (1991) "The Hematopoietic and Epithelial Forms of CD44 are Distinct Polypeptides with Different Adhesion Potentials for Hyaluronate–Bearing Cells." *EMBO J.,* 10, pp. 343–348.
Toole, B.P. et al. (1984) "Hyaluronate–Cell Interactions." *The Role of Extracellular Matrix in Development,* pp. 43–66.
Turley, E.A. (1992) "Hyaluronan and Cell Locomotion." *Cancer Met. Rev.,* 11, pp. 21–30.
Turley, E.A. (1984) "Proteoglycans and Cell Adhesion: Their Putative Role during Tumorigenesis." *Cancer Met. Rev.,* 3, pp. 325–339.
Yang, B., Zhang, L. and Turley, E.A. (1993) "Identification of Two Hyaluronan–binding Domains in the Hyaluronan Receptor RHAMM." *J. Biol. Chem.,* 268, pp. 8617–8623.

* cited by examiner

*Primary Examiner*—Elizabeth Kemmerer
(74) *Attorney, Agent, or Firm*—Fish & Neave; Margaret A. Pierri; Shawn-Marie Mayrand

(57) ABSTRACT

The present invention relates to a novel hyaluronan receptor protein involved in cell locomotion or motility and in cell proliferation and transformation and to DNA sequences encoding this protein. The protein is designated Receptor for Hyaluronic Acid Mediated Motility or RHAMM.

3 Claims, 70 Drawing Sheets

FIG. 1A

```
aagtatctgatacctcacctagcctaaataattatattatgatgtGGAGAATAGATATCTGAGTTCTTATGTTTATTCTAGTTTCTGAAGATGGTACCAAAAGAAT 1  ATG AGA GCT CTA AGC CCT CTG GAA TTG ATG AAG AGA AAT AAG CTC AGA CAG AAG CTC ACG GAC CTC AAG TCT AAG GGA AAA    20
     M   R   A   L   S   P   L   E   L   M   K   R   N   K   L   R   Q   K   L   T   D   L   K   S   K   G   K 21  ttgtgcagAGT ATG ATG GTC AAA CAG GAA GGC ATG CAG GAA CTC CAG ATG GAG CTC AAG ACT CAA GTG GAA AAA TGC AAA       45
             S   M   M   V   K   Q   E   G   M   Q   E   L   Q   M   E   L   K   T   Q   V   E   K   C   K     intron 1...tgtg 47  ATA GTC CAG CTC CAG GGA AAC CTcatgtggcacaa...intron 2...cttttaatacagC TGT GCA TCT GAT CAA GTG TCT CTT GAG AAC ATT   64
     I   V   Q   L   Q   G   N   L                                       C   A   S   D   Q   V   S   L   E   N   I 65  GTA GAT ATT GCC CAG TTA GAA GAT CTT AAA GAG ATT TTG AAG CAG TCT CTT GAG GAG AAC ATT       92
     V   D   I   A   Q   L   E   D   L   K   E   I   L   K   Q   S   L   E   E   N   I        Gtactgtgctgt...intron 3...ag 93  ACA TTT TCT AAG GGA ATA GAA GAC CTG ACT AGA GAA AGA ACA GAA ATG CAG ATC CTT ACA GAG AGG CTG       112
     T   F   S   K   G   I   E   D   L   T   R   E   R   T   E   M   Q   I   L   T   E   R   L 113  tctctcttacag AC AAC CTT GTC AGC AAG GAT GCT AGT CAG TCA CTT TTC CAA AAG GAG CAG AGT GAA AGG CTT AAGgtagctccacc   137
                 D   N   L   V   S   K   D   A   S   Q   S   L   F   Q   K   E   Q   S   E   R   L   K 138  GCT CTG GAA AGG CAA CAA AAG CTG CAA GAA TTG CAA AGC CTA TCA TCT CAG AAC ACG CTG AGA GTG ACT TCT GAG AAG CTT    162
     A   L   E   R   Q   Q   K   L   Q   E   L   Q   S   L   S   S   Q   N   T   L   R   V   T   S   E   R   L 163  ...intron 4...tgtctgaatgcag GAA CTC CTG AGC CTC GCC TTA AAG GAG TTG CAG AAC CAG GAG GAG CAG AGT GAA AGG CTT GTT   183
                              E   L   L   S   L   A   L   K   E   L   Q   N   Q   E   E   Q   S   E   R   L   V 184  AAC GTC TTT AAA GAA GAG CTA GAA AAG GAA TCA TCT GCT GAT GCG CGG ACC CTT AGA GCC ATC TTG ATT GCA CAA CAA GAG    211
     N   V   F   K   E   E   L   E   K   E   S   S   A   D   A   R   T   L   R   A   I   L   I   A   Q   Q   E 212  AAA CAG CTG GAA GAG GAA CGG AAG GTT GAA CTG GAA AAA CAT ATT GCT GAA AGT GTG CAA AGT GCA ACA GCA CAG AGG CTG    234
     K   Q   L   E   E   E   R   K   V   E   L   E   K   H   I   A   E   S   V   Q   S   A   T   A   Q   R   L 235  5...tctcgtcttagg AAA GAG GTT GAA CTG AGG AGA CTG CGT AAG GTC CAG ATC CTG CAA AAC ATG ACT GAA AGG CTT AAG   257
                    K   E   V   E   L   R   R   L   R   K   V   Q   I   L   Q   N   M   T   E   R   L   K 258  AAT GAC ACA GCA CAG AGT CTG CGG GAC TTG GAA AGT GAA TAC AAT CAT CAG TTG AAT AGT CAA ACA GCA CAG AGG CTG    285
     N   D   T   A   Q   S   L   R   D   L   E   S   E   Y   N   H   Q   L   N   S   Q   T   A   Q   R   L 286  AGG GAC GTC ACT GCT CAG GAA AGT GAG TAC AAC TAC AAG GAC GTC AGG GAC GTC ACA GCA CAG AGT CTG CGG GAC GTC    313
     R   D   V   T   A   Q   E   S   E   Y   N   Y   K   D   V   R   D   V   T   A   Q   S   L   R   D   V 314  GAA AGT GAG CAG CAA GAG AAG TAC AAC CAG AGG CTG AGT CAG AGG CTG CGG GAC GTC AGG GAC GTC AAG TAC    341
     E   S   E   Q   Q   E   K   Y   N   Q   R   L   S   Q   R   L   R   D   V   R   D   V   K   Y
```

```
 925 GTC ACT GCT CAG TTG GAA AGT GAG CAA GAG AAG TAC AAT GAC ACA GCA CAG AGT CTG AGG GAC GTC ACT GCT CAG TTG GAA AGT
      V   T   A   Q   L   E   S   E   Q   E   K   Y   N   D   T   A   Q   S   L   R   D   V   T   A   Q   L   E   S

1009 GTG CAA GAG TAC AAG GAT CTT AAA CTG GAG AAT TTG ACT CTA CAA GAA TAT CAG AGT CTG GAA TTG CAG GAT GTC ACT GCT CAG
      V   Q   E   Y   K   D   L   K   L   E   N   L   T   L   Q   E   Y   Q   S   L   E   L   Q   D   V   T   A   Q

1093 GAA ATA GAA GAT CTT AAA CTG GAG AAT TTG ACT CTA CAA GAA TAT CAG AGT CTG ATG GCT ATG GTT CAA TTG CAG GAT GTT CAA
      E   I   E   D   L   K   L   E   N   L   T   L   Q   E   Y   Q   S   L   M   A   M   V   Q   L   Q   D   V   Q

1177 CAG ATA TTG ACA GCT GAG AGC ACA GAA TAT GCA AGG ATG GTT CAA TTG CAG GAT TTG AAA AAT CAA CTC AGA CAA TCA ACC TTA AAA GAA GAA
      Q   I   L   T   A   E   S   T   E   Y   A   R   M   V   Q   L   Q   D   L   K   N   Q   L   R   Q   S   T   L   K   E   E

1261 GAA ATT AAA TCT TCA TTT CTT GAG AAA ATA ACT CAA GAA AAT ACT GAT AAA ATA GTA ACC AGA CAA CTC TTA ACA GAA ATT AAT AAA GAT GAA GAC TTT AGG
      E   I   K   S   S   F   L   E   K   I   T   Q   E   N   T   D   K   I   V   T   R   Q   L   L   T   E   I   N   K   D   E   D   F   R

1345 AAG CAG CTG GAA GAG AAA GAA CTA TAT GAT GAA CTA AAA ACT AAA AAA CCT TTT CAG CAA CAG ACA CTC TTA ACA GAG GTG TCA AAA CTC CGA TCT CAG CTT AAA
      K   Q   L   E   E   K   E   L   Y   D   E   L   K   T   K   K   P   F   Q   Q   Q   T   L   L   T   E   V   S   K   L   R   S   Q   L   K

1429 CTC CTA TAT GAT GAA CTA AAT GAG CAG CAG ACT CAG GAG CAG CTA AAA GAT GAT TCC TAT GCA GAG GTG TCA AAA CTC CGA TCT CAG CTT AAA
      L   L   Y   D   E   L   N   E   Q   Q   T   Q   E   Q   L   K   D   D   S   Y   A   E   V   S   K   L   R   S   Q   L   K

1513 AAT GAA CAT GGT GCA ACT CAG GAG CAG CTA AAA GAT GAT TCC TAT GCA GAG GTG TCA AAA CTC CGA TCT CAG CTT AAA
      N   E   H   G   A   T   Q   E   Q   L   K   D   D   S   Y   A   E   V   S   K   L   R   S   Q   L   K

1597 AAA ATC AAA AAT GAG CTC AGA CTT AAA GAT GAA AAT TTA AAA GAT CTG AAA AAC CTA CAG CTT GTT AAA
      K   I   K   N   E   L   R   L   K   D   E   N   L   K   D   L   K   N   L   Q   L   V   K

1681 AGG AAA CAA CAA AAT GAG CTC AGA CTT CAG GGA GAA TTA GAT AAA GAA GGA AAT ATT AAT TGG AAG GCA TTG TTG
      R   K   Q   Q   N   E   L   R   L   Q   G   E   L   D   K   E   G   N   I   N   W   K   A   L   L

1765 CAT GCA TCT AAG GAG AAT TTT ACT CCA TTA AAA GAA GGC AAC CCA AAC TGC TGA
      H   A   S   K   E   N   F   T   P   L   K   E   G   N   P   N   C   C   *
``` kb 4.2 –

1.7 –

```
RHAMM IA   AGGCCTTAGGTCCAGGAAGGAGAAAAACCATCTTCTTCTGCGAGTAATGCTTCACTGGTAA ......
RHAMM IB   ......

AACGGGCTTACTGAATTAACCAGAGCCAACGAGCTAC TAA AAGGCTAAAGGA  TCTGAAGATGGTCACCAAAAGAAT
        ......GGCAGAATAGATATCTGAGTTCTTATGTTTATTG TAG TTT

ATG AGA GCT CTA AGC CTG GAA TTG ATG AAA CTC AGA AAT AAG AGA GAG ACA AAG ATG AGG
 M   R   A   L   S   L   E   L   M   K   L   R   N   K   R   E   T   K   M   R
```

FIG. 11A

```
GAGCTCAATAAACCCTCATAAAAGGGATAGATAGATCCACAGGCAGCAAAAGGAGACTGTGCCAC
ACTAGGCCTAACTTGAGCTTATAAAACCTCAAATCCCACCTCCACAGTGACACACTTCTTCCAAC
AAGGCCACCCCTAATAATGCCACTCCCTGTGGGCCAAGTATCAAACACACAAGTCTCTGAGGGCC
ATTACTATCAAACCTCCACCGTATCAAAACTATTAAAGATACGCTTTATAAATATTTTCTCCAGT
TCTATAAGTGGTCTCGTTATCTAGTCACTTCTTTTGCTGTCTAGAATGTTGATGTAGTTGCAATC
ATCTGTTTTTGCTTTTTCTGTCTGCTTTGAGGATTTGTACACACATACACAAGCACACGTGCCAA
ATCCAGGGTTCCTGAAGCATTACCCCTGAGTGTGTGCTAGCAGTACTATTAAGTGTTAAATACAT
AGTTAATTTTGAGTTGACTTTGGAAGCTGATGGGTGAAAGAGACCTACTGTCATTTTTCCCTCAT
GAGGATTCAGTGTTAATGGCACAGTCTGGGAGGATTCTCCTGTCACTGGTGCTTGTGCTATGGCG
TGTTTGTTGCTTCTTGGCTCTACACTGTTAATATATCCAGTTGTCTTTTTTCACTCTAACACAGT
GCTCTCACTTCAGTAGCTTTGTAGTATATTAAATCATATAGTGGAATCACTCTTGTATTGCTTTT
TCCTCAAGATGTCTTTTGCTTATATGGTTTTTCATTATTTCATATTTTTTAAAAATTTATAGATT
TCTTTCTTGCTTTGTGAAGAATGTCCTTGATGTCTAGTTAGAGGTCTCATTGAATTTATAAGCTA
CTTTGATAATTTTACCATCTATAAATATGAAGAATTACTTATATCCTCTTAAAAATTTGTATATC
GATATTTTTTTTTTAACAAAATCTCAATCATTTGATTTTTTACCAGTAAAGACTCAGGAGCCAGA
AGCTAGGGTCAAAATTTGATAGTTCAGAGAGACAGAGAAAGCACCCATCACCCAGCTTATCTTAT
TCCTCAGCCAATGTCCCAAAAAGGAAGTTCTCCTCTACACCATCATAAACCTCCCTTCAATCAGC
ATGTCCCTCCCTTCTATTTCCTGTGTGTGTGCCTCTCCATCCTCCTGACTTCCTCTTACTTTCTC
TATGGTTTTTCCTGTGTTCACTCCCTGTCAACCTTGTTGCTTGCCCTTAACCTCTGGTTGACTTT
ATTTAATTCCTATTTATACGTAAACAGAAAAGCCCTCAGGTTAAAGGTGTGTGTTAGGGCTGAGT
CATGCCTAAACTAAAACAAGTTTTTCTAGTAAAGGGTTCACAGTGTGATCAAAATATCCTGCAAC
ACTTTATCATTTTTATTGTAGAAAACGGATCCCCGCGATTGTGGTTTGAATGGCACATGCCCCAT
ACCAGTCCTGTTTTGAACCTGTTCCTAGTTGGTCATGTTGGCAGGCTGTGGGACCCTTGAGGAGG
TTGTGGGGCACAGCTAGAGGAAGTAGGCCTATGAAGGATAGGTCCTTGGAAACTTTAAAAGAAAA
CAAGAAATTGCAAGGGGTCAAACAAAAGAGCCAGATATAATGCTGCACCATGTGTGAGGTGAAGG
CAGGAGCATCAGGGGGTCACCGTGATTCTGGCTACCAAGGAAGCTGGCTTTGTCTAGGCTCTGTT
TTGTTCATTTCTGCTCTGACTTTTACACTTCCAAAAATTAAGACTGCAGCAAACTTGCCGGGTGT
GTGGCGCACGTCTTTAATCCCAGCACTTGGGAGGCAGAGGCAGGCGGATTTCTGAGTTTGAGGCC
GCCTGGTCTACAGAGTGAGTTCCAGGACAGCCAGGGCTACACAGAGAAACCCTGTCTCGGAAAAC
CAAAAACAACAAAAAAAAAAAGAACTGCAGCAAGTTGTTAACCCTTTTGTGTTTGCTTTTCTCTG
AAAGCTAGAGCTACTAAGACTTTCCTCAATATTTGGTCAGTCCTTCCCTTAACCCCTTATGTGCC
AGTTAAAACCTAATCATTCTCAAACGCAGGAGTGTGTTACCTTTCACGCTTTCATGCCTCCGCAA
TTAAGAACAGGGAAGGTCTTAAGATCGCTCTTCTAACATCATTACATTGAGATAGTTGTCTAAAA
CTATCTCAACTGAAACCTTGGGACAGGAAGGTACGATTAATGTCCAATTATTACTTTGTTAGAAA
ATTACTGAGCTATAAGTTCCATATAACATAATACCATGTAGTGATCATATGTTTGTAGTTGAATG
ACATCATAGCCATATACACTTGTGAAAACTGAAAACATTTGCACCCCTGGGAATGCTGCCTCTGC
CTCTGTAACCTTGTAATGCTCCCCATCCCCACAGTTCTCTGTCTTTTAAATTGCTATAGGAAAAG
GTTATCACTACTCAGGGTACAAGACTTGTTCATCATAATTCATATCATATATACTATAATTTTTC
ATTTTCATTGCTTAGCTTAAATTCACTATATGAGTATTTCTCTATAAATTAACCATATGAGCATT
ACTTGAGTTGGTTTTGGTCTTTTGACTACTGAATATGACAGCTATGAACATGCTGTATGTCTTTG
TGAATATGTATCTTTTATACCTCTTTAGTAAGCATATAGGAGTGGGAGTCTCAAACCAGAATCAT
GCAAATTGGACATAAGGGCTGGGAGATAAATCACTGAACACAGTACCTGCTGAAAAAACCAGGGG
GCCTGAGTTTAGATCCCCAGTTCACGCATAGAGTACTGGGCTTGGGGATCTGTCTATTCTTCGAC
TCTAGGTGAGCAGAGACAGGTAGATGTTGGGTGTCTACTGGATAGCAAGTGAAGACCAAAACAAT
GAGCTCTACACTTGAGAGAGGCCCTGTCTCTAAAATAAAGTAAGTGCAACAGAAGAGGCACCTGA
TCTTGGCTTCTGGCCTCCATAAGCACACACATGCTTGTGTCTACCTGCACACACATAAACATATCAC
ACACAGCACTTACACACACATCACATGCACACGCAGCTGTGCTGCTTTATAACTACAGCAAGGAA
TGCTCTTTAGAGTTGTTCTGCATTCATACTGTTTGATATTGCTGGTCTGTTCCCCCTTTCTAATG
GCATAAAATGCTGATTTGTCATTTGTCTTTGTTCTTCCTGTTTGAAACAAGGTCCTGGGTCTCAA
GTAGCCCAGGAGGTCTTCATAGTCTCCATCCTCCTGCCTTCAGCCTCCCACATTGCTAGGATTTA
CAGACCTGAACCATACAACCTGGCAATAATCTATTACTTTAATTTCTTGTATGTGGATTTGTAGG
CGTCACATATCTTCTATTCTGAAATGTCTATTTAAAAATCTTACTCAATTCCTCAAACTAGATCA
TCCTGAAGAGCCTAAACCATGGAAGTAAGTTGAATACCATATAGCCTGGAGCAAAAGCCTCTTGC
```

FIG. 11B

```
ACACAAAATGTGCCTTGGACTGGGGAAGGAACTAGGAAAGCTGCAAAATAAGATGATTCTGATTT
ATAAAGTGGTTCTTGTCGTGCAGATCAGGGTTGGGAAGCTTATGTTAATAAATCCAAGCTCCTGG
GTCGCTAGGAGTTGTTCATCTGAAAGAACCTCACATTAAGTTGTAAGAGTTTGACCTCTAGTGTT
ACCTTACATGACATAATAATACTATCTATTAAGTACTATACATGGTTATTAATAAGTGAACCATC
TATATTTACTCTTTCTTTTTTCTTTTTCAGTGTTTCAATAGAGAAAGAAAAGATCGATGAAAAAT
GTGAAACAGAAAAACTCTTAGAATACATCCAAGAAATTAGGTAATATAAATAGTAGCTTTAAAAT
TAACTTCTGGGCTGGAGAGATGGCTCAGCAGTTAAGAGCACCGGCTGCTCTTGGAGAAGATCCAT
TGCATTTCTTAGCAGGGACATGGTGGCTCACAACCATCTGTAACTCCGTGCCCGAGAGAATTTAT
CCAGTGCCACCTTCTTCATCAGTGGTGGTCTCAAACATACATGTGGGCAAACACGCATACACATT
GAATAAACAAATAATTGAAATGAAATTTAGTAAAGAGAAGAACCTTACTGGTTTGCGATATGAC
TTTGTTGGTAGAGCATATGCCTTGCATATGGGAAGGCCTGGAATGAGTATCAGGTTTTTTGCACA
GAGAAAACAAAAGCACCTTATTTGTTGAACATGTTTTCCTGTACCTTAAGAGAAATTTTCTTC
AATATACTTTTAATACAG
```

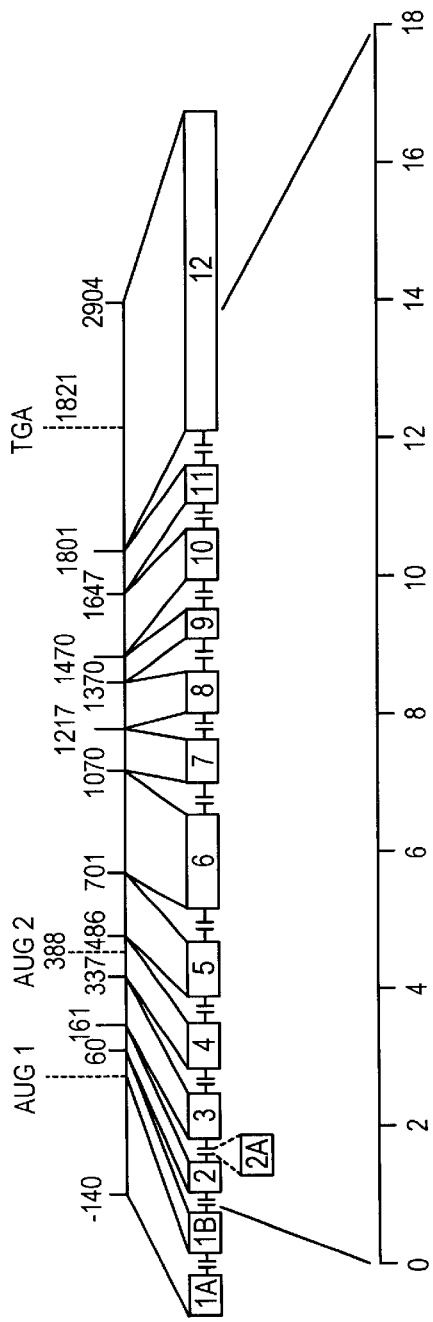
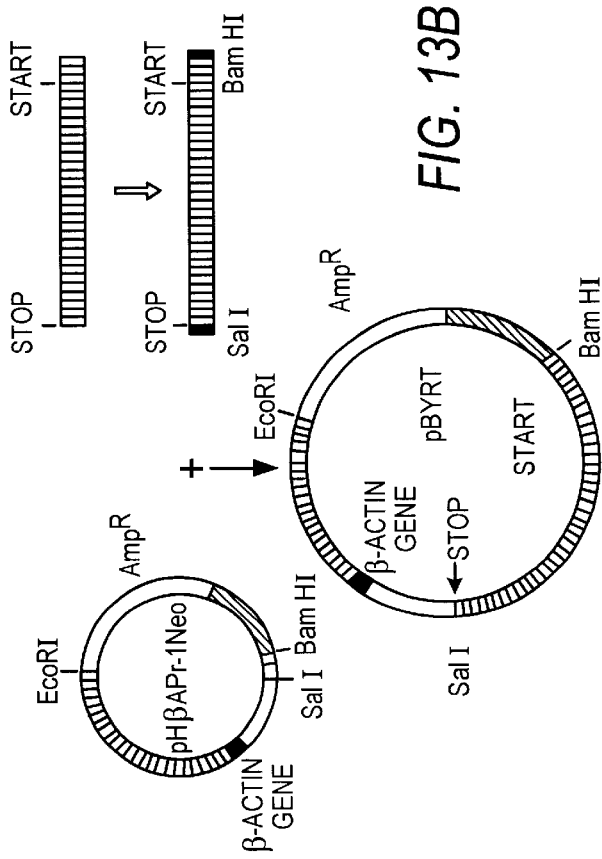
FIG. 13A
FIG. 13B 1    2
66►  ─  ━
kDa
FIG. 13C
RHAMM ►
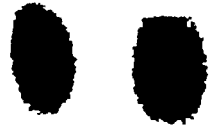
GAPDH ►
FIG. 13D

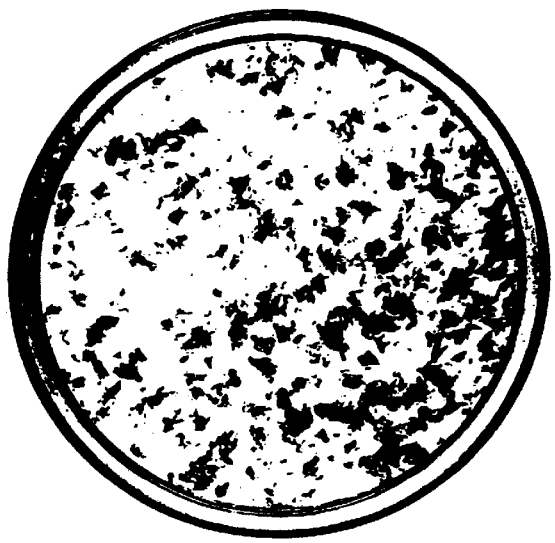 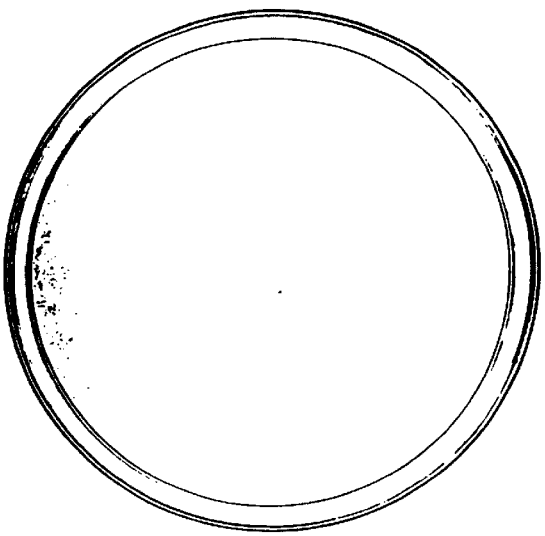
FIG. 16

To insert a Hind III site, $E^{412}$ was altered to $L^{412}$

83 →
KDa p21▶

FIG. 21

 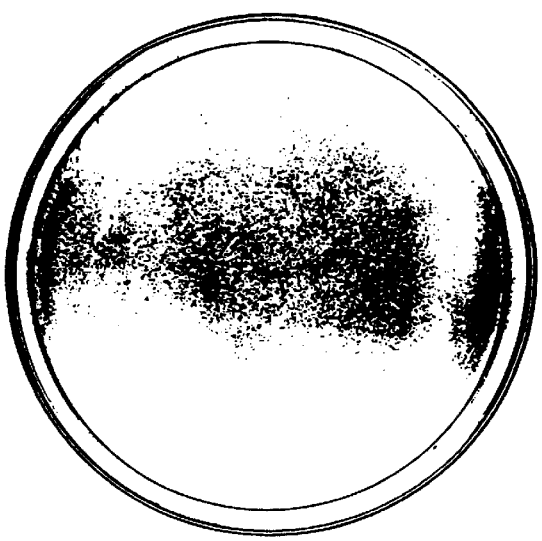
FIG. 24

FIG. 25A
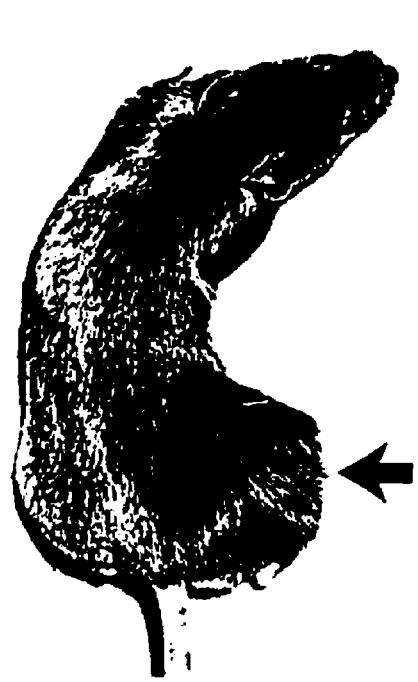
FIG. 25B
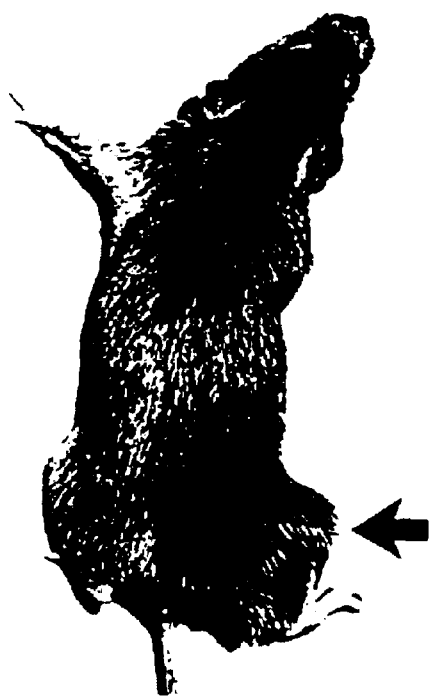
FIG. 25C
FIG. 25D FIG. 32A
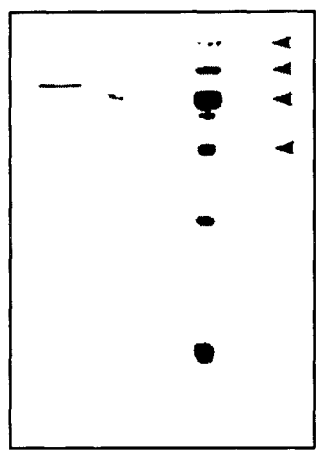
FIG. 32B
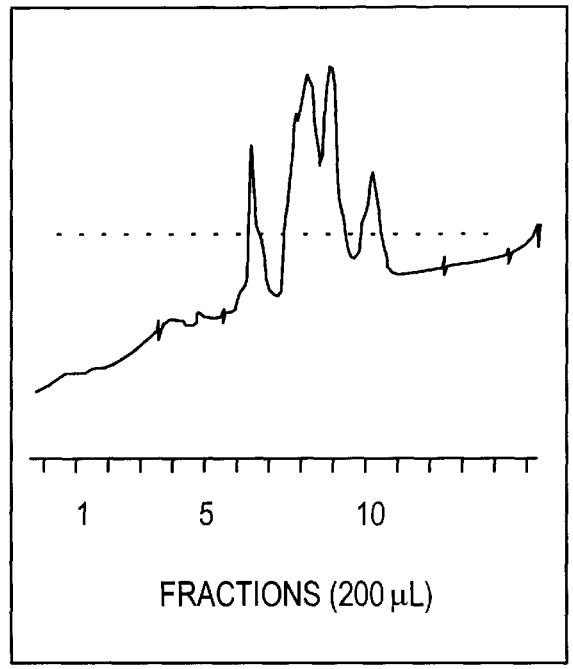
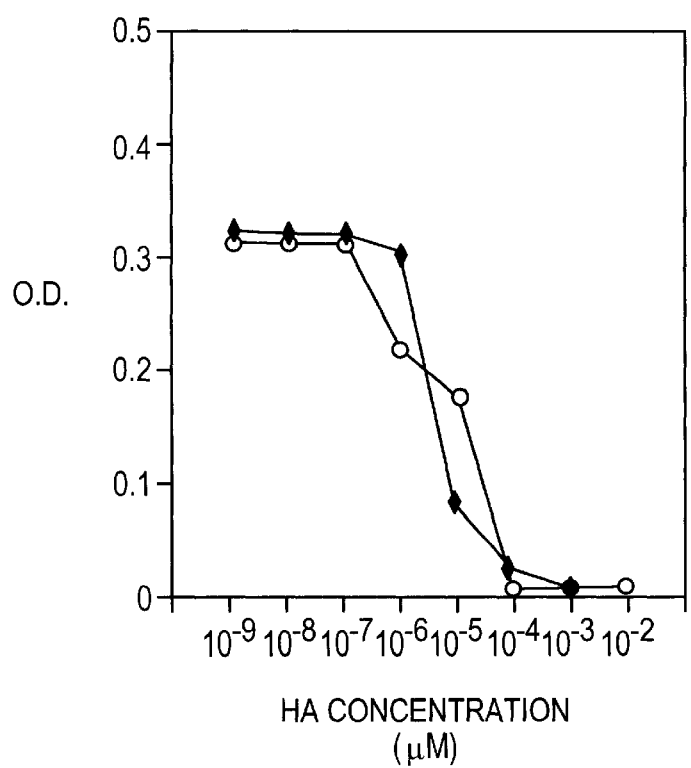
FIG. 32C

 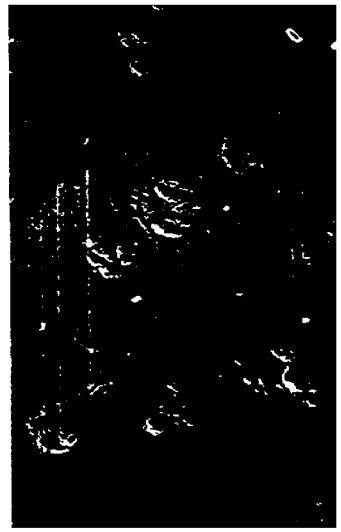 
FIG. 39A  FIG. 39B  FIG. 39C
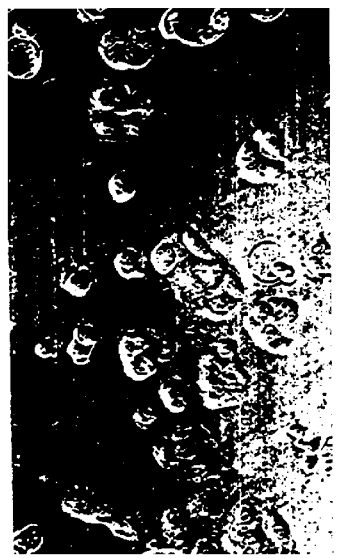  
FIG. 39D  FIG. 39E  FIG. 39F

```
HUMAN   IEDLKLENSSLQEEAAKAGKNAEDVQHQILATESSNQEYVRMLLDLQTKSALKETEIKEI
        IEDLKLEN +LQE+ A  A K+ EDVQ QIL  ES+NQEY RM+ DLQ +S LKE EIKEI
MOUSE   IEDLKLENLTLQEKVAMAEKSVEDVQQQILTAESTNQEYARMVQDLQNRSTLKEEEIKEI

HUMAN   TVSFLQKITDQQNQLKQQEEDFRNRLEDEEGRTAEKENPTPELTMEINKWRLLYDELYEK
        T SFL+KITD +NQL+QQ+EDFR +LE++  RTAEKEN    ELTMEINKWRLLY+ELYEK
MOUSE   TSSFLEKITDLKNQLRQQDEDFRKQLEEKGKRTAEKENVMTELTMEINKWRLLYEELYEK

HUMAN   TKPFQQQLDAFEVEKQALLDEHGAAQEQLNKIRDSYAKLLGHQNLKQKIRHVVKLKDENS
        TKPFQQQLDAFE EKQALL+EHGA QEQLNKIRDSYA+LLGHQNLKQKI+HVVKLKDENS
MOUSE   TKPFQQQLDAFEAEKQALLNEHGATQEELNKIRDSYAQLLGHQNLKQKIKHVVKLKDENS

HUMAN   QLK 183
        QLK
MOUSE   QLK 419
```

FIG. 42C

SEQUENCE LISTING (1) GENERAL INFORMATION:

(iii) NUMBER OF SEQUENCES: 60

(2) INFORMATION FOR SEQ ID NO:1:

(i) SEQUENCE CHARACTERISTICS:
      (A) LENGTH: 1821 base pairs
      (B) TYPE: nucleic acid
      (C) STRANDEDNESS: single
      (D) TOPOLOGY: linear (ii) MOLECULE TYPE: cDNA
        (A) DESCRIPTION: /desc = "RHAMM I cDNA (coding region)"

(xi) SEQUENCE DESCRIPTION: SEQ ID NO:1:

```
ATGAGAGCTC TAAGCCTGGA ATTGATGAAA CTCAGAAATA GAGAGAGAC AAAGATGAGG      60

AGTATGATGG TCAAACAGGA AGGCATGGAG CTGAAGCTGC AGGCCACTCA GAAGGACCTC    120

ACGGAGTCTA AGGGAAAAAT AGTCCAGCTG GAGGGAAAGC TCTGTGCATC TGATCAAGTG    180

GAAAAATGCA AAGTAGATAT TGCCCAGTTA GAAGAAGATT TGAAAGAGAA GGATCGTGAG    240

ATTTTAAGTC TTAAGCAGTC TCTTGAGGAA ACATTACAT TTTCTAAGCA AATAGAAGAC    300

CTGACTGTTA AATGCCAGCT ACTTGAAACA GAAAGAGACA ACCTTGTCAG CAAGGATAGA    360

GAAAGGGCTG AAACTCTCAG TGCTGAGATG CAGATCCTGA CAGAGAGGCT GGCTCTGGAA    420

AGGCAAGAAT ATGAAAAGCT GCAACAAAAA GAATTGCAAA GCCAGTCACT TCTGCAGCAA    480

GAGAAGGAAC TGTCTGCTCG TCTGCAGCAG CAGCTCTGCT CTTTCCAAGA GGAAATGACT    540

TCTGAGAAGA ACGTCTTTAA AGAAGAGCTA AAGCTCGCCC TGGCTGAGTT GGATGCGGTC    600

CAGCAGAAGG AGGAGCAGAG TGAAAGGCTG GTTAAACAGC TGGAAGAGGA AAGGAAGTCA    660

ACTGCAGAAC AACTGACGCG GCTGGACAAC CTGCTGAGAG AGAAAGAAGT TGAACTGGAG    720

AAACATATTG CTGCTCACGC CCAAGCCATC TTGATTGCAC AAGAGAAGTA TAATGACACA    780

GCACAGAGTC TGAGGGACGT CACTGCTCAG TTGGAAAGTG TGCAAGAGAA GTATAATGAC    840

ACAGCACAGA GTCTGAGGGA CGTCACTGCT CAGTTGGAAA GTGAGCAAGA GAAGTACAAT    900

GACACAGCAC AGAGTCTGAG GGACGTCACT GCTCAGTTGG AAAGTGAGCA AGAGAAGTAC    960

AATGACACAG CACAGAGTCT GAGGGACGTC ACTGCTCAGT TGGAAAGTGT GCAAGAGAAG   1020

TACAATGACA CAGCACAGAG TCTGAGGGAC GTCACTGCTC AGTTGGAAAG CTATAAGTCA   1080

TCAACACTTA AGAAATAGA AGATCTTAAA CTGGAGAATT TGACTCTACA AGAAAAAGTA   1140

GCTATGGCTG AAAAAAGTGT AGAAGATGTT CAACAGCAGA TATTGACAGC TGAGAGCACA   1200

AATCAAGAAT ATGCAAGGAT GGTTCAAGAT TTGCAGAACA GATCAACCTT AAAAGAAGAA   1260

GAAATTAAAG AAATCACATC TTCATTTCTT GAGAAAATAA CTGATTTGAA AAATCAACTC   1320

AGACAACAAG ATGAAGACTT TAGGAAGCAG CTGGAAGAGA AAGGAAAAAG AACAGCAGAG   1380

AAAGAAAATG TAATGACAGA ATTAACCATG GAAATTAATA AATGGCGTCT CCTATATGAT   1440

GAACTATATG AAAAAACTAA ACCTTTTCAG CAACAACTGG ATGCCTTTGA AGCCGAGAAA   1500

CAGGCATTGT TGAATGAACA TGGTGCAACT CAGGAGCAGC TAAATAAAAT CAGAGACTCC   1560

TATGCACAGC TACTTGGTCA CCAGAACCTA AGCAAAAAA TCAAACATGT TGTGAAATTG   1620

AAAGATGAAA ATAGCCAACT CAAATCGGAG GTGTCAAAAC TCCGATCTCA GCTTGTTAAA   1680

AGGAAACAAA ATGAGCTCAG ACTTCAGGGA GAATTAGATA AAGCTCTGGG CATCAGACAC   1740

TTTGACCCTT CCAAGGCTTT TGTCATGCA TCTAAGGAGA ATTTTACTCC ATTAAAAGAA   1800

GGCAACCCAA ACTGCTGCTG A                                              1821
```

(2) INFORMATION FOR SEQ ID NO:2:

(i) SEQUENCE CHARACTERISTICS:
        (A) LENGTH: 606 amino acids
        (B) TYPE: amino acid
        (C) STRANDEDNESS: single
        (D) TOPOLOGY: linear (ii) MOLECULE TYPE: protein
        (A) DESCRIPTION: /desc = "RHAMM I protein"

(xi) SEQUENCE DESCRIPTION: SEQ ID NO:2:

```
Met Arg Ala Leu Ser Leu Glu Leu Met Lys Leu Arg Asn Lys Arg Glu
1               5                   10                  15

Thr Lys Met Arg Ser Met Met Val Lys Gln Glu Gly Met Glu Leu Lys
            20                  25                  30

Leu Gln Ala Thr Gln Lys Asp Leu Thr Glu Ser Lys Gly Lys Ile Val
        35                  40                  45

Gln Leu Glu Gly Lys Leu Cys Ala Ser Asp Gln Val Glu Lys Cys Lys
    50                  55                  60

Val Asp Ile Ala Gln Leu Glu Asp Leu Lys Glu Lys Asp Arg Glu
65                  70                  75                  80

Ile Leu Ser Leu Lys Gln Ser Leu Glu Glu Asn Ile Thr Phe Ser Lys
                85                  90                  95

Gln Ile Glu Asp Leu Thr Val Lys Cys Gln Leu Leu Glu Thr Glu Arg
            100                 105                 110

Asp Asn Leu Val Ser Lys Asp Arg Glu Arg Ala Glu Thr Leu Ser Ala
        115                 120                 125

Glu Met Gln Ile Leu Thr Glu Arg Leu Ala Leu Glu Arg Gln Glu Tyr
    130                 135                 140

Glu Lys Leu Gln Gln Lys Glu Leu Gln Ser Gln Ser Leu Leu Gln Gln
145                 150                 155                 160

Glu Lys Glu Leu Ser Ala Arg Leu Gln Gln Gln Leu Cys Ser Phe Gln
                165                 170                 175

Glu Glu Met Thr Ser Glu Lys Asn Val Phe Lys Glu Glu Leu Lys Leu
            180                 185                 190

Ala Leu Ala Glu Leu Asp Ala Val Gln Gln Lys Glu Glu Gln Ser Glu
        195                 200                 205

Arg Leu Val Lys Gln Leu Glu Glu Arg Lys Ser Thr Ala Glu Gln
    210                 215                 220

Leu Thr Arg Leu Asp Asn Leu Leu Arg Glu Lys Glu Val Glu Leu Glu
225                 230                 235                 240

Lys His Ile Ala Ala His Ala Gln Ala Ile Leu Ile Ala Gln Glu Lys
                245                 250                 255

Tyr Asn Asp Thr Ala Gln Ser Leu Arg Asp Val Thr Ala Gln Leu Glu
            260                 265                 270

Ser Val Gln Glu Lys Tyr Asn Asp Thr Ala Gln Ser Leu Arg Asp Val
        275                 280                 285

Thr Ala Gln Leu Glu Ser Glu Gln Glu Lys Tyr Asn Asp Thr Ala Gln
    290                 295                 300

Ser Leu Arg Asp Val Thr Ala Gln Leu Glu Ser Glu Gln Glu Lys Tyr
305                 310                 315                 320

Asn Asp Thr Ala Gln Ser Leu Arg Asp Val Thr Ala Gln Leu Glu Ser
                325                 330                 335

Val Gln Glu Lys Tyr Asn Asp Thr Ala Gln Ser Leu Arg Asp Val Thr
            340                 345                 350

Ala Gln Leu Glu Ser Tyr Lys Ser Ser Thr Leu Lys Glu Ile Glu Asp
        355                 360                 365

Leu Lys Leu Glu Asn Leu Thr Leu Gln Glu Lys Val Ala Met Ala Glu
    370                 375                 380

Lys Ser Val Glu Asp Val Gln Gln Ile Leu Thr Ala Glu Ser Thr
385                 390                 395                 400
```

```
Asn Gln Glu Tyr Ala Arg Met Val Gln Asp Leu Gln Asn Arg Ser Thr
            405                 410                 415

Leu Lys Glu Glu Glu Ile Lys Glu Ile Thr Ser Ser Phe Leu Glu Lys
            420                 425                 430

Ile Thr Asp Leu Lys Asn Gln Leu Arg Gln Gln Asp Glu Asp Phe Arg
            435                 440                 445

Lys Gln Leu Glu Glu Lys Gly Lys Arg Thr Ala Glu Lys Glu Asn Val
            450                 455                 460

Met Thr Glu Leu Thr Met Glu Ile Asn Lys Trp Arg Leu Leu Tyr Asp
465                 470                 475                 480

Glu Leu Tyr Glu Lys Thr Lys Pro Phe Gln Gln Gln Leu Asp Ala Phe
            485                 490                 495

Glu Ala Glu Lys Gln Ala Leu Leu Asn Glu His Gly Ala Thr Gln Glu
            500                 505                 510

Gln Leu Asn Lys Ile Arg Asp Ser Tyr Ala Gln Leu Leu Gly His Gln
            515                 520                 525

Asn Leu Lys Gln Lys Ile Lys His Val Val Lys Leu Lys Asp Glu Asn
            530                 535                 540

Ser Gln Leu Lys Ser Glu Val Ser Lys Leu Arg Ser Gln Leu Val Lys
545                 550                 555                 560

Arg Lys Gln Asn Glu Leu Arg Leu Gln Gly Glu Leu Asp Lys Ala Leu
            565                 570                 575

Gly Ile Arg His Phe Asp Pro Ser Lys Ala Phe Cys His Ala Ser Lys
            580                 585                 590

Glu Asn Phe Thr Pro Leu Lys Glu Gly Asn Pro Asn Cys Cys
            595                 600                 605

(2) INFORMATION FOR SEQ ID NO:3:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: cDNA
         (A) DESCRIPTION: /desc = "Exon 2A"

(xi) SEQUENCE DESCRIPTION: SEQ ID NO:3:

TGTTTCAATA GAGAAAGAAA AGATCGATGA AAAATGTGAA ACAGAAAAAC TCTTAGAATA     60

CATCCAAGAA ATTAG                                                     75

(2) INFORMATION FOR SEQ ID NO:4:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide
            (a) DESCRIPTION: /desc = "Exon 2A"

(xi) SEQUENCE DESCRIPTION: SEQ ID NO:4:

Val Ser Ile Glu Lys Glu Lys Ile Asp Glu Lys Cys Glu Thr Glu Lys
1               5                   10                  15

Leu Leu Glu Tyr Ile Gln Glu Ile Ser
            20                  25
```

(2) INFORMATION FOR SEQ ID NO:5:

(i) SEQUENCE CHARACTERISTICS:
        (A) LENGTH: 140 base pairs
        (B) TYPE: nucleic acid
        (C) STRANDEDNESS: single
        (D) TOPOLOGY: linear (ii) MOLECULE TYPE: cDNA
        (A) DESCRIPTION: /desc = "RHAMM IA 5' UTS"

(xi) SEQUENCE DESCRIPTION: SEQ ID NO:5:

```
AGGCCTTAGG TCCAGGAAGG AGGAAAAACC ATCTTCTTCT CTGCGAGTAA TGCTTCACTG     60

GTAAAAACGG CTTACTGAAT TAACCAGAGC CAACGAGCTA CTAAAAGGCT AAAGGATCTG    120

AAGATGGTCA CCAAAAGAAT                                                140
```

(2) INFORMATION FOR SEQ ID NO:6:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: cDNA
        (A) DESCRIPTION: /desc = "RHAMM IB 5' UTS"

(xi) SEQUENCE DESCRIPTION: SEQ ID NO:6:

```
GGCAGAATAG ATATCTGAGT TCTTATGTTT ATTGTAGTTT TCTGAAGATG GTCACCAAAA     60

GAAT                                                                  64
```

(2) INFORMATION FOR SEQ ID NO:7:

(i) SEQUENCE CHARACTERISTICS:
        (A) LENGTH: 4243 base pairs
        (B) TYPE: nucleic acid
        (C) STRANDEDNESS: single
        (D) TOPOLOGY: linear (ii) MOLECULE TYPE: DNA (genomic)
        (A) DESCRIPTION: /desc = "Intron 2"

(xi) SEQUENCE DESCRIPTION: SEQ ID NO:7:

```
GAGCTCAATA AACCCTCATA AAAGGGATAG ATAGATCCAC AGGCAGCAAA AGGAGACTGT     60

GCCACACTAG GCCTAACTTG AGCTTATAAA ACCTCAAATC CCACCTCCAC AGTGACACAC    120

TTCTTCCAAC AAGGCCACCC CTAATAATGC CACTCCCTGT GGGCCAAGTA TCAAACACAC    180

AAGTCTCTGA GGGCCATTAC TATCAAACCT CCACCGTATC AAAACTATTA AGATACGCT     240

TTATAAATAT TTTCTCCAGT TCTATAAGTG GTCTCGTTAT CTAGTCACTT CTTTTGCTGT    300

CTAGAATGTT GATGTAGTTG CAATCATCTG TTTTTGCTTT TTCTGTCTGC TTTGAGGATT    360

TGTACACACA TACACAAGCA CACGTGCCAA ATCCAGGGTT CCTGAAGCAT TACCCCTGAG    420

TGTGTGCTAG CAGTACTATT AAGTGTTAAA TACATAGTTA ATTTTGAGTT GACTTTGGAA    480

GCTGATGGGT GAAAGAGACC TACTGTCATT TTTCCCTCAT GAGGATTCAG TGTTAATGGC    540

ACAGTCTGGG AGGATTCTCC TGTCACTGGT GCTTGTGCTA TGGCGTGTTT GTTGCTTCTT    600

GGCTCTACAC TGTTAATATA TCCAGTTGTC TTTTTTCACT CTAACACAGT GCTCTCACTT    660

CAGTAGCTTT GTAGTATATT AAATCATATA GTGGAATCAC TCTTGTATTG CTTTTTCCTC    720

AAGATGTCTT TTGCTTATAT GGTTTTTCAT TATTTCATAT TTTTTTAAAA ATTATAGATT    780

TCTTTCTTGC TTTGTGAAGA ATGTCCTTGA TGTCTAGTTA GAGGTCTCAT TGAATTTATA    840
```

```
AGCTACTTTG ATAATTTTAC CATCTATAAA TATGAAGAAT TACTTATATC CTCTTAAAAA    900
TTTGTATATC GATATTTTTT TTTTAACAAA ATCTCAATCA TTTGATTTTT TACCAGTAAA    960
GACTCAGGAG CCAGAAGCTA GGGTCAAAAT TTGATAGTTC AGAGAGACAG AGAAAGCACC   1020
CATCACCCAG CTTATCTTAT TCCTCAGCCA ATGTCCCAAA AAGGAAGTTC TCCTCTACAC   1080
CATCATAAAC CTCCCTTCAA TCAGCATGTC CCTCCCTTCT ATTTCCTGTG TGTGTGCCTC   1140
TCCATCCTCC TGACTTCCTC TTACTTTCTC TATGGTTTTT CCTGTGTTCA CTCCCTGTCA   1200
ACCTTGTTGC TTGCCCTTAA CCTCTGGTTG ACTTTATTTA ATTCCTATTT ATACGTAAAC   1260
AGAAAAGCCC TCAGGTTAAA GGTGTGTGTT AGGGCTGAGT CATGCCTAAA CTAAAACAAG   1320
TTTTTCTAGT AAAGGGTTCA CAGTGTGATC AAAATATCCT GCAACACTTT ATCATTTTTA   1380
TTGTAGAAAA CGGATCCCCG CGATTGTGGT TTGAATGGCA CATGCCCCAT ACCAGTCCTG   1440
TTTTGAACCT GTTCCTAGTT GGTCATGTTG GCAGGCTGTG GGACCCTTGA GGAGGTTGTG   1500
GGGCACAGCT AGAGGAAGTA GGCCTATGAA GGATAGGTCC TTGGAAACTT TAAAAGAAAA   1560
CAAGAAATTG CAAGGGGTCA AACAAAAGAG CCAGATATAA TGCTGCACCA TGTGTGAGGT   1620
GAAGGCAGGA GCATCAGGGG GTCACCGTGA TTCTGGCTAC CAAGGAAGCT GGCTTTGTCT   1680
AGGCTCTGTT TTGTTCATTT CTGCTCTGAC TTTTACACTT CCAAAAATTA AGACTGCAGC   1740
AAACTTGCCG GGTGTGTGGC GCACGTCTTT AATCCCAGCA CTTGGGAGGC AGAGGCAGGC   1800
GGATTTCTGA GTTTGAGGCC GCCTGGTCTA CAGAGTGAGT TCCAGGACAG CCAGGGCTAC   1860
ACAGAGAAAC CCTGTCTCGG AAAACCAAAA ACAACAAAAA AAAAAGAAC TGCAGCAAGT   1920
TGTTAACCCT TTTGTGTTTG CTTTTCTCTG AAAGCTAGAG CTACTAAGAC TTTCCTCAAT   1980
ATTTGGTCAG TCCTTCCCTT AACCCCTTAT GTGCCAGTTA AAACCTAATC ATTCTCAAAC   2040
GCAGGAGTGT GTTACCTTTC ACGCTTTCAT GCCTCCGCAA TTAAGAACAG GAAGGTCTT   2100
AAGATCGCTC TTCTAACATC ATTACATTGA GATAGTTGTC TAAAACTATC TCAACTGAAA   2160
CCTTGGGACA GGAAGGTACG ATTAATGTCC AATTATTACT TTGTTAGAAA ATTACTGAGC   2220
TATAAGTTCC ATATAACATA ATACCATGTA GTGATCATAT GTTTGTAGTT GAATGACATC   2280
ATAGCCATAT ACACTTGTGA AAACTGAAAA CATTTGCACC CCTGGGAATG CTGCCTCTGC   2340
CTCTGTAACC TTGTAATGCT CCCCATCCCC ACAGTTCTCT GTCTTTTAAA TTGCTATAGG   2400
AAAAGGTTAT CACTACTCAG GGTACAAGAC TTGTTCATCA TAATTCATAT CATATATACT   2460
ATAATTTTTC ATTTTCATTG CTTAGCTTAA ATTCACTATA TGAGTATTTC TCTATAAATT   2520
AACCATATGA GCATTACTTG AGTTGGTTTT GGTCTTTTGA CTACTGAATA TGACAGCTAT   2580
GAACATGCTG TATGTCTTTG TGAATATGTA TCTTTTATAC CTCTTTAGTA AGCATATAGG   2640
AGTGGGAGTC TCAAACCAGA ATCATGCAAA TTGGACATAA GGGCTGGGAG ATAAATCACT   2700
GAACACAGTA CCTGCTGAAA AAACCAGGGG GCCTGAGTTT AGATCCCCAG TTCACGCATA   2760
GAGTACTGGG CTTGGGGATC TGTCTATTCT TCGACTCTAG GTGAGCAGAG ACAGGTAGAT   2820
GTTGGGTGTC TACTGGATAG CAAGTGAAGA CCAAAACAAT GAGCTCTACA CTTGAGAGAG   2880
GCCCTGTCTC TAAAATAAAG TAAGTGCAAC AGAAGAGGCA CCTGATCTTG GCTTCTGGCC   2940
TCCATAAGCA CACACATGCT TGTGTCTACC TGCACACATA AACATATCAC ACACAGCACT   3000
TACACACACA TCACATGCAC ACGCAGCTGT GCTGCTTTAT AACTACAGCA AGGAATGCTC   3060
TTTAGAGTTG TTCTGCATTC ATACTGTTTG ATATTGCTGG TCTGTTCCCC CTTTCTAATG   3120
GCATAAAATG CTGATTTGTC ATTTGTCTTT GTTCTTCCTG TTTGAAACAA GGTCCTGGGT   3180
CTCAAGTAGC CCAGGAGGTC TTCATAGTCT CCATCCTCCT GCCTTCAGCC TCCCACATTG   3240
```

-continued

```
CTAGGATTTA CAGACCTGAA CCATACAACC TGGCAATAAT CTATTACTTT AATTTCTTGT      3300

ATGTGGATTT GTAGGCGTCA CATATCTTCT ATTCTGAAAT GTCTATTTAA AAATCTTACT      3360

CAATTCCTCA AACTAGATCA TCCTGAAGAG CCTAAACCAT GGAAGTAAGT TGAATACCAT      3420

ATAGCCTGGA GCAAAAGCCT CTTGCACACA AAATGTGCCT TGGACTGGGG AAGGAACTAG      3480

GAAAGCTGCA AATAAGATG ATTCTGATTT ATAAAGTGGT TCTTGTCGTG CAGATCAGGG       3540

TTGGGAAGCT TATGTTAATA AATCCAAGCT CCTGGGTCGC TAGGAGTTGT TCATCTGAAA      3600

GAACCTCACA TTAAGTTGTA AGAGTTTGAC CTCTAGTGTT ACCTTACATG ACATAATAAT      3660

ACTATCTATT AAGTACTATA CATGGTTATT AATAAGTGAA CCATCTATAT TTACTCTTTC      3720

TTTTTTCTTT TTCAGTGTTT CAATAGAGAA AGAAAAGATC GATGAAAAAT GTGAAACAGA     3780

AAAACTCTTA GAATACATCC AAGAAATTAG GTAATATAAA TAGTAGCTTT AAAATTAACT      3840

TCTGGGCTGG AGAGATGGCT CAGCAGTTAA GAGCACCGGC TGCTCTTGGA AGAGATCCAT      3900

TGCATTTCTT AGCAGGGACA TGGTGGCTCA CAACCATCTG TAACTCCGTG CCCGAGAGAA      3960

TTTATCCAGT GCCACCTTCT TCATCAGTGG TGGTCTCAAA CATACATGTG GGCAAACACG      4020

CATACACATT GAATAAACAA ATAATTGAAA TGAAAATTTA GTAAAGAGAA GAACCTTACT      4080

GGTTTGCGAT ATGACTTTGT TGGTAGAGCA TATGCCTTGC ATATGGGAAG GCCTGGAATG      4140

AGTATCAGGT TTTTTGCACA GAGAAAACAA AAGCACCTTA TTTTGTTGAA CATGTTTTTC      4200

CTGTACCTTA AGAGAAATTT TCTTCAATAT ACTTTTAATA CAG                       4243

(2) INFORMATION FOR SEQ ID NO:8:

(i) SEQUENCE CHARACTERISTICS:
          (A) LENGTH: 1961 base pairs
          (B) TYPE: nucleic acid
          (C) STRANDEDNESS: single
          (D) TOPOLOGY: linear (ii) MOLECULE TYPE: cDNA
          (A) DESCRIPTION: /desc = "RHAMM IA"

(xi) SEQUENCE DESCRIPTION: SEQ ID NO:8:

AGGCCTTAGG TCCAGGAAGG AGGAAAAACC ATCTTCTTCT CTGCGAGTAA TGCTTCACTG        60

GTAAAAACGG CTTACTGAAT TAACCAGAGC CAACGAGCTA CTAAAAGGCT AAAGGATCTG      120

AAGATGGTCA CCAAAAGAAT ATGAGAGCTC TAAGCCTGGA ATTGATGAAA CTCAGAAATA      180

AGAGAGAGAC AAAGATGAGG AGTATGATGG TCAAACAGGA AGGCATGGAG CTGAAGCTGC      240

AGGCCACTCA GAAGGACCTC ACGGAGTCTA AGGGAAAAAT AGTCCAGCTG GAGGGAAAGC      300

TCTGTGCATC TGATCAAGTG GAAAAATGCA AAGTAGATAT TGCCCAGTTA GAAGAAGATT      360

TGAAAGAGAA GGATCGTGAG ATTTTAAGTC TTAAGCAGTC TCTTGAGGAA ACATTACAT       420

TTTCTAAGCA AATAGAAGAC CTGACTGTTA AATGCCAGCT ACTTGAAACA GAAAGAGACA      480

ACCTTGTCAG CAAGGATAGA GAAAGGGCTG AAACTCTCAG TGCTGAGATG CAGATCCTGA      540

CAGAGAGGCT GGCTCTGGAA AGGCAAGAAT ATGAAAAGCT GCAACAAAAA GAATTGCAAA      600

GCCAGTCACT TCTGCAGCAA GAGAAGGAAC TGTCTGCTCG TCTGCAGCAG CAGCTCTGCT      660

CTTTCCAAGA GGAAATGACT TCTGAGAAGA ACGTCTTTAA AGAAGAGCTA AAGCTCGCCC      720

TGGCTGAGTT GGATGCGGTC CAGCAGAAGG AGGAGCAGAG TGAAAGGCTG GTTAAACAGC      780

TGGAAGAGGA AAGGAAGTCA ACTGCAGAAC AACTGACGCG GCTGGACAAC CTGCTGAGAG      840

AGAAAGAAGT TGAACTGGAG AAACATATTG CTGCTCACGC CCAAGCCATC TTGATTGCAC      900
```

```
AAGAGAAGTA TAATGACACA GCACAGAGTC TGAGGGACGT CACTGCTCAG TTGGAAAGTG      960

TGCAAGAGAA GTATAATGAC ACAGCACAGA GTCTGAGGGA CGTCACTGCT CAGTTGGAAA     1020

GTGAGCAAGA GAAGTACAAT GACACAGCAC AGAGTCTGAG GGACGTCACT GCTCAGTTGG     1080

AAAGTGAGCA AGAGAAGTAC AATGACACAG CACAGAGTCT GAGGGACGTC ACTGCTCAGT     1140

TGGAAAGTGT GCAAGAGAAG TACAATGACA CAGCACAGAG TCTGAGGGAC GTCACTGCTC     1200

AGTTGGAAAG CTATAAGTCA TCAACACTTA AGAAATAGA AGATCTTAAA CTGGAGAATT      1260

TGACTCTACA AGAAAAGTA GCTATGGCTG AAAAAAGTGT AGAAGATGTT CAACAGCAGA      1320

TATTGACAGC TGAGAGCACA AATCAAGAAT ATGCAAGGAT GGTTCAAGAT TTGCAGAACA     1380

GATCAACCTT AAAAGAAGAA GAAATTAAAG AAATCACATC TTCATTTCTT GAGAAAATAA     1440

CTGATTTGAA AAATCAACTC AGACAACAAG ATGAAGACTT TAGGAAGCAG CTGGAAGAGA     1500

AAGGAAAAAG AACAGCAGAG AAAGAAAATG TAATGACAGA ATTAACCATG GAAATTAATA     1560

AATGGCGTCT CCTATATGAT GAACTATATG AAAAAACTAA ACCTTTTCAG CAACAACTGG     1620

ATGCCTTTGA AGCCGAGAAA CAGGCATTGT TGAATGAACA TGGTGCAACT CAGGAGCAGC     1680

TAAATAAAAT CAGAGACTCC TATGCACAGC TACTTGGTCA CCAGAACCTA AAGCAAAAAA     1740

TCAAACATGT TGTGAAATTG AAAGATGAAA ATAGCCAACT CAAATCGGAG GTGTCAAAAC     1800

TCCGATCTCA GCTTGTTAAA AGGAAACAAA ATGAGCTCAG ACTTCAGGGA GAATTAGATA     1860

AAGCTCTGGG CATCAGACAC TTTGACCCTT CCAAGGCTTT TTGTCATGCA TCTAAGGAGA     1920

ATTTTACTCC ATTAAAAGAA GGCAACCCAA ACTGCTGCTG A                         1961

(2) INFORMATION FOR SEQ ID NO:9:

(i) SEQUENCE CHARACTERISTICS:
        (A) LENGTH: 1885 base pairs
        (B) TYPE: nucleic acid
        (C) STRANDEDNESS: single
        (D) TOPOLOGY: linear (ii) MOLECULE TYPE: cDNA
         (A) DESCRIPTION: /desc = "RHAMM IB"

(xi) SEQUENCE DESCRIPTION: SEQ ID NO:9:

GGCAGAATAG ATATCTGAGT TCTTATGTTT ATTGTAGTTT TCTGAAGATG GTCACCAAAA       60

GAATATGAGA GCTCTAAGCC TGGAATTGAT GAAACTCAGA AATAAGAGAG AGACAAAGAT      120

GAGGAGTATG ATGGTCAAAC AGGAAGGCAT GGAGCTGAAG CTGCAGGCCA CTCAGAAGGA      180

CCTCACGGAG TCTAAGGGAA AAATAGTCCA GCTGGAGGGA AAGCTCTGTG CATCTGATCA      240

AGTGAAAAA TGCAAAGTAG ATATTGCCCA GTTAGAAGAA GATTTGAAAG AGAAGGATCG       300

TGAGATTTTA AGTCTTAAGC AGTCTCTTGA GGAAAACATT ACATTTTCTA AGCAAATAGA      360

AGACCTGACT GTTAAAATGCC AGCTACTTGA AACAGAAAGA GACAACCTTG TCAGCAAGGA    420

TAGAGAAAGG GCTGAAACTC TCAGTGCTGA GATGCAGATC CTGACAGAGA GGCTGGCTCT      480

GGAAAGGCAA GAATATGAAA AGCTGCAACA AAAAGAATTG CAAAGCCAGT CACTTCTGCA     540

GCAAGAGAAG GAACTGTCTG CTCGTCTGCA GCAGCAGCTC TGCTCTTTCC AAGAGGAAAT     600

GACTTCTGAG AAGAACGTCT TTAAAGAAGA GCTAAAGCTC GCCCTGGCTG AGTTGGATGC     660

GGTCCAGCAG AAGGAGGAGC AGAGTGAAAG GCTGGTTAAA CAGCTGGAAG AGGAAAGGAA     720

GTCAACTGCA GAACAACTGA CGCGGCTGGA CAACCTGCTG AGAGAAAG AAGTTGAACT      780

GGAGAAACAT ATTGCTGCTC ACGCCCAAGC CATCTTGATT GCACAAGAGA AGTATAATGA     840

CACAGCACAG AGTCTGAGGG ACGTCACTGC TCAGTTGGAA AGTGTGCAAG AGAAGTATAA     900
```

-continued

```
TGACACAGCA CAGAGTCTGA GGGACGTCAC TGCTCAGTTG GAAAGTGAGC AAGAGAAGTA    960

CAATGACACA GCACAGAGTC TGAGGGACGT CACTGCTCAG TTGGAAAGTG AGCAAGAGAA   1020

GTACAATGAC ACAGCACAGA GTCTGAGGGA CGTCACTGCT CAGTTGGAAA GTGTGCAAGA   1080

GAAGTACAAT GACACAGCAC AGAGTCTGAG GGACGTCACT GCTCAGTTGG AAAGCTATAA   1140

GTCATCAACA CTTAAAGAAA TAGAAGATCT TAAACTGGAG AATTTGACTC TACAAGAAAA   1200

AGTAGCTATG GCTGAAAAAA GTGTAGAAGA TGTTCAACAG CAGATATTGA CAGCTGAGAG   1260

CACAAATCAA GAATATGCAA GGATGGTTCA AGATTTGCAG AACAGATCAA CCTTAAAAGA   1320

AGAAGAAATT AAAGAAATCA CATCTTCATT TCTTGAGAAA ATAACTGATT TGAAAAATCA   1380

ACTCAGACAA CAAGATGAAG ACTTTAGGAA GCAGCTGGAA GAGAAAGGAA AAAGAACAGC   1440

AGAGAAAGAA AATGTAATGA CAGAATTAAC CATGGAAATT AATAAATGGC GTCTCCTATA   1500

TGATGAACTA TATGAAAAAA CTAAACCTTT TCAGCAACAA CTGGATGCCT TTGAAGCCGA   1560

GAAACAGGCA TTGTTGAATG AACATGGTGC AACTCAGGAG CAGCTAAATA AAATCAGAGA   1620

CTCCTATGCA CAGCTACTTG GTCACCAGAA CCTAAAGCAA AAAATCAAAC ATGTTGTGAA   1680

ATTGAAAGAT GAAAATAGCC AACTCAAATC GGAGGTGTCA AAACTCCGAT CTCAGCTTGT   1740

TAAAAGGAAA CAAAATGAGC TCAGACTTCA GGGAGAATTA GATAAAGCTC TGGGCATCAG   1800

ACACTTTGAC CCTTCCAAGG CTTTTTGTCA TGCATCTAAG GAGAATTTTA CTCCATTAAA   1860

AGAAGGCAAC CCAAACTGCT GCTGA                                        1885
```

(2) INFORMATION FOR SEQ ID NO:10:

(i) SEQUENCE CHARACTERISTICS:
            (A) LENGTH: 1896 base pairs
            (B) TYPE: nucleic acid
            (C) STRANDEDNESS: single
            (D) TOPOLOGY: linear (ii) MOLECULE TYPE: cDNA
            (A) DESCRIPTION:/desc = "RHAMM I-2a"

(xi) SEQUENCE DESCRIPTION: SEQ ID NO:10:

```
ATGAGAGCTC TAAGCCTGGA ATTGATGAAA CTCAGAAATA AGAGAGAGAC AAAGATGAGG     60

AGTATGATGG TCAAACAGGA AGGCATGGAG CTGAAGCTGC AGGCCACTCA GAAGGACCTC    120

ACGGAGTCTA AGGGAAAAAT AGTCCAGCTG GAGGGAAAGC TTGTTTCAAT AGAGAAAGAA    180

AAGATCGATG AAAAATGTGA AACAGAAAAA CTCTTAGAAT ACATCCAAGA AATTAGCTGT    240

GCATCTGATC AAGTGGAAAA ATGCAAAGTA GATATTGCCC AGTTAGAAGA AGATTTGAAA    300

GAGAAGGATC GTGAGATTTT AAGTCTTAAG CAGTCTCTTG AGGAAAACAT TACATTTTCT    360

AAGCAAATAG AAGACCTGAC TGTTAAATGC CAGCTACTTG AAACAGAAAG AGACAACCTT    420

GTCAGCAAGG ATAGAGAAAG GGCTGAAACT CTCAGTGCTG AGATGCAGAT CCTGACAGAG    480

AGGCTGGCTC TGGAAAGGCA AGAATATGAA AAGCTGCAAC AAAAAGAATT GCAAAGCCAG    540

TCACTTCTGC AGCAAGAGAA GGAACTGTCT GCTCGTCTGC AGCAGCAGCT CTGCTCTTTC    600

CAAGAGGAAA TGACTTCTGA AGAACGTCTT TTAAAGAAG AGCTAAAGCT CGCCCTGGCT    660

GAGTTGGATG CGGTCCAGCA GAAGGAGGAG CAGAGTGAAA GGCTGGTTAA CAGCTGGAA     720

GAGGAAAGGA AGTCAACTGC AGAACAACTG ACGCGGCTGG ACAACCTGCT GAGAGAGAAA    780

GAAGTTGAAC TGGAGAAACA TATTGCTGCT CACGCCCAAG CCATCTTGAT TGCACAAGAG    840

AAGTATAATG ACACAGCACA GAGTCTGAGG GACGTCACTG CTCAGTTGGA AAGTGTGCAA    900
```

```
GAGAAGTATA ATGACACAGC ACAGAGTCTG AGGGACGTCA CTGCTCAGTT GGAAAGTGAG    960

CAAGAGAAGT ACAATGACAC AGCACAGAGT CTGAGGGACG TCACTGCTCA GTTGGAAAGT   1020

GAGCAAGAGA AGTACAATGA CACAGCACAG AGTCTGAGGG ACGTCACTGC TCAGTTGGAA   1080

AGTGTGCAAG AGAAGTACAA TGACACAGCA CAGAGTCTGA GGGACGTCAC TGCTCAGTTG   1140

GAAAGCTATA GTCATCAAC  ACTTAAAGAA ATAGAAGATC TTAAACTGGA GAATTTGACT   1200

CTACAAGAAA AAGTAGCTAT GGCTGAAAAA GTGTAGAAG  ATGTTCAACA GCAGATATTG   1260

ACAGCTGAGA GCACAAATCA GAATATGCA  GGATGGTTC  AAGATTTGCA GAACAGATCA   1320

ACCTTAAAAG AAGAAGAAAT TAAAGAAATC ACATCTTCAT TTCTTGAGAA ATAACTGAT    1380

TTGAAAAATC AACTCAGACA ACAAGATGAA GACTTTAGGA AGCAGCTGGA AGAGAAAGGA   1440

AAAGAACAG  CAGAGAAAGA AAATGTAATG ACAGAATTAA CCATGGAAAT TAATAAATGG   1500

CGTCTCCTAT ATGATGAACT ATATGAAAAA ACTAAACCTT TTCAGCAACA ACTGGATGCC   1560

TTTGAAGCCG AGAAACAGGC ATTGTTGAAT GAACATGGTG CAACTCAGGA GCAGCTAAAT   1620

AAAATCAGAG ACTCCTATGC ACAGCTACTT GGTCACCAGA ACCTAAAGCA AAAAATCAAA   1680

CATGTTGTGA AATTGAAAGA TGAAAATAGC CAACTCAAAT CGGAGGTGTC AAAACTCCGA   1740

TCTCAGCTTG TTAAAAGGAA ACAAAATGAG CTCAGACTTC AGGGAGAATT AGATAAAGCT   1800

CTGGGCATCA GACACTTTGA CCCTTCCAAG GCTTTTTGTC ATGCATCTAA GGAGAATTTT   1860

ACTCCATTAA AGAAGGCAA  CCCAAACTGC TGCTGA                             1896

(2) INFORMATION FOR SEQ ID NO:11:

(i) SEQUENCE CHARACTERISTICS:
        (A) LENGTH: 631 amino acids
        (B) TYPE: amino acid
        (C) STRANDEDNESS: single
        (D) TOPOLOGY: linear (ii) MOLECULE TYPE: protein
        (A) DESCRIPTION:/desc = "RHAMM I-2a"

(xi) SEQUENCE DESCRIPTION: SEQ ID NO:11:

Met Arg Ala Leu Ser Leu Glu Leu Met Lys Leu Arg Asn Lys Arg Glu
1               5                   10                  15

Thr Lys Met Arg Ser Met Met Val Lys Gln Glu Gly Met Glu Leu Lys
                20                  25                  30

Leu Gln Ala Thr Gln Lys Asp Leu Thr Glu Ser Lys Gly Lys Ile Val
            35                  40                  45

Gln Leu Glu Gly Lys Leu Val Ser Ile Glu Lys Glu Lys Ile Asp Glu
        50                  55                  60

Lys Cys Glu Thr Glu Lys Leu Leu Glu Tyr Ile Gln Glu Ile Ser Cys
65                  70                  75                  80

Ala Ser Asp Gln Val Glu Lys Cys Lys Val Asp Ile Ala Gln Leu Glu
                85                  90                  95

Glu Asp Leu Lys Glu Lys Asp Arg Glu Ile Leu Ser Leu Lys Gln Ser
            100                 105                 110

Leu Glu Glu Asn Ile Thr Phe Ser Lys Gln Ile Glu Asp Leu Thr Val
        115                 120                 125

Lys Cys Gln Leu Leu Glu Thr Glu Arg Asp Asn Leu Val Ser Lys Asp
    130                 135                 140

Arg Glu Arg Ala Glu Thr Leu Ser Ala Glu Met Gln Ile Leu Thr Glu
145                 150                 155                 160
```

```
Arg Leu Ala Leu Glu Arg Gln Glu Tyr Glu Lys Leu Gln Gln Lys Glu
                165                 170                 175
Leu Gln Ser Gln Ser Leu Leu Gln Gln Glu Lys Glu Leu Ser Ala Arg
            180                 185                 190
Leu Gln Gln Gln Leu Cys Ser Phe Gln Glu Glu Met Thr Ser Glu Lys
            195                 200                 205
Asn Val Phe Lys Glu Glu Leu Lys Leu Ala Leu Ala Glu Leu Asp Ala
            210                 215                 220
Val Gln Gln Lys Glu Glu Gln Ser Glu Arg Leu Val Lys Gln Leu Glu
225                 230                 235                 240
Glu Glu Arg Lys Ser Thr Ala Glu Gln Leu Thr Arg Leu Asp Asn Leu
                245                 250                 255
Leu Arg Glu Lys Glu Val Glu Leu Glu Lys His Ile Ala Ala His Ala
            260                 265                 270
Gln Ala Ile Leu Ile Ala Gln Glu Lys Tyr Asn Asp Thr Ala Gln Ser
            275                 280                 285
Leu Arg Asp Val Thr Ala Gln Leu Glu Ser Val Gln Glu Lys Tyr Asn
            290                 295                 300
Asp Thr Ala Gln Ser Leu Arg Asp Val Thr Ala Gln Leu Glu Ser Glu
305                 310                 315                 320
Gln Glu Lys Tyr Asn Asp Thr Ala Gln Ser Leu Arg Asp Val Thr Ala
                325                 330                 335
Gln Leu Glu Ser Glu Gln Glu Lys Tyr Asn Asp Thr Ala Gln Ser Leu
            340                 345                 350
Arg Asp Val Thr Ala Gln Leu Glu Ser Val Gln Glu Lys Tyr Asn Asp
            355                 360                 365
Thr Ala Gln Ser Leu Arg Asp Val Thr Ala Gln Leu Glu Ser Tyr Lys
370                 375                 380
Ser Ser Thr Leu Lys Glu Ile Glu Asp Leu Lys Leu Glu Asn Leu Thr
385                 390                 395                 400
Leu Gln Glu Lys Val Ala Met Ala Glu Lys Ser Val Glu Asp Val Gln
                405                 410                 415
Gln Gln Ile Leu Thr Ala Glu Ser Thr Asn Gln Glu Tyr Ala Arg Met
            420                 425                 430
Val Gln Asp Leu Gln Asn Arg Ser Thr Leu Lys Glu Glu Ile Lys
435                 440                 445
Glu Ile Thr Ser Ser Phe Leu Gly Lys Ile Thr Asp Leu Lys Asn Gln
            450                 455                 460
Leu Arg Gln Gln Asp Glu Asp Phe Arg Lys Gln Leu Glu Glu Lys Gly
465                 470                 475                 480
Lys Arg Thr Ala Glu Lys Glu Asn Val Met Thr Glu Leu Thr Met Glu
                485                 490                 495
Ile Asn Lys Trp Arg Leu Leu Tyr Asp Glu Leu Tyr Glu Lys Thr Lys
            500                 505                 510
Pro Phe Gln Gln Gln Leu Asp Ala Phe Glu Ala Glu Lys Gln Ala Leu
            515                 520                 525
Leu Asn Glu His Gly Ala Thr Gln Glu Gln Leu Asn Lys Ile Arg Asp
            530                 535                 540
Ser Tyr Ala Gln Leu Leu Gly His Gln Asn Leu Lys Gln Lys Ile Lys
545                 550                 555                 560
His Val Val Lys Leu Lys Asp Glu Asn Ser Gln Leu Lys Ser Glu Val
                565                 570                 575
```

```
Ser Lys Leu Arg Ser Gln Leu Val Lys Arg Lys Gln Asn Glu Leu Arg
        580                 585                 590

Leu Gln Gly Glu Leu Asp Lys Ala Leu Gly Ile Arg His Phe Asp Pro
            595                 600                 605

Ser Lys Ala Phe Cys His Ala Ser Lys Glu Asn Phe Thr Pro Leu Lys
        610                 615                 620

Glu Gly Asn Pro Asn Cys Cys
625                 630
```

(2) INFORMATION FOR SEQ ID NO:12:

(i) SEQUENCE CHARACTERISTICS:
        (A) LENGTH: 3044 base pairs
        (B) TYPE: nucleic acid
        (C) STRANDEDNESS: single
        (D) TOPOLOGY: linear (ii) MOLECULE TYPE: cDNA
        (A) DESCRIPTION:/desc = "RHAMM IA cDNA (includes 3' sequence)"

(xi) SEQUENCE DESCRIPTION: SEQ ID NO:12:

```
AGGCCTTAGG TCCAGGAAGG AGGAAAAACC ATCTTCTTCT CTGCGAGTAA TGCTTCACTG      60

GTAAAAACGG CTTACTGAAT TAACCAGAGC CAACGAGCTA CTAAAAGGCT AAAGGATCTG     120

AAGATGGTCA CCAAAAGAAT ATGAGAGCTC TAAGCCTGGA ATTGATGAAA CTCAGAAATA     180

AGAGAGAGAC AAAGATGAGG AGTATGATGG TCAAACAGGA AGGCATGGAG CTGAAGCTGC     240

AGGCCACTCA GAAGGACCTC ACGGAGTCTA AGGGAAAAAT AGTCCAGCTG GAGGGAAAGC     300

TCTGTGCATC TGATCAAGTG AAAAATGCA AAGTAGATAT TGCCCAGTTA GAAGAAGATT      360

TGAAAGAGAA GGATCGTGAG ATTTTAAGTC TTAAGCAGTC TCTTGAGGAA ACATTACAT      420

TTTCTAAGCA AATAGAAGAC CTGACTGTTA AATGCCAGCT ACTTGAAACA GAAAGAGACA     480

ACCTTGTCAG CAAGGATAGA GAAAGGGCTG AAACTCTCAG TGCTGAGATG CAGATCCTGA     540

CAGAGAGGCT GGCTCTGGAA AGGCAAGAAT ATGAAAAGCT GCAACAAAAA GAATTGCAAA     600

GCCAGTCACT TCTGCAGCAA GAGAAGGAAC TGTCTGCTCG TCTGCAGCAG CAGCTCTGCT     660

CTTTCCAAGA GGAAATGACT TCTGAGAAGA ACGTCTTTAA AGAAGAGCTA AAGCTCGCCC     720

TGGCTGAGTT GGATGCGGTC CAGCAGAAGG AGGAGCAGAG TGAAAGGCTG GTTAAACAGC     780

TGGAAGAGGA AAGGAAGTCA ACTGCAGAAC AACTGACGCG GCTGGACAAC CTGCTGAGAG     840

AGAAAGAAGT TGAACTGGAG AAACATATTG CTGCTCACGC CCAAGCCATC TTGATTGCAC     900

AAGAGAAGTA TAATGACACA GCACAGAGTC TGAGGGACGT CACTGCTCAG TTGGAAAGTG     960

TGCAAGAGAA GTATAATGAC ACAGCACAGA GTCTGAGGGA CGTCACTGCT CAGTTGGAAA    1020

GTGAGCAAGA GAAGTACAAT GACACAGCAC AGAGTCTGAG GGACGTCACT GCTCAGTTGG    1080

AAAGTGAGCA AGAAGAGTAC AATGACACAG CACAGAGTCT GAGGGACGTC ACTGCTCAGT    1140

TGGAAAGTGT GCAAGAGAAG TACAATGACA CAGCACAGAG TCTGAGGGAC GTCACTGCTC    1200

AGTTGGAAAG CTATAAGTCA TCAACACTTA AGAAATAGA AGATCTTAAA CTGGAGAATT     1260

TGACTCTACA AGAAAAAGTA GCTATGGCTG AAAAAAGTGT AGAAGATGTT CAACAGCAGA    1320

TATTGACAGC TGAGAGCACA AATCAAGAAT ATGCAAGGAT GGTTCAAGAT TTGCAGAACA    1380

GATCAACCTT AAAAGAAGAA GAAATTAAAG AAATCACATC TTCATTTCTT GAGAAAATAA    1440

CTGATTTGAA AAATCAACTC AGACAACAAG ATGAAGACTT TAGGAAGCAG CTGGAAGAGA    1500

AAGGAAAAAG AACAGCAGAG AAAGAAAATG TAATGACAGA ATTAACCATG GAAATTAATA    1560

AATGGCGTCT CCTATATGAT GAACTATATG AAAAAACTAA ACCTTTTCAG CAACAACTGG    1620
```

```
ATGCCTTTGA AGCCGAGAAA CAGGCATTGT TGAATGAACA TGGTGCAACT CAGGAGCAGC      1680

TAAATAAAAT CAGAGACTCC TATGCACAGC TACTTGGTCA CCAGAACCTA AGCAAAAAA       1740

TCAAACATGT TGTGAAATTG AAAGATGAAA ATAGCCAACT CAAATCGGAG GTGTCAAAAC      1800

TCCGATCTCA GCTTGTTAAA AGGAAACAAA ATGAGCTCAG ACTTCAGGGA GAATTAGATA      1860

AAGCTCTGGG CATCAGACAC TTTGACCCTT CCAAGGCTTT TTGTCATGCA TCTAAGGAGA      1920

ATTTTACTCC ATTAAAAGAA GGCAACCCAA ACTGCTGCTG AGTTCAGATG CAACTTCAAG      1980

AATCATGGAA GTATACGTCT GAAATACTTG TTGAAGATTA TTTTCTTCAT TGTTCTTGAT      2040

ATTATGTTTA TAGTATATAT TATATAATGT ATTTAATTTC TACTGCCTAG TCTTAGGTAT      2100

ATGAAACGGT AATTCAGCAT TTGTTCTCTG TCTTAGTCAG GGTAACATCA GACCAAGAAA      2160

CAACGTGGGG AGGAAAGGGT TTATTCAGCT TACACTTCCA TACTGCTGTT CTGTTCCTGC      2220

ATATTCATCA CCAAAGGAAG TCAGGACTGG AACTGAGGCC ATGGAGGGAC ATTCCTTACT      2280

GGCTTGCTTC CCCTGGCTTG CTCAGCTTGC TTTCTTACAG AACCCAAGTC ATCAGGAAGT      2340

AGGAGCTGAT GCATACCAGC CTAGAGACAG CACCAACCAC AAGGGGCCCT CCCACCCTTG      2400

ATCAATAATT GAGAAAAATG CCTTACAGTT GGATCTCATG AAGGCATTTT CTCACCTGAA      2460

GCTCCTTCTC TGACTCTGAT ACAGGTGGTG TCAAGTTGAC ACACAAACAC ATTACTATTA      2520

AGCCTCAACC CTTACTTTCT TATTAATCCC CATGATCAAA ATAACTTTAA AAGTCCCACA      2580

GTCTTTGTTT AAAATACCAA TCTCTTTTAA AATTCAAAGT GTTTTACAA TTAAAAAGTC       2640

TCTTAACTGT GGTCTCCACT AAAAATTCTT AAAATTTCAA TCCCAAATAC TTTCTTCCTT      2700

CAAGAGGGAA AAATATCAGG GCACAGTCAC AAACAATTAA AAGCAAAATC AAACTACAAC      2760

CTCAAACGTC TGGGACCCTC CAAGGGCTTG GGTCACTTCT CTAGCTCTGC CCTTTGTAGC      2820

ACACAAGTTG TCTTCTAGGC TCCAGATTCC TGTACTCCAC TGCTGCTGCT GTTCTTGGTA      2880

CTCATTTATG GTACTGGCAT CTCCATGTTG TCTTTGCAAA TCATAGGCTC TCTTCATGGT      2940

GCCAAGCCTC AAATCCTTTG AATGACCCCT TCAGTCTTGG GCCATCAACT GCACTGTAAC      3000

TAGGCTTCAC CAATAGCCTC CAGGCTGTAC TGCACTTGGA ATTC                       3044
```

(2) INFORMATION FOR SEQ ID NO:13:

(i) SEQUENCE CHARACTERISTICS:
        (A) LENGTH: 2968 base pairs
        (B) TYPE: nucleic acid
        (C) STRANDEDNESS: single
        (D) TOPOLOGY: linear (ii) MOLECULE TYPE: cDNA
        (A) DESCRIPTION:/desc = "RHAMM IB cDNA (includes 3' sequence)"

(xi) SEQUENCE DESCRIPTION: SEQ ID NO:13:

```
GGCAGAATAG ATATCTGAGT TCTTATGTTT ATTGTAGTTT TCTGAAGATG GTCACCAAAA       60

GAATATGAGA GCTCTAAGCC TGGAATTGAT GAAACTCAGA ATAAGAGAG AGACAAAGAT       120

GAGGAGTATG ATGGTCAAAC AGGAAGGCAT GGAGCTGAAG CTGCAGGCCA CTCAGAAGGA      180

CCTCACGGAG TCTAAGGGAA AAATAGTCCA GCTGGAGGGA AAGCTCTGTG CATCTGATCA      240

AGTGGAAAAA TGCAAAGTAG ATATTGCCCA GTTAGAAGAA GATTTGAAAG AGAAGGATCG      300

TGAGATTTTA AGTCTTAAGC AGTCTCTTGA GGAAAACATT ACATTTTCTA AGCAAATAGA      360

AGACCTGACT GTTAAATGCC AGCTACTTGA AACAGAAAGA GACAACCTTG TCAGCAAGGA      420

TAGAGAAAGG GCTGAAACTC TCAGTGCTGA GATGCAGATC CTGACAGAGA GGCTGGCTCT      480
```

```
GGAAAGGCAA GAATATGAAA AGCTGCAACA AAAAGAATTG CAAAGCCAGT CACTTCTGCA    540

GCAAGAGAAG GAACTGTCTG CTCGTCTGCA GCAGCAGCTC TGCTCTTTCC AAGAGGAAAT    600

GACTTCTGAG AAGAACGTCT TTAAAGAAGA GCTAAAGCTC GCCCTGGCTG AGTTGGATGC    660

GGTCCAGCAG AAGGAGGAGC AGAGTGAAAG GCTGGTTAAA CAGCTGGAAG AGGAAAGGAA    720

GTCAACTGCA GAACAACTGA CGCGGCTGGA CAACCTGCTG AGAGAGAAAG AAGTTGAACT    780

GGAGAAACAT ATTGCTGCTC ACGCCCAAGC CATCTTGATT GCACAAGAGA AGTATAATGA    840

CACAGCACAG AGTCTGAGGG ACGTCACTGC TCAGTTGGAA AGTGTGCAAG AGAAGTATAA    900

TGACACAGCA CAGAGTCTGA GGGACGTCAC TGCTCAGTTG GAAAGTGAGC AAGAGAAGTA    960

CAATGACACA GCACAGAGTC TGAGGGACGT CACTGCTCAG TTGGAAAGTG AGCAAGAGAA   1020

GTACAATGAC ACAGCACAGA GTCTGAGGGA CGTCACTGCT CAGTTGGAAA GTGTGCAAGA   1080

GAAGTACAAT GACACAGCAC AGAGTCTGAG GGACGTCACT GCTCAGTTGG AAAGCTATAA   1140

GTCATCAACA CTTAAAGAAA TAGAAGATCT TAAACTGGAG AATTTGACTC TACAAGAAAA   1200

AGTAGCTATG GCTGAAAAAA GTGTAGAAGA TGTTCAACAG CAGATATTGA CAGCTGAGAG   1260

CACAAATCAA GAATATGCAA GGATGGTTCA AGATTTGCAG AACAGATCAA CCTTAAAAGA   1320

AGAAGAAATT AAAGAAATCA CATCTTCATT TCTTGAGAAA ATAACTGATT TGAAAAATCA   1380

ACTCAGACAA CAAGATGAAG ACTTTAGGAA GCAGCTGGAA GAGAAAGGAA AAAGAACAGC   1440

AGAGAAAGAA AATGTAATGA CAGAATTAAC CATGGAAATT AATAAATGGC GTCTCCTATA   1500

TGATGAACTA TATGAAAAAA CTAAACCTTT TCAGCAACAA CTGGATGCCT TTGAAGCCGA   1560

GAAACAGGCA TTGTTGAATG AACATGGTGC AACTCAGGAG CAGCTAAATA AAATCAGAGA   1620

CTCCTATGCA CAGCTACTTG GTCACCAGAA CCTAAAGCAA AAAATCAAAC ATGTTGTGAA   1680

ATTGAAAGAT GAAAATAGCC AACTCAAATC GGAGGTGTCA AAACTCCGAT CTCAGCTTGT   1740

TAAAAGGAAA CAAAATGAGC TCAGACTTCA GGGAGAATTA GATAAAGCTC TGGGCATCAG   1800

ACACTTTGAC CCTTCCAAGG CTTTTTGTCA TGCATCTAAG GAGAATTTTA CTCCATTAAA   1860

AGAAGGCAAC CCAAACTGCT GCTGAGTTCA GATGCAACTT CAAGAATCAT GGAAGTATAC   1920

GTCTGAAATA CTTGTTGAAG ATTATTTTCT TCATTGTTCT TGATATTATG TTTATAGTAT   1980

ATATTATATA ATGTATTTAA TTTCTACTGC CTAGTCTTAG GTATATGAAA CGGTAATTCA   2040

GCATTTGTTC TCTGTCTTAG TCAGGGTAAC ATCAGACCAA GAAACAACGT GGGGAGGAAA   2100

GGGTTTATTC AGCTTACACT TCCATACTGC TGTTCTGTTC CTGCATATTC ATCACCAAAG   2160

GAAGTCAGGA CTGGAACTGA GGCCATGGAG GGACATTCCT TACTGGCTTG CTTCCCCTGG   2220

CTTGCTCAGC TTGCTTTCTT ACAGAACCCA AGTCATCAGG AAGTAGGAGC TGATGCATAC   2280

CAGCCTAGAG ACAGCACCAA CCACAAGGGG CCCTCCCACC CTTGATCAAT AATTGAGAAA   2340

AATGCCTTAC AGTTGGATCT CATGAAGGCA TTTTCTCACC TGAAGCTCCT TCTCTGACTC   2400

TGATACAGGT GGTGTCAAGT TGACACACAA ACACATTACT ATTAAGCCTC AACCCTTACT   2460

TTCTTATTAA TCCCCATGAT CAAAATAACT TTAAAGTCC CACAGTCTTT GTTTAAAATA   2520

CCAATCTCTT TTAAAATTCA AAGTGTTTTT ACAATTAAAA AGTCTCTTAA CTGTGGTCTC   2580

CACTAAAAAT TCTTAAAATT TCAATCCCAA ATACTTTCTT CCTTCAAGAG GGAAAAATAT   2640

CAGGGCACAG TCACAAACAA TTAAAAGCAA AATCAAACTA CAACCTCAAA CGTCTGGGAC   2700

CCTCCAAGGG CTTGGGTCAC TTCTCTAGCT CTGCCCTTTG TAGCACACAA GTTGTCTTCT   2760

AGGCTCCAGA TTCCTGTACT CCACTGCTGC TGCTGTTCTT GGTACTCATT TATGGTACTG   2820

GCATCTCCAT GTTGTCTTTG CAAATCATAG GCTCTCTTCA TGGTGCCAAG CCTCAAATCC   2880
```

```
TTTGAATGAC CCCTTCAGTC TTGGGCCATC AACTGCACTG TAACTAGGCT TCACCAATAG      2940

CCTCCAGGCT GTACTGCACT TGGAATTC                                        2968

(2) INFORMATION FOR SEQ ID NO:14:

(i) SEQUENCE CHARACTERISTICS:
        (A) LENGTH: 1083 base pairs
        (B) TYPE: nucleic acid
        (C) STRANDEDNESS: single
        (D) TOPOLOGY: linear (ii) MOLECULE TYPE: cDNA
        (A) DESCRIPTION:/desc = "3' untranslated sequence"

(xi) SEQUENCE DESCRIPTION: SEQ ID NO:14:

GTTCAGATGC AACTTCAAGA ATCATGGAAG TATACGTCTG AAATACTTGT TGAAGATTAT        60

TTTCTTCATT GTTCTTGATA TTATGTTTAT AGTATATATT ATATAATGTA TTTAATTTCT       120

ACTGCCTAGT CTTAGGTATA TGAAACGGTA ATTCAGCATT TGTTCTCTGT CTTAGTCAGG       180

GTAACATCAG ACCAAGAAAC AACGTGGGGA GGAAAGGGTT TATTCAGCTT ACACTTCCAT       240

ACTGCTGTTC TGTTCCTGCA TATTCATCAC CAAAGGAAGT CAGGACTGGA ACTGAGGCCA       300

TGGAGGGACA TTCCTTACTG GCTTGCTTCC CCTGGCTTGC TCAGCTTGCT TTCTTACAGA       360

ACCCAAGTCA TCAGGAAGTA GGAGCTGATG CATACCAGCC TAGAGACAGC ACCAACCACA       420

AGGGGCCCTC CCACCCTTGA TCAATAATTG AGAAAAATGC CTTACAGTTG GATCTCATGA       480

AGGCATTTTC TCACCTGAAG CTCCTTCTCT GACTCTGATA CAGGTGGTGT CAAGTTGACA       540

CACAAACACA TTACTATTAA GCCTCAACCC TTACTTTCTT ATTAATCCCC ATGATCAAAA       600

TAACTTTAAA AGTCCCACAG TCTTTGTTTA AAATACCAAT CTCTTTTAAA ATTCAAAGTG       660

TTTTTACAAT TAAAAAGTCT CTTAACTGTG GTCTCCACTA AAAATTCTTA AAATTTCAAT       720

CCCAAATACT TTCTTCCTTC AAGAGGGAAA AATATCAGGG CACAGTCACA AACAATTAAA       780

AGCAAAATCA AACTACAACC TCAAACGTCT GGGACCCTCC AAGGGCTTGG GTCACTTCTC       840

TAGCTCTGCC CTTTGTAGCA CACAAGTTGT CTTCTAGGCT CCAGATTCCT GTACTCCACT       900

GCTGCTGCTG TTCTTGGTAC TCATTTATGG TACTGGCATC TCCATGTTGT CTTTGCAAAT       960

CATAGGCTCT CTTCATGGTG CCAAGCCTCA AATCCTTTGA ATGACCCCTT CAGTCTTGGG      1020

CCATCAACTG CACTGTAACT AGGCTTCACC AATAGCCTCC AGGCTGTACT GCACTTGGAA      1080

TTC                                                                   1083

(2) INFORMATION FOR SEQ ID NO:15:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE:
        (A) DESCRIPTION:/desc = intron sequence (xi) SEQUENCE DESCRIPTION: SEQ ID NO:15:

AAGTATCTGA TACCACACCT AGCCTTAAAT AATTATATTT ATGATGT                     47

(2) INFORMATION FOR SEQ ID NO:16:

(i) SEQUENCE CHARACTERISTICS:
        (A) LENGTH: 12 base pairs
        (B) TYPE: nucleic acid
```

```
        (C) STRANDEDNESS: single
        (D) TOPOLOGY: linear (ii) MOLECULE TYPE:
        (A) DESCRIPTION:/desc = intron sequence (xi) SEQUENCE DESCRIPTION: SEQ ID NO:16:

GTGAGTGCTT GC                                                    12

(2) INFORMATION FOR SEQ ID NO:17:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE:
        (A) DESCRIPTION:/desc = intron sequence (xi) SEQUENCE DESCRIPTION: SEQ ID NO:17:

TGTGTTGTGC AG                                                    12

(2) INFORMATION FOR SEQ ID NO:18:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE:
        (A) DESCRIPTION:/desc = intron sequence (xi) SEQUENCE DESCRIPTION: SEQ ID NO:18:

CATGTGGCAC AA                                                    12

(2) INFORMATION FOR SEQ ID NO:19:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE:
        (A) DESCRIPTION:/desc = intron sequence (xi) SEQUENCE DESCRIPTION: SEQ ID NO:19:

CTTTTAATAC AG                                                    12

(2) INFORMATION FOR SEQ ID NO:20:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE:
        (A) DESCRIPTION:/desc = intron sequence (xi) SEQUENCE DESCRIPTION: SEQ ID NO:20:

GTACTGTGCT GT                                                    12

(2) INFORMATION FOR SEQ ID NO:21:

(i) SEQUENCE CHARACTERISTICS:
        (A) LENGTH: 14 base pairs
```

(B) TYPE: nucleic acid
        (C) STRANDEDNESS: single
        (D) TOPOLOGY: linear (ii) MOLECULE TYPE:
        (A) DESCRIPTION:/desc = intron sequence (xi) SEQUENCE DESCRIPTION: SEQ ID NO:21:

AGTCTCTCTT ACAG                                                    14

(2) INFORMATION FOR SEQ ID NO:22:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE:
        (A) DESCRIPTION:/desc = intron sequence (xi) SEQUENCE DESCRIPTION: SEQ ID NO:22:

GTAGCTCCAC AT                                                      12

(2) INFORMATION FOR SEQ ID NO:23:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE:
        (A) DESCRIPTION:/desc = intron sequence (xi) SEQUENCE DESCRIPTION: SEQ ID NO:23:

TGTCTGAATG CAG                                                     13

(2) INFORMATION FOR SEQ ID NO:24:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE:
        (A) DESCRIPTION:/desc = intron sequence (xi) SEQUENCE DESCRIPTION: SEQ ID NO:24:

GTTTGTATTA AT                                                      12

(2) INFORMATION FOR SEQ ID NO:25:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE:
        (A) DESCRIPTION:/desc = intron sequence (xi) SEQUENCE DESCRIPTION: SEQ ID NO:25:

TCTTGTCTTT AG                                                      12

(2) INFORMATION FOR SEQ ID NO:26:

(i) SEQUENCE CHARACTERISTICS:

(A) LENGTH: 12 base pairs
        (B) TYPE: nucleic acid
        (C) STRANDEDNESS: single
        (D) TOPOLOGY: linear (ii) MOLECULE TYPE:
        (A) DESCRIPTION:/desc = intron sequence (xi) SEQUENCE DESCRIPTION: SEQ ID NO:26:

GTATTTTCCT TT                                                          12

(2) INFORMATION FOR SEQ ID NO:27:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE:
        (A) DESCRIPTION:/desc = intron sequence (xi) SEQUENCE DESCRIPTION: SEQ ID NO:27:

TCCCTTTATA AG                                                          12

(2) INFORMATION FOR SEQ ID NO:28:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE:
        (A) DESCRIPTION:/desc = intron sequence (xi) SEQUENCE DESCRIPTION: SEQ ID NO:28:

GTGAGTACAA CT                                                          12

(2) INFORMATION FOR SEQ ID NO:29:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE:
        (A) DESCRIPTION:/desc = intron sequence (xi) SEQUENCE DESCRIPTION: SEQ ID NO:29:

TCAAATCTAA GG                                                          12

(2) INFORMATION FOR SEQ ID NO:30:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE:
        (A) DESCRIPTION:/desc = intron sequence (xi) SEQUENCE DESCRIPTION: SEQ ID NO:30:

GTAAGTCAGG CT                                                          12

(2) INFORMATION FOR SEQ ID NO:31:

```
        (i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE:
            (A) DESCRIPTION:/desc = intron sequence (xi) SEQUENCE DESCRIPTION: SEQ ID NO:31:

TTTCCCATAC AG                                                        12

(2) INFORMATION FOR SEQ ID NO:32:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE:
            (A) DESCRIPTION:/desc = intron sequence (xi) SEQUENCE DESCRIPTION: SEQ ID NO:32:

GTAAGTCAGG CT                                                        12

(2) INFORMATION FOR SEQ ID NO:33:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (ii) MOLECULE TYPE:
            (A) DESCRIPTION:/desc = intron sequence (xi) SEQUENCE DESCRIPTION: SEQ ID NO:33:

TTTCCATACA G                                                         11

(2) INFORMATION FOR SEQ ID NO:34:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE:
            (A) DESCRIPTION:/desc = intron sequence (xi) SEQUENCE DESCRIPTION: SEQ ID NO:34:

GTTTGTAAAA TA                                                        12

(2) INFORMATION FOR SEQ ID NO:35:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE:
            (A) DESCRIPTION:/desc = intron sequence (xi) SEQUENCE DESCRIPTION: SEQ ID NO:35:

TTTCTTTCAC AG                                                        12

(2) INFORMATION FOR SEQ ID NO:36:
```

(i) SEQUENCE CHARACTERISTICS:
    (A) LENGTH: 12 base pairs
    (B) TYPE: nucleic acid
    (C) STRANDEDNESS: single
    (D) TOPOLOGY: linear (ii) MOLECULE TYPE:
    (A) DESCRIPTION:/desc = intron sequence (xi) SEQUENCE DESCRIPTION: SEQ ID NO:36:

GTAAAAAAAA GT                                                    12

(2) INFORMATION FOR SEQ ID NO:37:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE:
        (A) DESCRIPTION:/desc = intron sequence (xi) SEQUENCE DESCRIPTION: SEQ ID NO:37:

TACTCTTCTT CAG                                                   13

(2) INFORMATION FOR SEQ ID NO:38:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE:
        (A) DESCRIPTION:/desc = protein fragment (xi) SEQUENCE DESCRIPTION: SEQ ID NO:38:

Lys Gln Lys Ile Lys His Val Val Lys Leu Lys Glu Asp Asn Ser Gln
1               5                   10                  15

Leu Lys Ser Glu Val Ser Lys Leu Arg Ser Gln Leu Val Lys Arg Lys
            20                  25                  30

(2) INFORMATION FOR SEQ ID NO:39:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE:
        (A) DESCRIPTION:/desc = protein fragment (xi) SEQUENCE DESCRIPTION: SEQ ID NO:39:

Lys Gln Lys Ile Glu His Val Val Glu Leu Lys Leu Asp Asn Ser Gln
1               5                   10                  15

Leu Lys Ser Glu Val Ser Lys Leu Arg Ser Gln Leu Val Asn Trp Glu
            20                  25                  30

(2) INFORMATION FOR SEQ ID NO:40:

(i) SEQUENCE CHARACTERISTICS:
        (A) LENGTH: 183 amino acids
        (B) TYPE: amino acid
        (C) STRANDEDNESS: single
        (D) TOPOLOGY: linear (ii) MOLECULE TYPE:
            (A) DESCRIPTION:/desc = protein fragment (xi) SEQUENCE DESCRIPTION: SEQ ID NO:40:

Ile Glu Asp Leu Lys Leu Glu Asn Ser Ser Leu Gln Glu Glu Ala Ala
1               5                   10                  15

Lys Ala Gly Lys Asn Ala Glu Asp Val Gln His Gln Ile Leu Ala Thr
            20                  25                  30

Glu Ser Ser Asn Gln Glu Tyr Val Arg Met Leu Leu Asp Leu Gln Thr
        35                  40                  45

Lys Ser Ala Leu Lys Glu Thr Glu Ile Lys Glu Ile Thr Val Ser Phe
50                  55                  60

Leu Gln Lys Ile Thr Asp Gln Asn Gln Leu Lys Gln Gln Glu Glu
65                  70                  75                  80

Asp Phe Arg Asn Arg Leu Glu Asp Glu Glu Gly Arg Thr Ala Glu Lys
                85                  90                  95

Glu Asn Pro Thr Pro Glu Leu Thr Met Glu Ile Asn Lys Trp Arg Leu
            100                 105                 110

Leu Tyr Asp Glu Leu Tyr Glu Lys Thr Lys Pro Phe Gln Gln Gln Leu
        115                 120                 125

Asp Ala Phe Glu Val Glu Lys Gln Ala Leu Leu Asp Glu His Gly Ala
    130                 135                 140

Ala Gln Glu Gln Leu Asn Lys Ile Arg Asp Ser Tyr Ala Lys Leu Leu
145                 150                 155                 160

Gly His Gln Asn Leu Lys Gln Lys Ile Arg His Val Val Lys Leu Lys
                165                 170                 175

Asp Glu Asn Ser Gln Leu Lys
            180

(2) INFORMATION FOR SEQ ID NO:41:

(i) SEQUENCE CHARACTERISTICS:
            (A) LENGTH: 183 amino acids
            (B) TYPE: amino acid
            (C) STRANDEDNESS: single
            (D) TOPOLOGY: linear (ii) MOLECULE TYPE:
            (A) DESCRIPTION:/desc = protein fragment (xi) SEQUENCE DESCRIPTION: SEQ ID NO:41:

Ile Glu Asp Leu Lys Leu Glu Asn Leu Thr Leu Gln Glu Lys Val Ala
1               5                   10                  15

Met Ala Glu Lys Ser Val Glu Asp Val Gln Gln Gln Ile Leu Thr Ala
            20                  25                  30

Glu Ser Thr Asn Gln Glu Tyr Ala Arg Met Val Gln Asp Leu Gln Asn
        35                  40                  45

Arg Ser Thr Leu Lys Glu Glu Ile Lys Glu Ile Thr Ser Ser Phe
50                  55                  60

Leu Glu Lys Ile Thr Asp Leu Leu Asn Gln Leu Arg Gln Gln Asp Glu
65                  70                  75                  80

Asp Phe Arg Lys Gln Leu Glu Gly Lys Gly Lys Arg Thr Ala Glu Lys
                85                  90                  95

Glu Asn Val Met Thr Glu Leu Thr Met Glu Ile Asn Lys Trp Arg Leu
            100                 105                 110

Leu Tyr Glu Glu Leu Tyr Glu Lys Thr Lys Pro Phe Gln Gln Gln Leu
        115                 120                 125

```
Asp Ala Phe Glu Ala Glu Lys Gln Ala Leu Leu Asn Glu His Gly Ala
    130                 135                 140

Thr Gln Glu Gln Leu Asn Lys Ile Arg Asp Ser Tyr Ala Gln Leu Leu
145                 150                 155                 160

Gly His Gln Asn Leu Lys Gln Lys Ile Lys His Val Val Lys Leu Lys
                165                 170                 175

Asp Glu Asn Ser Gln Leu Lys
            180
```

(2) INFORMATION FOR SEQ ID NO:42:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE:
        (A) DESCRIPTION: /desc =

(xi) SEQUENCE DESCRIPTION: SEQ ID NO:42:

ATGCAGATCC TGACAGAGAG G                                           21

(2) INFORMATION FOR SEQ ID NO:43:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE:
        (A) DESCRIPTION: /desc =

(xi) SEQUENCE DESCRIPTION: SEQ ID NO:43:

CTGCATTCAG ACAGGTAAG CA                                         21

(2) INFORMATION FOR SEQ ID NO:44:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE:
        (A) DESCRIPTION: /desc =

(xi) SEQUENCE DESCRIPTION: SEQ ID NO:44:

TTCCAGAGCC AGCCTCTCTG T                                         21

(2) INFORMATION FOR SEQ ID NO:45:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE:
        (A) DESCRIPTION: /desc =

(xi) SEQUENCE DESCRIPTION: SEQ ID NO:45:

TCATCTTTGT CTCTCTCCTC TTATTTCT                                 28

(2) INFORMATION FOR SEQ ID NO:46:

```
    (i) SEQUENCE CHARACTERISTICS:
        (A) LENGTH:  31 base pairs
        (B) TYPE:  nucleic acid
        (C) STRANDEDNESS:   single
        (D) TOPOLOGY:   linear (ii) MOLECULE TYPE:
        (A) DESCRIPTION: /desc =

(xi) SEQUENCE DESCRIPTION: SEQ ID NO:46:

GGATCCAGTA CTTCTGAGAA GAACGTCTTT A                                31

(2) INFORMATION FOR SEQ ID NO:47:

(i) SEQUENCE CHARACTERISTICS:
        (A) LENGTH: 32 base pairs
        (B) TYPE: nucleic acid
        (C) STRANDEDNESS:   single
        (D) TOPOLOGY:   linear (ii) MOLECULE TYPE:
        (A) DESCRIPTION: /desc =

(xi) SEQUENCE DESCRIPTION: SEQ ID NO:47:

AGTGGATCCC AAGCCATCTT GATGCACAAG AG                               32

(2) INFORMATION FOR SEQ ID NO:48:

(i) SEQUENCE CHARACTERISTICS:
        (A) LENGTH: 21 base pairs
        (B) TYPE: nucleic acid
        (C) STRANDEDNESS:   single
        (D) TOPOLOGY:   linear (ii) MOLECULE TYPE:
        (A) DESCRIPTION: /desc =

(xi) SEQUENCE DESCRIPTION: SEQ ID NO:48:

TGGAGTAAAA TTCTCCTTAG A                                           21

(2) INFORMATION FOR SEQ ID NO:49:

(i) SEQUENCE CHARACTERISTICS:
        (A) LENGTH:  21 base pairs
        (B) TYPE:  nucleic acid
        (C) STRANDEDNESS:   single
        (D) TOPOLOGY:   linear (ii) MOLECULE TYPE:
        (A) DESCRIPTION: /desc =

(xi) SEQUENCE DESCRIPTION: SEQ ID NO:49:

AAATAGAAGA TCTTAAACTG G                                           21

(2) INFORMATION FOR SEQ ID NO:50:

(i) SEQUENCE CHARACTERISTICS:
        (A) LENGTH:   21 base pairs
        (B) TYPE:   nucleic acid
        (C) STRANDEDNESS:   single
        (D) TOPOLOGY:   linear (ii) MOLECULE TYPE:
        (A) DESCRIPTION: /desc =

(xi) SEQUENCE DESCRIPTION: SEQ ID NO:50:

TGGAGTAAAA TTCTCCTTAG A                                           21

(2) INFORMATION FOR SEQ ID NO:51:
```

(i) SEQUENCE CHARACTERISTICS:
        (A) LENGTH:   30 base pairs
        (B) TYPE:  nucleic acid
        (C) STRANDEDNESS:   single
        (D) TOPOLOGY:   linear (ii) MOLECULE TYPE:
        (A) DESCRIPTION: /desc =

(xi) SEQUENCE DESCRIPTION: SEQ ID NO:51:

GTGGATCCAT CCAGATCCTG ACAGAGAGGC                                       30

(2) INFORMATION FOR SEQ ID NO:52:

(i) SEQUENCE CHARACTERISTICS:
        (A) LENGTH:   26 base pairs
        (B) TYPE:  nucleic acid
        (C) STRANDEDNESS:   single
        (D) TOPOLOGY:   linear (ii) MOLECULE TYPE:
        (A) DESCRIPTION: /desc =

(xi) SEQUENCE DESCRIPTION: SEQ ID NO:52:

AATGAATTCC TTTGGTGAAC AGCAGT                                           26

(2) INFORMATION FOR SEQ ID NO:53:

(i) SEQUENCE CHARACTERISTICS:
        (A) LENGTH:   30 base pairs
        (B) TYPE:  nucleic acid
        (C) STRANDEDNESS:   single
        (D) TOPOLOGY:   linear (ii) MOLECULE TYPE:
        (A) DESCRIPTION: /desc =

(xi) SEQUENCE DESCRIPTION: SEQ ID NO:53:

TAGCTTGTAC AACACCTTAA CTTCGAAAAT                                       30

(2) INFORMATION FOR SEQ ID NO:54:

(i) SEQUENCE CHARACTERISTICS:
        (A) LENGTH:   30 base pairs
        (B) TYPE:  nucleic acid
        (C) STRANDEDNESS:   single
        (D) TOPOLOGY:   linear (ii) MOLECULE TYPE:
        (A) DESCRIPTION: /desc =

(xi) SEQUENCE DESCRIPTION: SEQ ID NO:54:

CAATTAACCC TTGTTTTACT CGAGTCTGAA                                       30

(2) INFORMATION FOR SEQ ID NO:55:

(i) SEQUENCE CHARACTERISTICS:
        (A) LENGTH:   21 base pairs
        (B) TYPE: nucleic acid
        (C) STRANDEDNESS:   single
        (D) TOPOLOGY:   linear (ii) MOLECULE TYPE:
        (A) DESCRIPTION: /desc =

(xi) SEQUENCE DESCRIPTION: SEQ ID NO:55:

TTTGAGTTGG CTATTTTCAT C                                                21

(2) INFORMATION FOR SEQ ID NO:56:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE:
        (A) DESCRIPTION: /desc =

(xi) SEQUENCE DESCRIPTION: SEQ ID NO:56:

ATCTGGCACC ACACCTTCTA GAATGAGCTG CG                32

(2) INFORMATION FOR SEQ ID NO:57:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE:
        (A) DESCRIPTION: /desc =

(xi) SEQUENCE DESCRIPTION: SEQ ID NO:57:

CGTCTACACC TAGTCGTTCG TCCTCATACT GC                32

(2) INFORMATION FOR SEQ ID NO:58:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE:
        (a) DESCRIPTION: /desc = protein fragment (xi) SEQUENCE DESCRIPTION: SEQ ID NO:58:

Leu Asp Asn Gln Ile Lys Lys Met
1           5

(2) INFORMATION FOR SEQ ID NO:59:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE:
        (A) DESCRIPTION: /desc =

(xi) SEQUENCE DESCRIPTION: SEQ ID NO:59:

GCGGTCGACA TGAGAGCTCT AAGCCTGGAA                  30

(2) INFORMATION FOR SEQ ID NO:60:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE:
        (A) DESCRIPTION: /desc =

(xi) SEQUENCE DESCRIPTION: SEQ ID NO:60:

CGCGGATCCC CTTTGGTGAT GAACAGCAG                29

HYALURONAN RECEPTOR PROTEIN

The present invention relates to a novel hyaluronan receptor protein involved in cell locomotion or motility and in cell proliferation and transformation and to DNA sequences encoding this protein. The protein is designated Receptor for Hyaluronic Acid Mediated Motility or RHAMM.

In the description which follows, references are made to certain literature citations which are listed at the end of the specification.

BACKGROUND OF THE INVENTION

Hyaluronan or hyaluronic acid ("HA") is a large glycosaminoglycan that is ubiquitous in the extracellular matrix and whose synthesis has been linked to cell migration, growth and transformation (Turley 1984; Toole et al, 1984; Iozzo 1985; Boudreaux et al., 1991). This glycosaminoglycan interacts with cell surfaces via specific protein receptors that mediate many of its biological effects (Turley 1992). Three distinct hyaluronan receptors, CD44 (Dalchau et al., 1980; Aruffo et al., 1990; Stamankovic et al. 1991), RHAMM II (Hardwick et al., 1992; Yang et al., 1993), and HARLEC (Forsberg and Gustafson 1991; Rampyari et al., 1988) have been previously isolated and characterized. These receptors regulate cell locomotion and have been implicated in malignant transformation.

BRIEF DESCRIPTION OF THE DRAWINGS

Throughout the disclosure; references to RHAMM peptides identified by amino acid number are with reference to the amino acid sequence of RHAMM II (ie. commencing at amino acid 130 of FIG. 1).

Preferred embodiments of the present invention are described below with reference to the accompanying drawings in which:

FIG. 1 shows the nucleotide sequence and deduced amino acid sequence of the RHAMM I gene (Exons 1 to 12).

The cDNA sequence is in uppercase letters, intron boundaries are in lower case letters. Twelve nucleotides are presented for each intron/exon boundary. The translation initiation codons, AUG 1 (+1) and AUG 2(+388), are boxed. The termination codon is indicated by an asterisk. The transcript start point (tsp) for RHAMM I is indicated by an arrow in position −31. Numbers on the left and right correspond to the amino acid sequence FIG. 1 includes the following intron boundaries:

aagtatctgataccacacctagccttaaataattatatttatgatgt (SEQ ID NO:15);
gtgagtgcttgc (SEQ ID NO:16);
tgtgttgtgcag (SEQ ID NO:17);
catgtggcacaa (SEQ ID NO:18);
cttttaatacag (SEQ ID NO:19);
gtactgtgctgt (SEQ ID NO:20);
bagtctctcttacag (SEQ ID NO:21);
bgtagctccacat (SEQ ID NO:22);
tgtctgaatgcag (SEQ ID NO:23);
gtttgtattaat (SEQ ID NO:24);
tcttgtctttag (SEQ ID NO:25);
gtattttcctt (SEQ ID NO:26);
tccctttataag (SEQ ID NO:27);
gtgagtacaact (SEQ ID NO:28);
tcaaatctaagg (SEQ ID NO:29);
gtaagtcaggct (SEQ ID NO:30);
tttcccatacag (SEQ ID NO:31);
gtaagtcaggct (SEQ ID NO:32);
tttccatacag (SEQ ID NO:33);
gtttgtaaaata (SEQ ID NO:34);
tttctttcacag (SEQ ID NO:35);
gtaaaaaaagt (SEQ ID NO:36);
tactcttcttcag (SEQ ID NO:37).

Figure 1B:
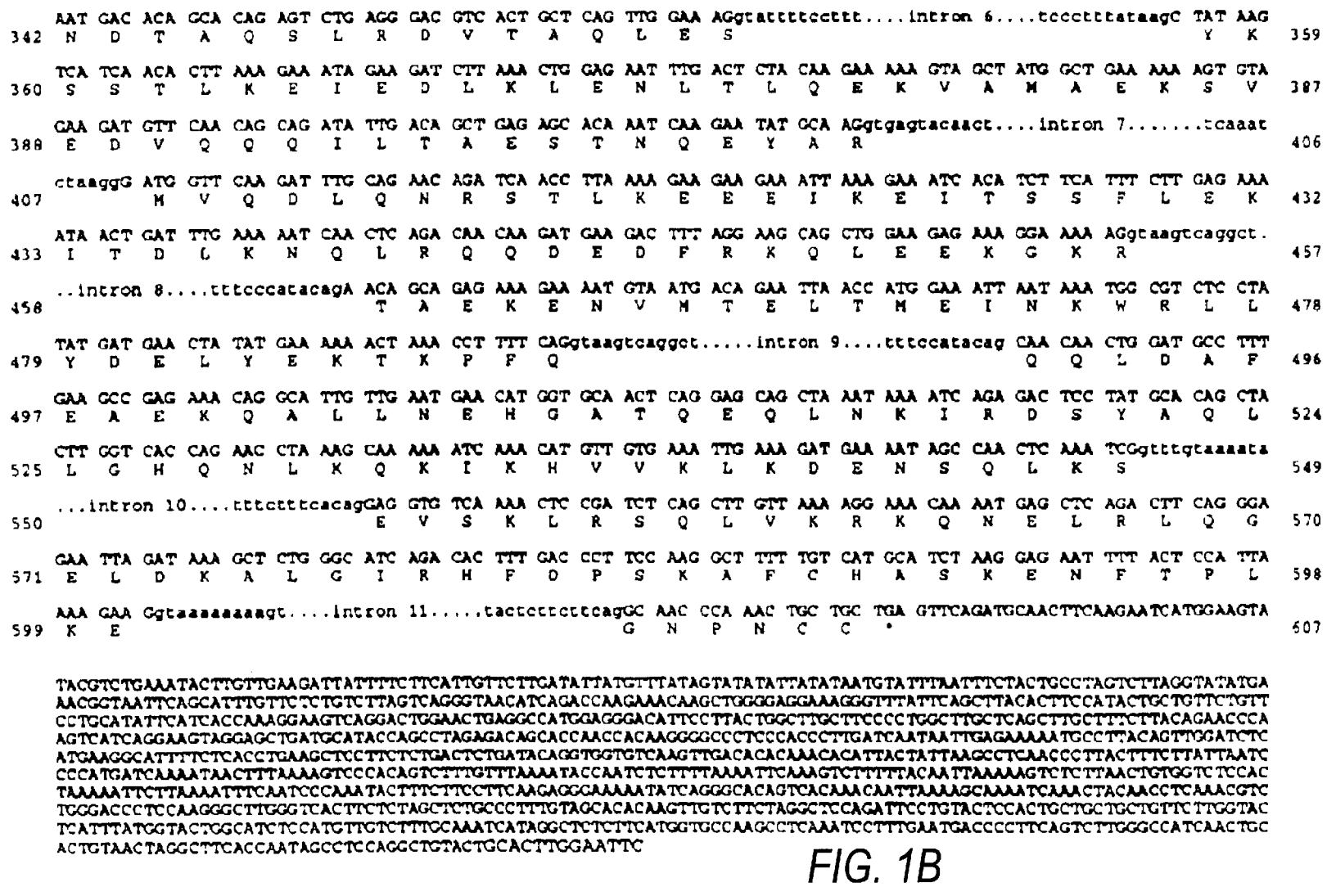

FIG. 1 also includes the 5' untranslated sequence of the RHAMM I gene (SEQ ID NO:6) and the 3' untranslated sequence of the RHAMM I gene (SEQ ID NO:14). In addition, FIG. 1 includes the nucleotide sequence of RHAMM I cDNA (SEQ ID NO:1) and the deduced amino acid sequence of RHAMM I protein (SEQ ID NO:2).

Figure 2A:

FIG. 2 shows ,the nucleotide sequence (SEQ ID NO:1) and deduced amino acid sequence (SEQ ID NO:2) of WRHAMM I cDNA (Exons 1 to 12).

The translation initiation codon for RHAMM I(AUG 1) is boxed and the translation initiation codon for RHAMM II(AUG 2) is indicated by a hatched box. The termination codon is indicated by an asterisk. Numbers on the left correspond to the nucleotide sequence beginning with the first methionine of the open reading frame (AUG 1). Potential glycosylation sites from N-linked glycans are underlined.

Figure 3:
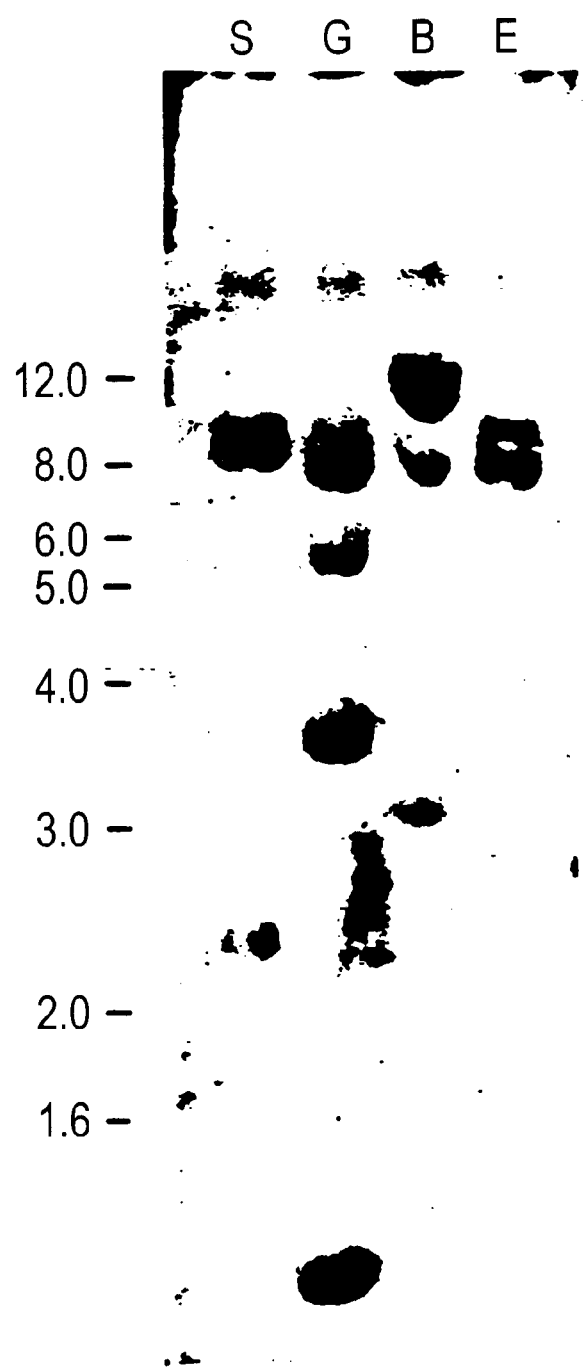

FIG. 3 shows a Southern blot analysis of mouse genomic DNA, after digestion with restriction endonucleases as follows:

Lane S: SacI; Lane G: Bgl II; Lane B: Bam HI and Lane E: EcoRI.

Figure 4:
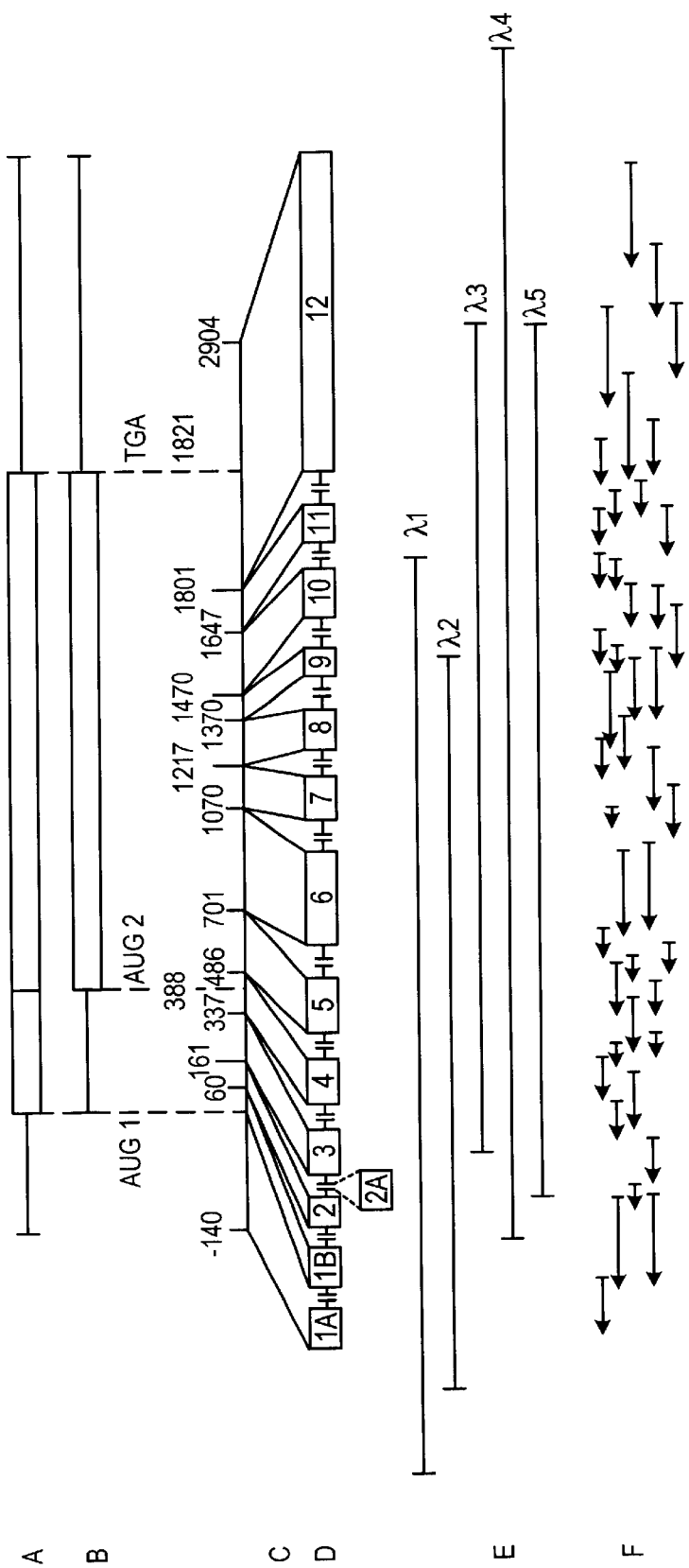

FIG. 4 shows in schematic form the 14 exons making up the RHAMM gene:

A and B: Schematic representations of the organization of the RHAMM I and RHAMM II cDNA clones. Single lines indicate the 5' and 3' non-coding regions. coding regions are boxed and shaded areas represent the overlapping regions of these clones;

C and D: Alignment of the cDNA clones RHAMM I and RHAMM II with the RHAMM gene. Numbers indicate exon/intron boundaries, AUG I being nucleotide 1, AUG 2 is in position 388 and 1821 is the stop codon. Open boxes indicate exons 1A, 1B, 2, 2A and 3 to 12. The diagonally hatched region in exon 6 corresponds to the 21 amino acids repeated five times and the horizontal hatching in exons 10 and 11 correspond to the HA binding domains 1 and 2, respectively;

E: Overlapping lambda clones that were isolated and found to cover the entire RHAMM gene;

F: Arrows indicate the sequencing strategy.

Figures 5A, 5B, 5C:
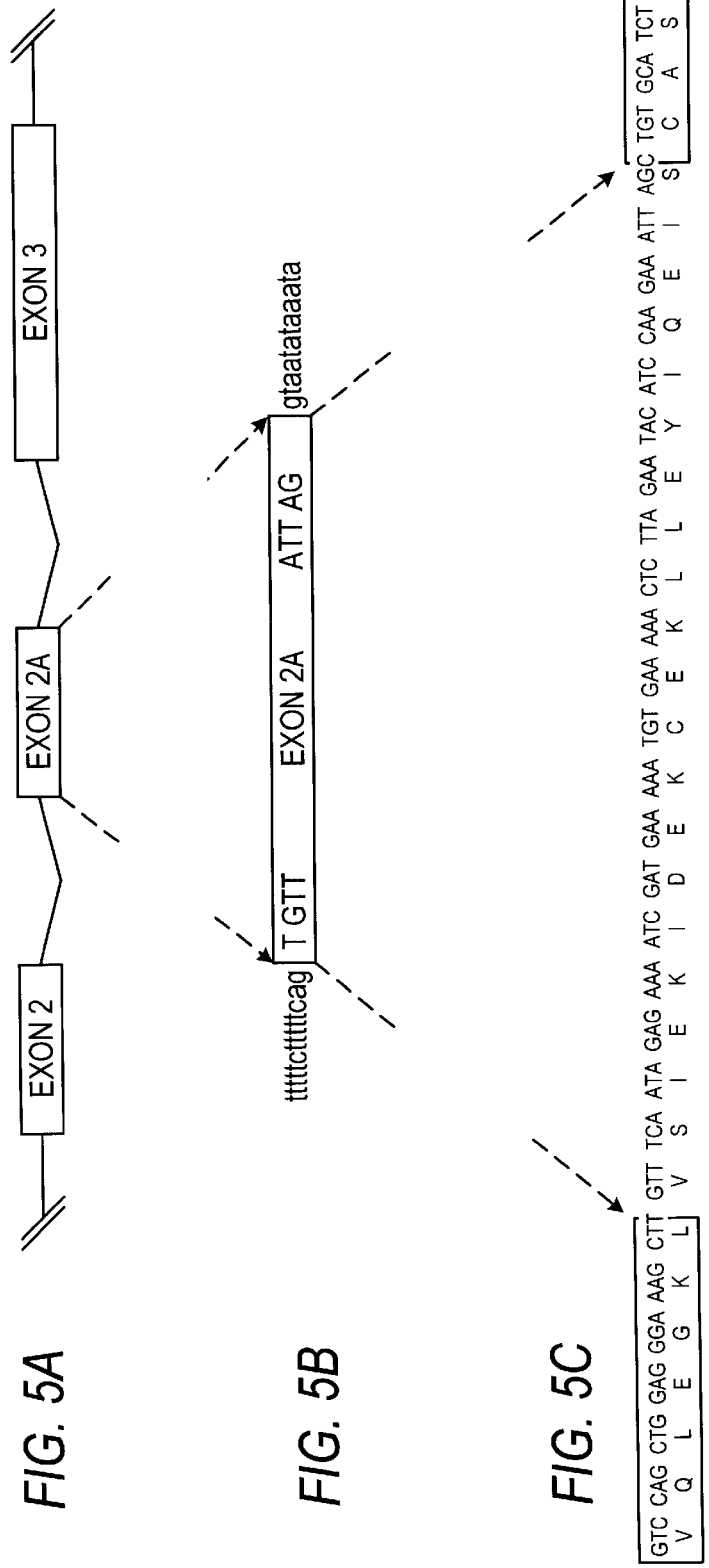

FIG. 5 is a schematic representation, nucleotide and deduced amino acid sequence of the alternately spliced exon 2A:

A: Diagrammatic representation of alternately spliced exon 2A.

B: Intron/exon boundaries of exon 2A.

C: Nucleotide (SEQ ID NO:3) and deduced amino acid sequence (SEQ ID NO:4) of exon 2A.

Figure 6:
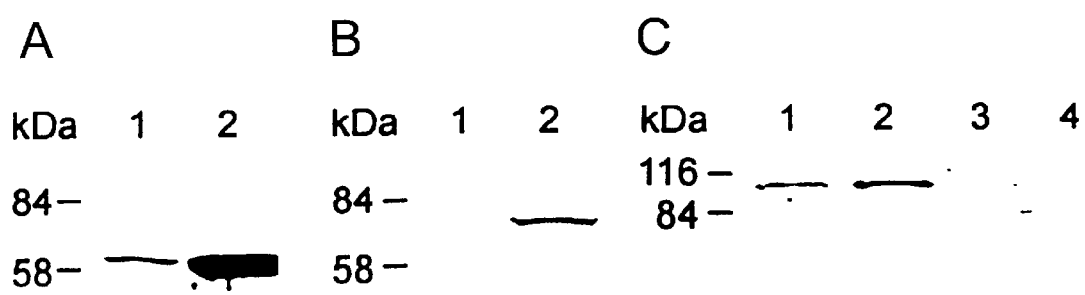

FIG. 6 shows a Western analysis of cells transfected with RHAMM I-2a and RHAMM II cDNAs.

A: Overexpression of the RHAMM II isoform in cell lysates. Lane 1: vector control; Lane 2: vector containing RHAMM II cDNA.

B: Overexpression of RHAMM I-2a in cell lysates. Lane 1: vector control; Lane 2: vector containing RHAMM I-2a cDNA.

C: Overexpression of RHAMM I-2a in supernatant media. Lane 1: vector control and Lane 2: vector containing RHAMM I-2a insert; Lanes 3 and 4 are the vector control (Lane 3) and RHAMM I-2a containing insert (Lane 4) probed with the anti-RHAMM peptide antibody after pre-absorption with RHAMM fusion protein. RHAMM II did not accumulate in the supernatant media.

Figure 7:

FIG. 7 shows in-vitro translation. mRNA from 3T3 fibroblasts was translated with [$^{35}$S]-methionine\[$^{35}$S]-cysteine using the rabbit reticulocyte system. Immunoprecipitation was carried out using the RHAMM antibody R3.2. Lane 1: No mRNA; Lane 2: mRNA from 3T3 fibroblasts.

FIG. 8 shows primer extension analyses of RHAMM I AND RHAMM II.

Panel A: 5' terminus of the RHAMM I mRNA transcript.
Panel B: 5' termini of the RHAMM II mRNA transcripts.
Products of primer extension (right hand lane in each panel) were separated on 6% sequencing gels adjacent to sequencing reactions (lanes a, c, g and t) for sizing. Arrows indicate major 5' terminii.

Figure 9:

FIG. 9 shows Northern blot analysis of RHAMM expression in 3T3 fibroblasts.

FIG. 10 shows alternate 5' non-coding regions of the RHAMM I cDNA.

A: Nucleotide and deduced amino acid sequence of the 5' non-coding regions (SEQ ID NO:5 and SEQ ID NO:6)) and first coding exon of RHAMM IA and RHAMM IB, respectively. Stop codons in frame with the initiation codons are boxed. The point of divergence of the two sequences is indicated by a diagonal line.

B: Schematic representation of RHAMM IA and RHAMM IB respectively. Shaded boxes represent the protein coding regions; open boxes indicate the 5' and 3' untranslated regions which are identical. The hatched and shaded boxes indicate where the two 5' untranslated regions diverge. Single lines are introns.

FIGS. 11A and B show the nucleotide sequence of Intron 2 (SEQ ID NO:7)

FIG. 12 shows RHAMM I-2a stimulation of focal adhesion formation by immunofluorescent localization of vinculin after exogenous RHAMM I-2a treatment. C3 fibroblasts were incubated in the absence (A) or presence of 1 ng/mL (B), 10 ng/mL (C), 100 ng/mL (D) or 1 mg/mL (E) RHAMM I-2a-GST fusion protein for 2 hrs. before fixation and staining with anti-vinculin. The control (A) and 1 ng/mL (B) treated cells have only minimal staining with 75% of cells being vinculin plaque positive. However, with RHAMM I-2a addition there is an increased number of cells (<50% with 100 ng/mL) with focal adhesion staining (C–E). Mouse Igb control is shown (F).

FIG. 13 shows transfection of 10T½ cells with the RHAMM gene and RHAMM I-2a cDNA A) An 18 kb RHAMM insert in FIX phage was obtained by screening the genomic library with the RHAMM cDNA. This insert encoded intron 2, which contains promoter elements and alternative exons, to a segment of the 3' non-coding region present in exon 12. Aug 2 encodes the start site for RHAMM II isoform and 2A indicates the alternative exon.

B) The RHAMM I-2a cDNA (characterized in Table 2) was inserted into the pHβAPr-1Neo vector using Sal I and Hind III restriction sites in the cDNA. The β-actin promoter and the hyaluronan binding domains of the RHAMM cDNA are indicated as black boxes.

C) Western analysis of RHAMM protein in cell lysates obtained from genomic RHAMM transfected cells, G-12 (Lane 2) and from the vector control (Lane 1). Antibody staining revealed a major band of 66 kDa which was three fold higher in the RHAMM transfected cells.

D) Northern blot analysis of the clone G-12 and vector control of Panel C. The blot was probed with RHAMM cDNA and RHAMM transcript was shown to be overexpressed in G12 relative to the vector control. Expression of the housekeeping gene, GAPDH, indicated that equivalent amounts of RNA were loaded (probe: GAPDH cDNA).

Figure 14A:
Figure 14B:
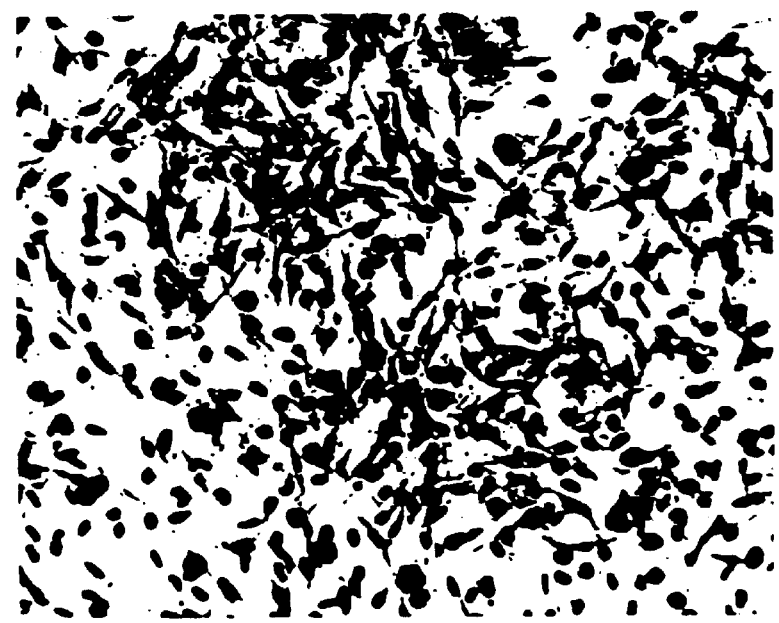

FIG. 14 shows that RHAMM transfected cells were morphologically transformed and overgrew at confluence.

A) Control 10T½ cells transfected only with the neomycin resistance gene appeared to be contact inhibited and were flattened in their morphology (x200).

B) 10T½ cells transfected with the RHAMM gene G12 were not contact inhibited, were less flattened than the vector controls, grew to a greater cell density and appeared morphologically transformed. Cultures were grown to confluence, fixed in formalin and stained with methylene blue. Identical results were obtained with cells transfected with RHAMM I-2a cDNA (×200).

Figure 15:
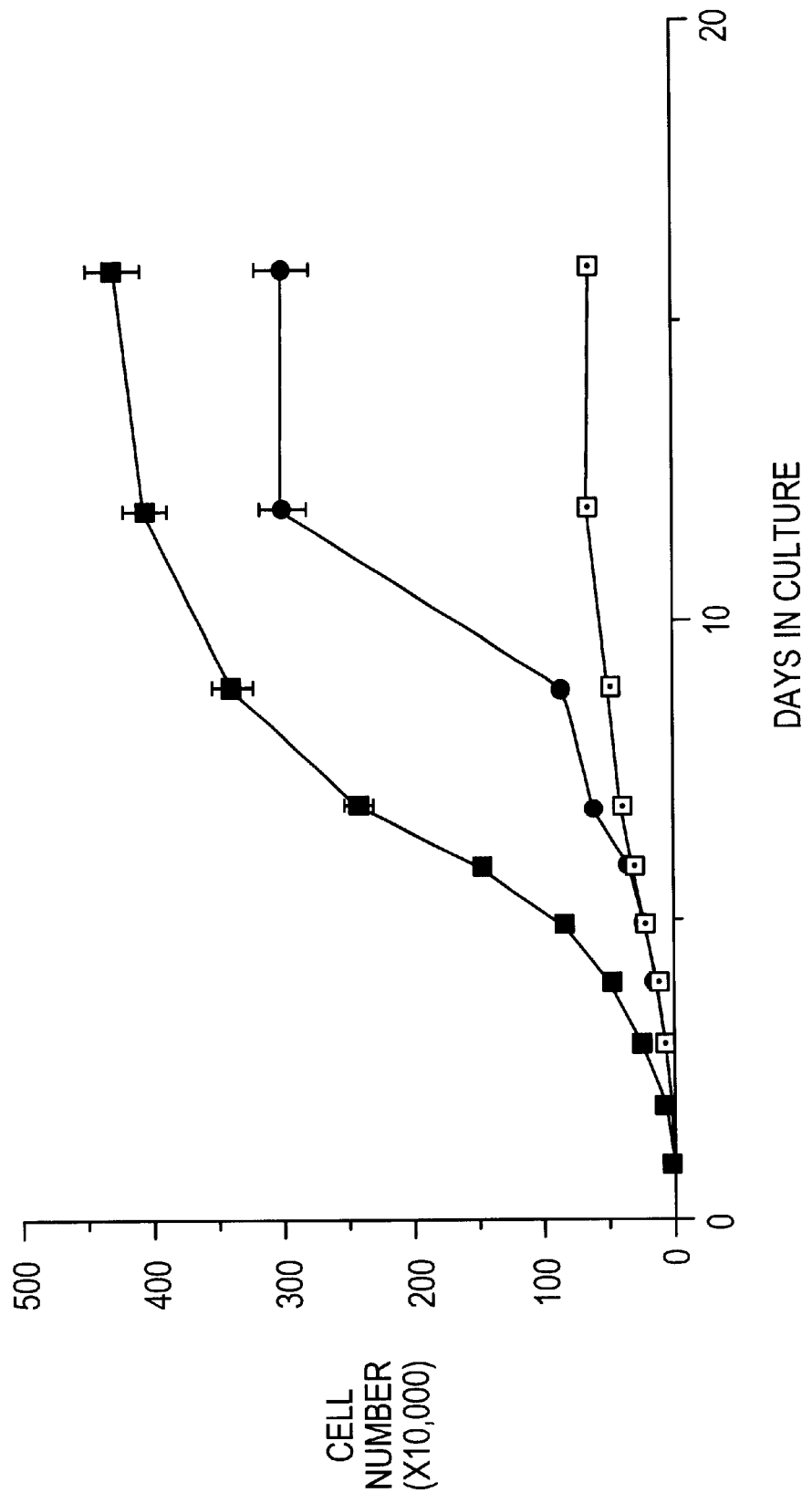

FIG. 15 shows cell number (×10,000) at confluence for vector transfected 10T½ cells (■), H-ras-transformed C3 cells (■) and genomic RHAMM transfected cell line G12 (♦). Identical results were obtained with clones overexpressing RHAMM I-2a cDNA.

FIG. 16 shows cultures of genomic RHAMM transfected G12 (G-10T½-12) or vector transfected 10T½ (vector), grown to confluence and then maintained for 3–4 weeks. The cultures were fixed in formalin and stained with methylene blue.

FIG. 17 shows histology of tumours resulting from injection of cells transfected with RHAMM gene. G12 cells were injected via the tail vein and animals were (a) sacrificed after 24 hr., lung tissue removed and explanted into G418-containing medium and tumour cell outgrowth monitored, or (b) animals were sacrificed after 6 weeks, lung tissue removed and processed for paraffin sections. Lungs exhibited multiple tumour nodules. Mice were also injected subcutaneously with either G12 or C3 cells. Three weeks later, G12 cells formed subcutaneous tumours that resembled the fibrosarcomas typical of c3 cells (c) whereas vector controls did not form tumours (d) (×150).

FIG. 18 shows (A) Strategy for mutating the hyaluronan binding domains (boxed) of RHAMM. Lysines (K) and arginines (R) were altered as indicated. (B) RH fusion protein was prepared from the intact cDNA (RHAMM fusion protein), electrophoresed and assayed for biotinylated HA binding in a transblot assay. Fusion protein produced from mutated RHAMM cDNA (Mutated RHAMM fusion protein) did not bind hyaluronan.

Figure 18A:
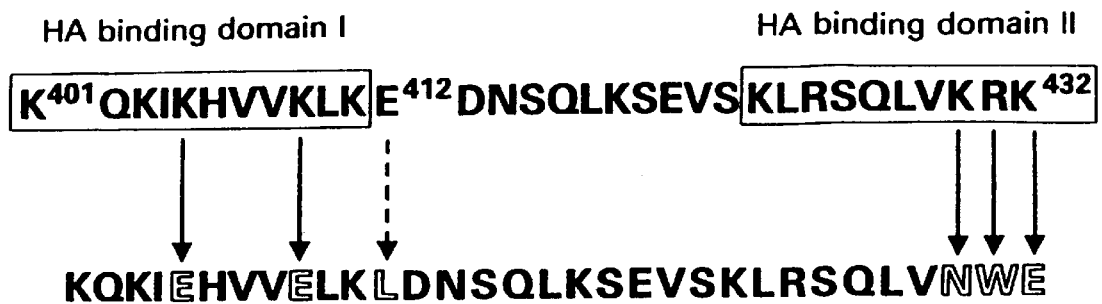
Figure 18B:

The $K^{401}$ to $K^{432}$ amino acid sequence of FIG. 18A is represented in SEQ ID NO:38. The amino acid sequence depicted below that sequence is represented as SEQ ID NO:39.

Figure 19:
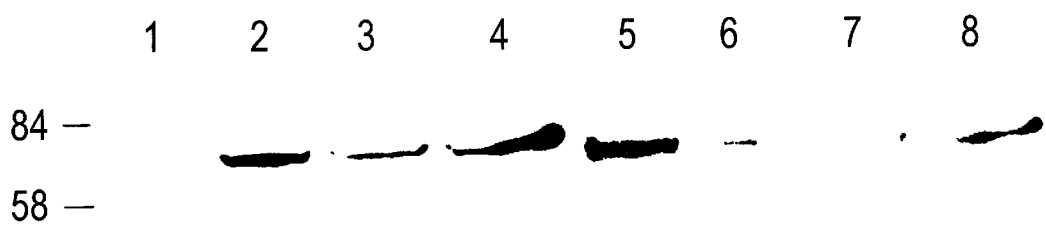

FIG. 19 shows (Lanes 1 to 4) Western transblot of C3 cell lysates prepared from cells transfected with empty vector (Lane 1) or mutated RHAMM cDNA (Lanes 2 to 4, which represent clones MRC3-4D, 5B, 5C) analysed for RHAMM. This blot was then stripped and reprobed with biotinylated HA (Lanes 5 to 8; Lane 5: empty vector and Lanes 6 to 8: MRC3 clones as above).

Figure 20:
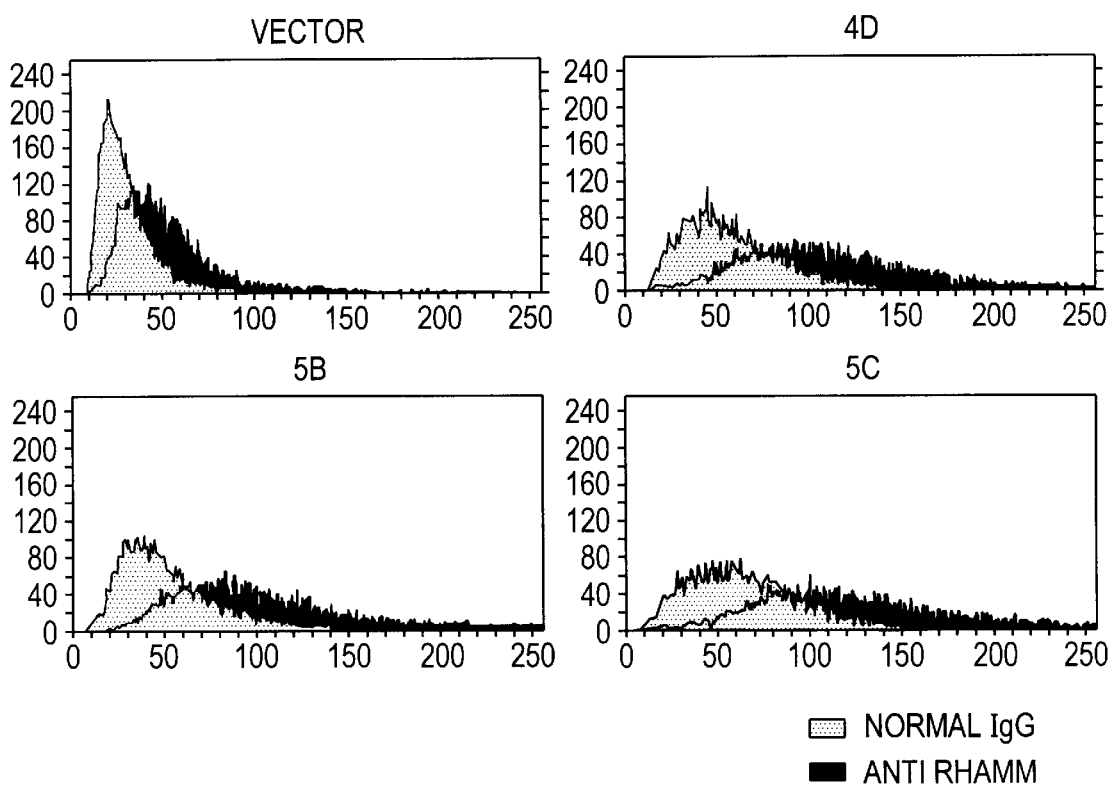

FIG. 20 shows total RHAMM expression on the cell membrane assessed by FACS; revealed major increases in MRC3 clones relative to the vector control.

Figure 21:
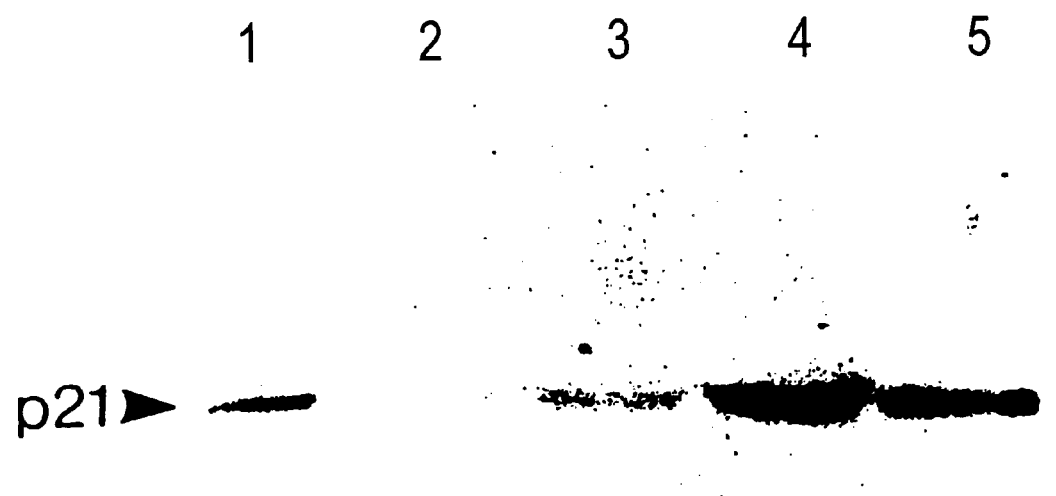

FIG. 21 shows Western transblot of cell lysates obtained from C3-vector controls (Lane 1), 10T½ fibroblasts (Lane 2) and the three MRC3 clones, 4D,-5B,-5C (Lanes 3 to 5 respectively), (p21™ visualised using a pan-specific anti-ras antibody).

Figure 22C:
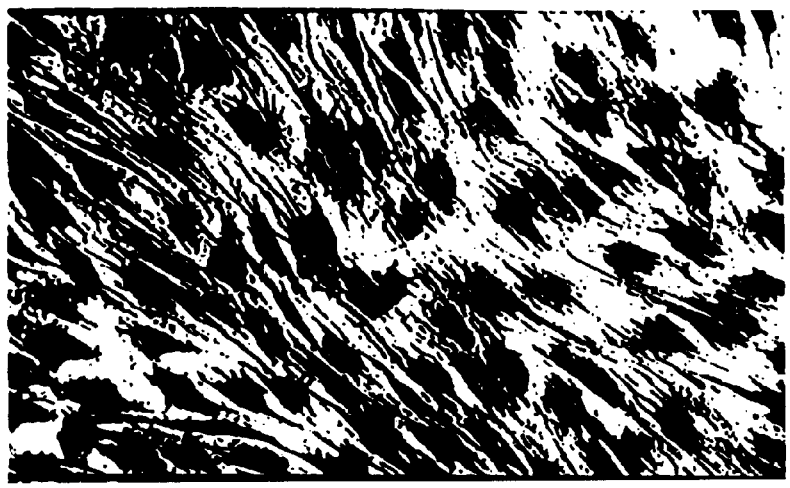
Figure 22B:
Figure 22A:
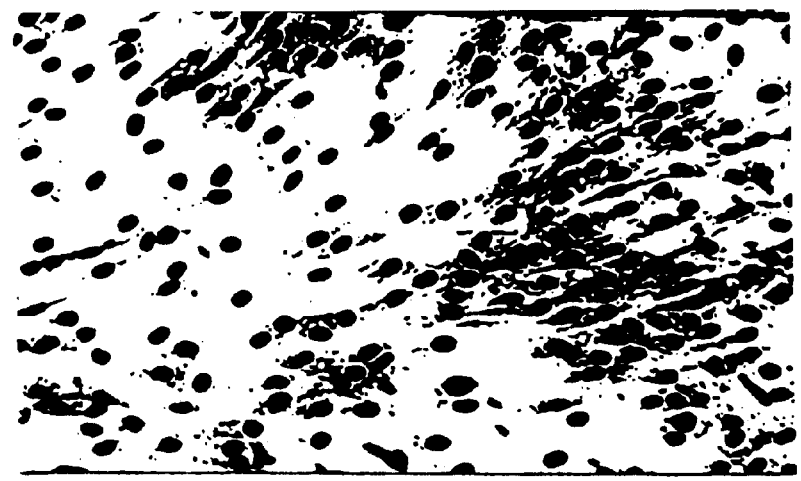

FIG. 22 shows cell morphology of transfected cell lines including 10T½ parent line(a), vector transfected C3 cells (b) and MRC3 transfected cells(c).

Figure 23:
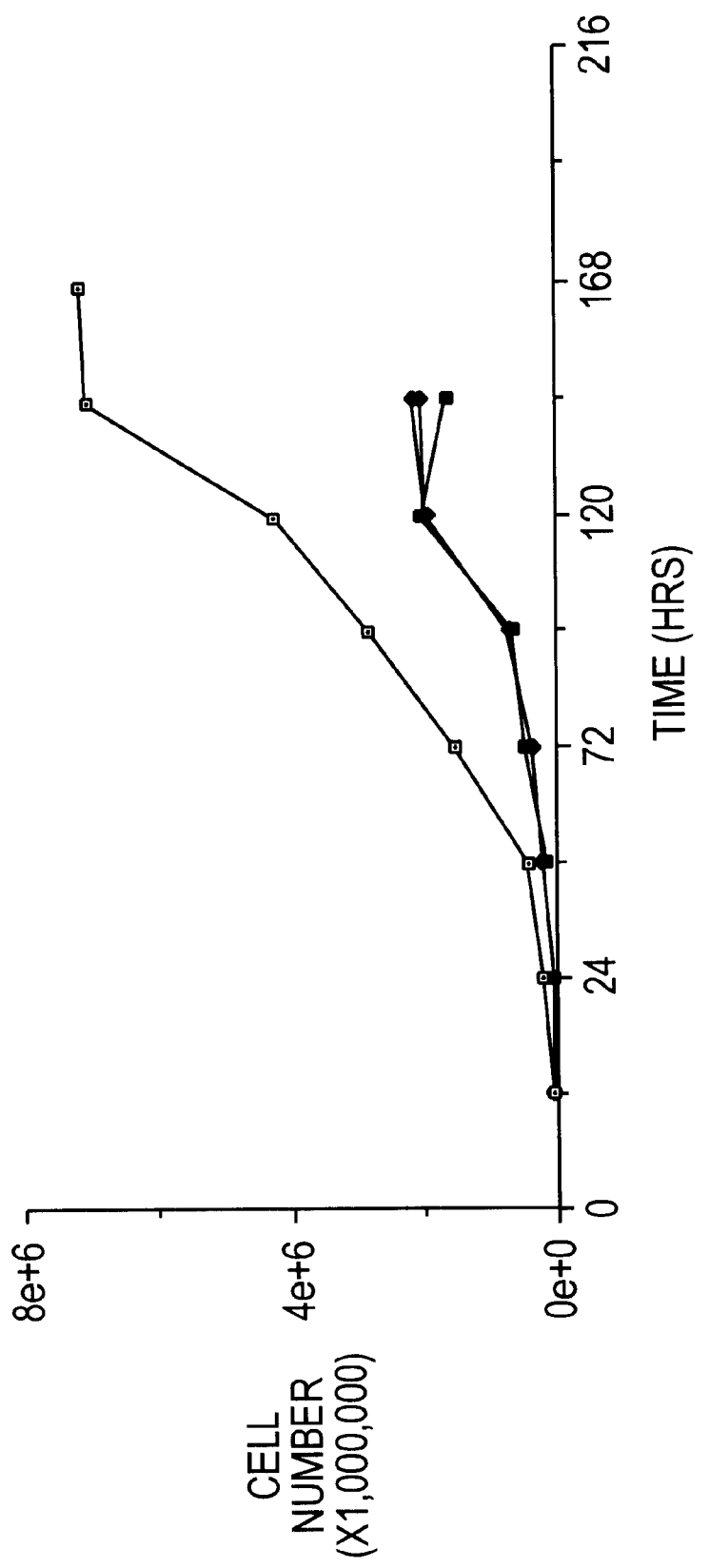

FIG. 23 shows growth curve of empty vector transfected C3 cells (■), MRC3-3D(♦), MRC3-5B(□), and MRC3-5C (◇) clones. 5×10$^4$ cells were plated and the number of cells was counted each day with a Coulter counter.

FIG. 24 shows a focus forming assay, using empty vector transfected C3 cells and MRC3-4D clone. The vector controls formed multiple foci in dense culture while the cells transfected with mutated RHAMM did not form foci.

FIG. 25 shows mice injected with either C3 parent line (1) or empty vector control (2) (large fibrosarcomas (arrows) were formed by 3 weeks after injection) and mice injected with MRC3-4D(3) or 5C(4) clones (no tumours after six months observation).

Figure 26:
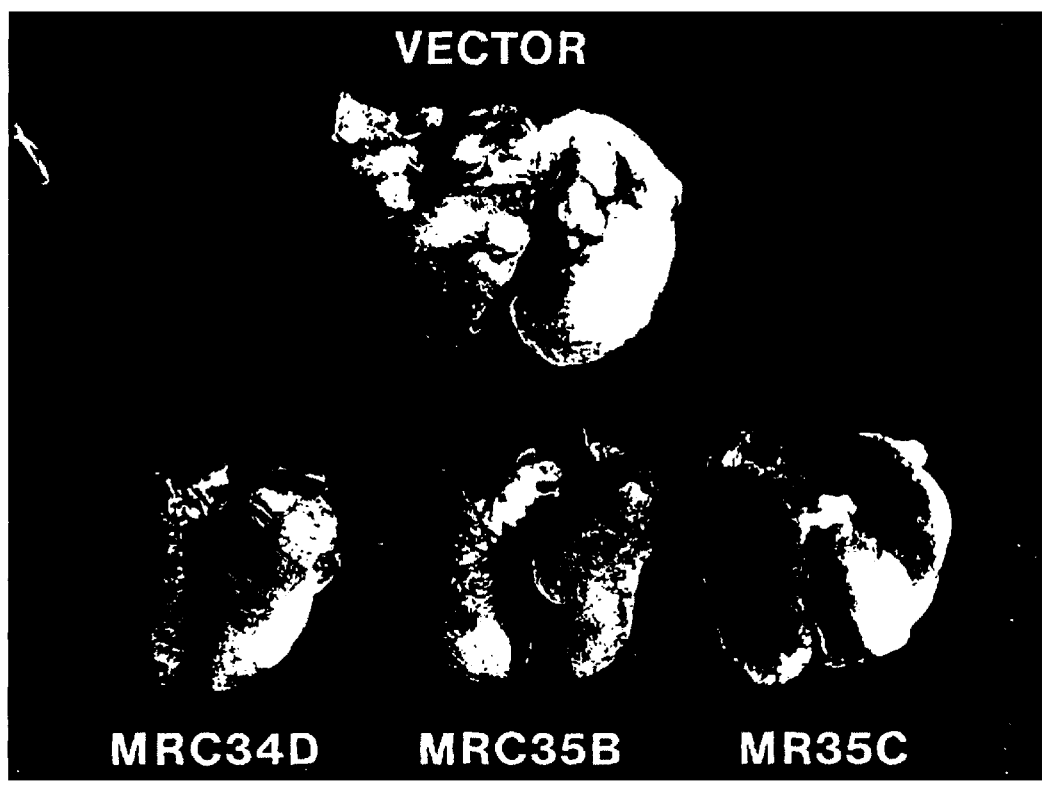

FIG. 26 shows lungs of mice injected by tail vein with empty vector C3 (upper panel) or clones MRC3-4D, 5B and 5C (lower panel).

Figure 27:
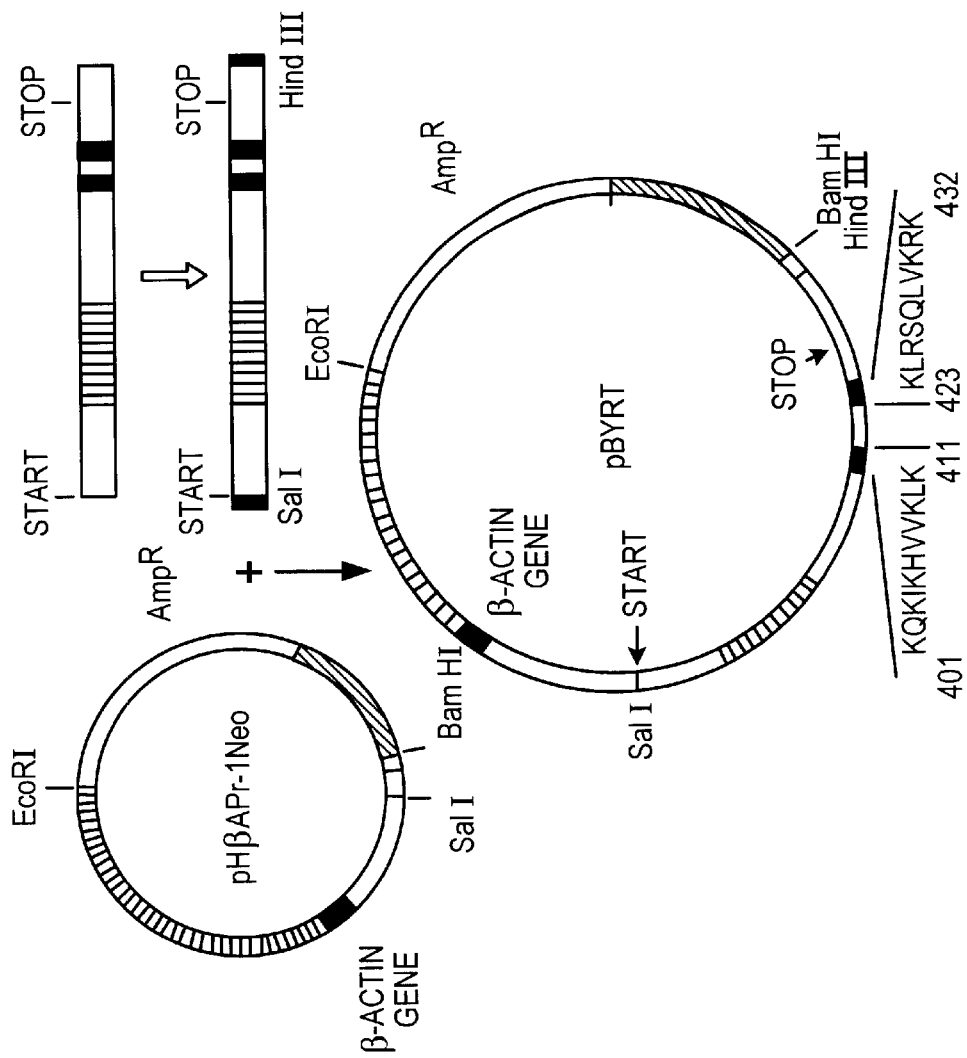

FIG. 27 shows insertion of the RHAMM II cDNA, whose sequence is common to all described RHAMM isoforms, in an antisense direction into the pHβAPr-1Neo plasmid. The cDNA insert was cut with Sal 1 and Bam H1 then inserted into the vector which contained a β-actin promoter and neomycin resistance gene.

The $K^{401}$ to $K^{411}$ amino acid sequence of FIG. 27 is represented by amino acids 1 to 11 of SEQ ID NO:38. The K to K432 amino acid sequence of FIG. 27 is represented by amino acids 23 to 32 of SEQ ID NO:38.

Figure 28A:
Figure 28B:
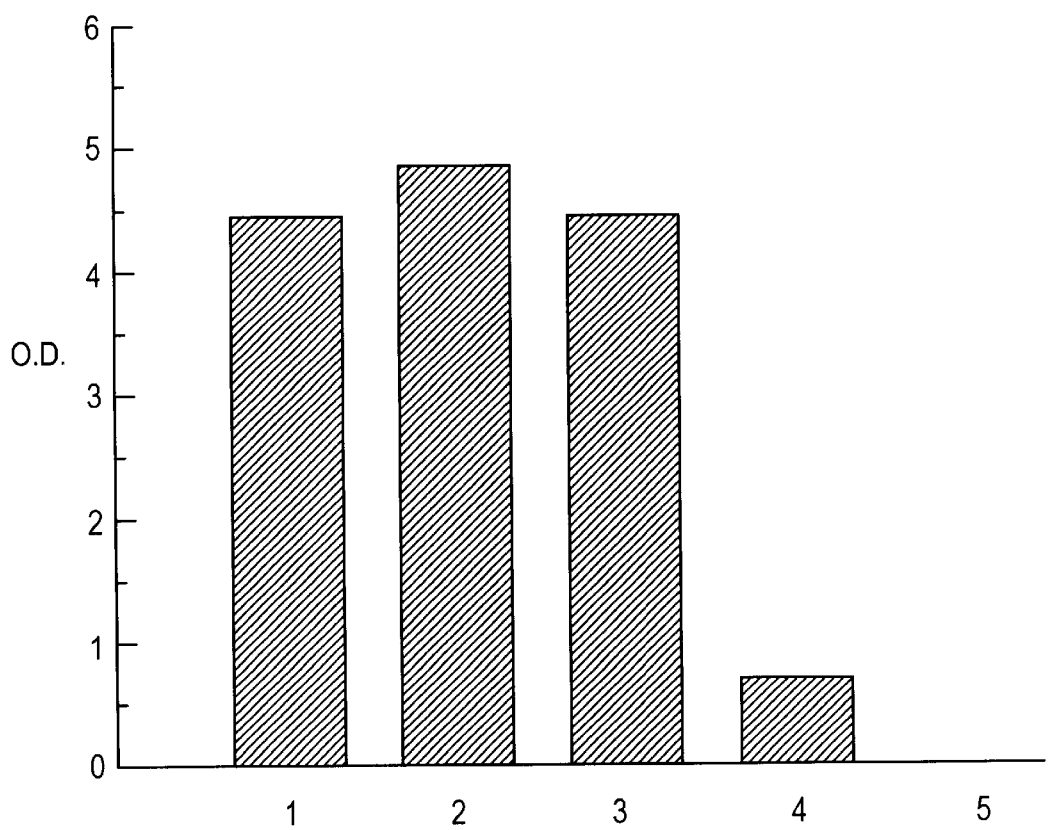

FIG. 28A shows a Western transblot of clones OR1 and OR2 (Lanes 4 and 5) showing an 86–100% decrease in RHAMM protein levels while 2 vector controls (Lanes 2 and 3) expressed a similar level of RHAMM to the 10T½ parental line (Lane 1). Antibody reactivity was specific to RHAMM since reactivity with the 70 kDa protein was ablated when the antibody was preincubated with excess RHAMM fusion protein (data not shown); and FIG. 28B shows densitometry of gel shown in 28A.

Figure 29A:
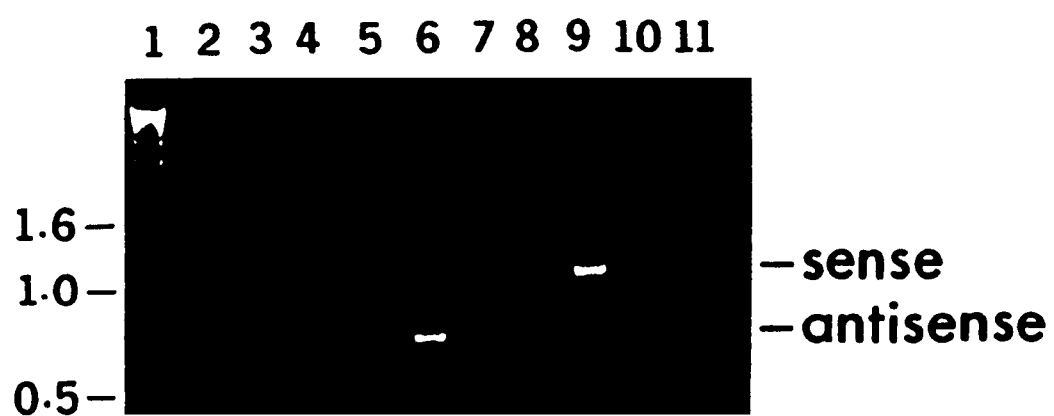

FIG. 29A shows agarose gel of RT-PCR inserts. RNA ladder is shown in Lane 1. RT-PCR was conducted using either sense primers (Lanes 2 and 8 to 11) or antisense primers (Lanes 3 and 4 to 7). RNA was isolated from 10T½ cells and digested with RNAse (Lanes 2 and 3) as controls. Antisense RNA was only detected in the two antisense transfected OR1, OR2 clones (Lanes 6 and 7) and not in the 10T½ or vector control (Lane 5). Sense RHAMM RNA was detected in all of the controls (10T½ parent: Lane 8; vector control; Lane 9) and clones OR1 and OR2 (Lanes 10, 11). No attempt was made to make RT-PCR quantitative.

Figure 29B:
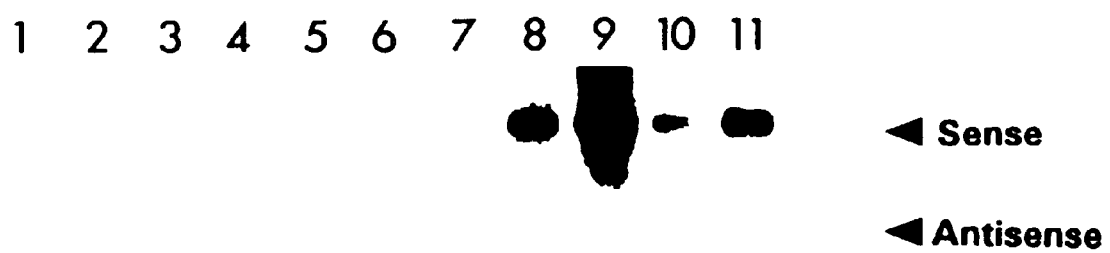

FIG. 29B shows Southern analysis of the agarose gel in FIG. 20A. Hybridization of the sense and antisense RNA with the RT-PCR inserts described above confirmed that the inserts were RHAMM. Lanes are the same in 29A.

FIG. 30 shows inhibition of transformation by mutant H-ras in fibroblasts expressing antisense RHAMM, clones OR1 and OR2; A) 10T½ parent cells transfected with ras; B) Transfection of vector control 10T½ cells with ras; C) OR1 clone transfected with ras; and D) OR2 clone transfected with ras. Ras vector transfection resulted in formation of multiple large foci formed in 10T½ cells but clones transfected with RHAMM antisense did not form foci.

Figure 31:
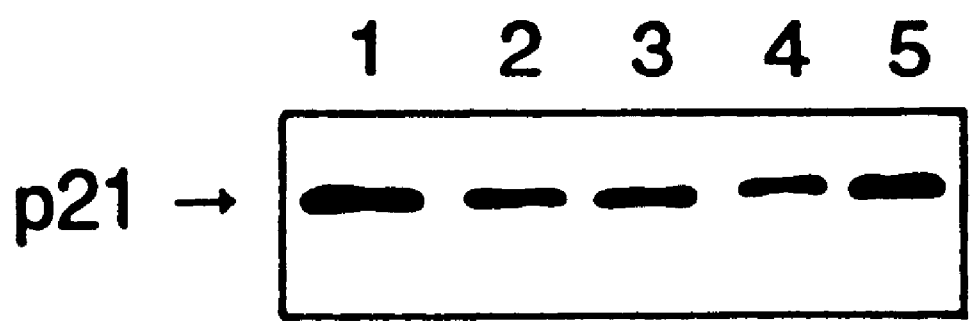

FIG. 31 shows Ras protein expression in ras-transfected C3 cells: Lane 1; antisense vector only 10T½ clone: Lane 2; antisense vector only 10T½ clone 2: Lane 3; OR1-cells: Lane 4; OR2-cells: Lane 5). p21 ras protein was detected in a Western assay with a pan-ras antibody. Levels of expression (Lanes 2–5) are approximately equivalent and are higher than normally expressed in parental 10T½ cells (see FIG. 21).

Figure 32:
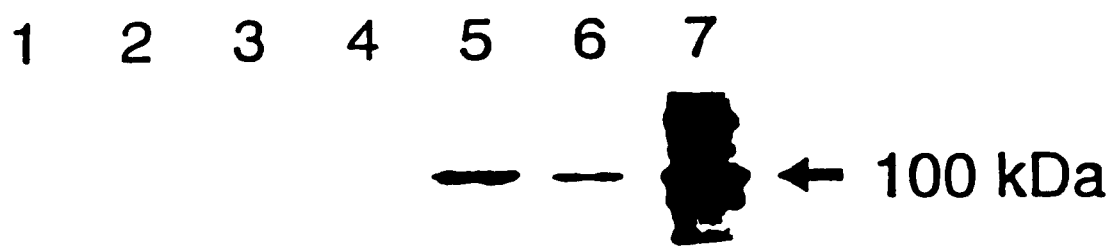

FIG. 32 shows a contact photograph of a gel resulting from a pulse chase study of RHAM production by C3 fibroblasts.

Lanes 2 to 6 show labelling of 35 S-RHAMM after chase period of 0, 5, 10, 15 and 30 minutes respectively;

Lane 1 was IgG control after 20 min;

Lane 7 shows immunoprecipitation of whole cell lysate.

Figure 33:
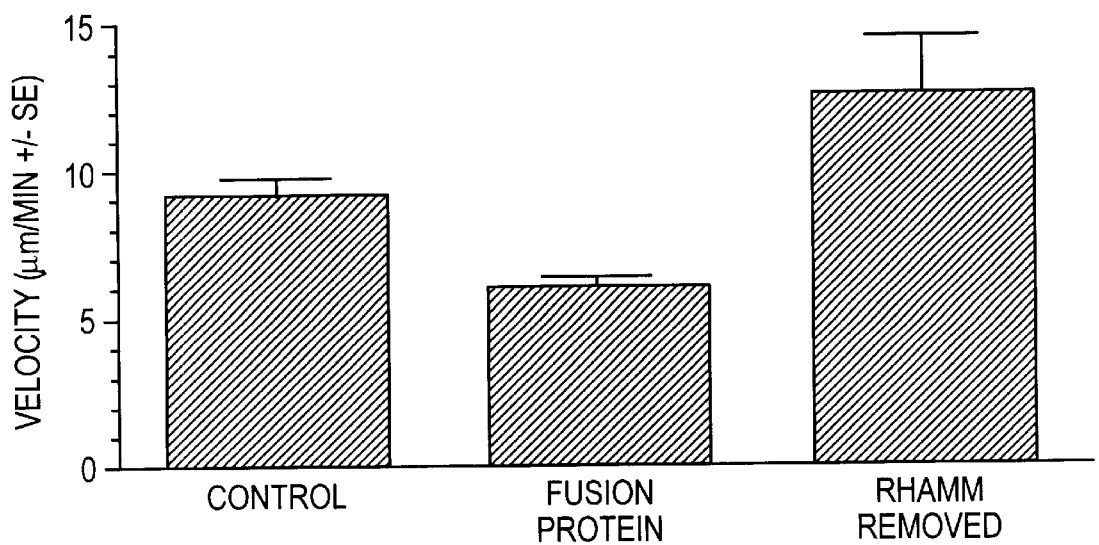

FIG. 33 shows C3 fibroblast locomotion (expressed as velocity in μm/min) in the presence of spent growth medium from C3 fibroblasts (control), RHAMM fusion protein (1 ng/ml) or spent growth medium after RHAMM removal.

Figure 34:
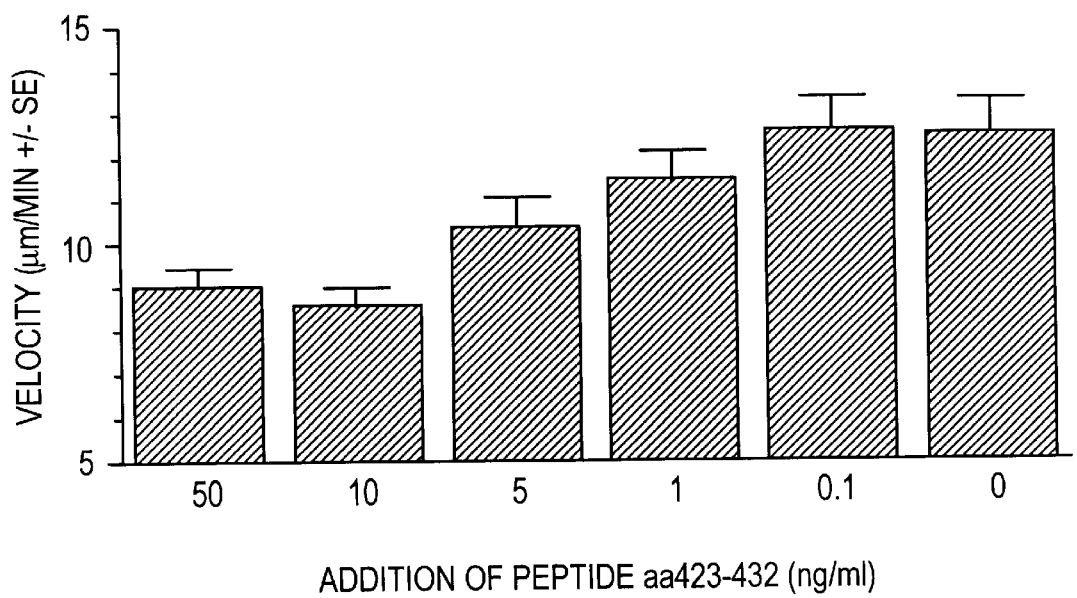

FIG. 34 shows effect of various concentrations of peptide$^{aa423-432}$ on locomotion (expressed as velocity in μm/min) of C3 fibroblasts. Values represent mean±SEM for 60 cells.

FIG. 35 shows in Panel A: a schematic representation of the strategy for deleting the HA-binding-domain II (peptide$^{aa423-432}$) and mutating the HA-binding-domain I ($K^{405}$ and $K^{409}$ altered to $E^{405}$ and $E^{409}$) of RHAMM-GST fusion protein to obliterate HA binding activity; Panel B: a blot of purified native RHAMM-GST fusion protein (lanes 3, 5 and 7) and purified HA-binding-domain deleted/ mutated RHAMM-GST fusion protein (lanes 2, 4 and 6). Lanes 2 and 3 show visualisation with Coomassie Blue, lanes 4 and 5 by binding to anti-RHAMM antibody and lanes 6 and 7 by binding to biotinylated HA. Lane 1 shows molecular weight markers.

Figure 36A:
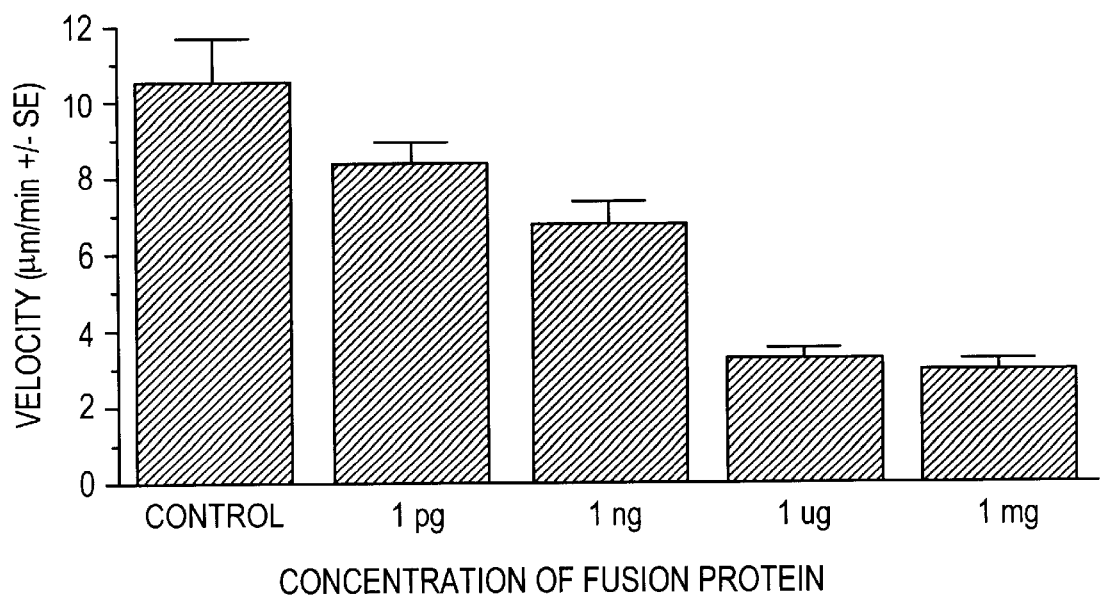

FIG. 36A shows the effect of various concentrations of RHAMM-GST fusion protein on locomotion (expressed as velocity in μm/min) of C3 fibroblasts. Values represent mean±SEM for 60 cells.

Figure 36B:
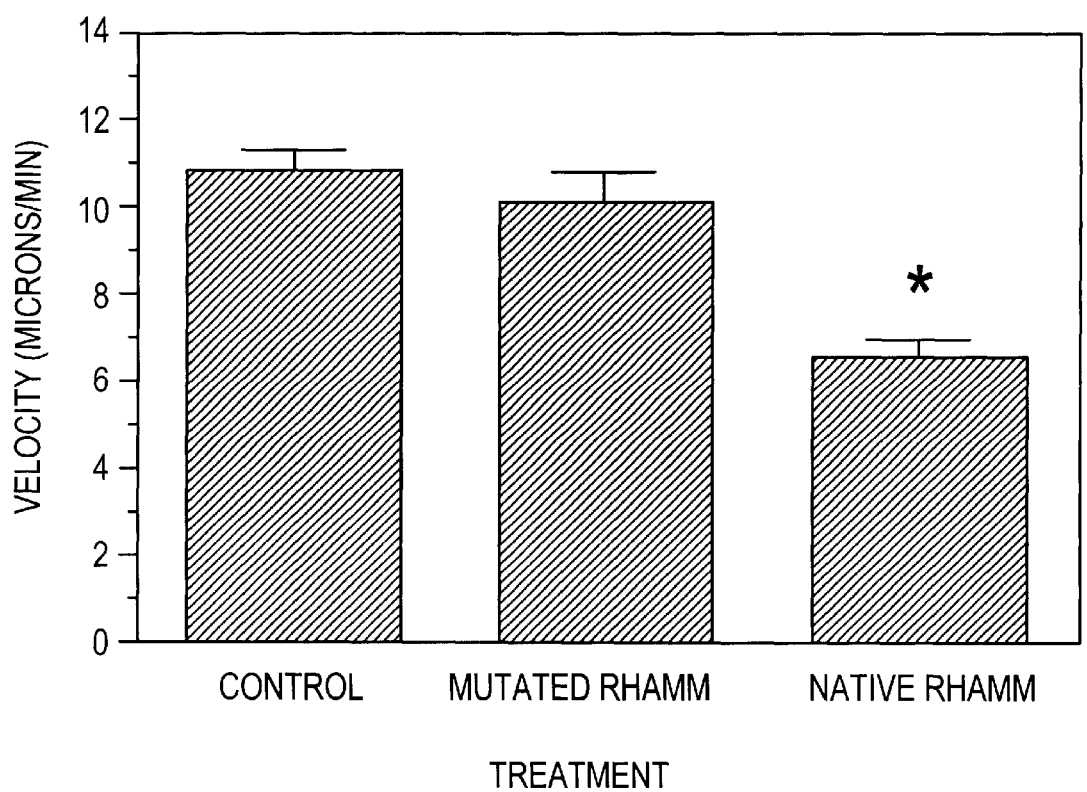

FIG. 36B shows C3 fibroblast locomotion (expressed as velocity in μm/min) in presence of RHAMM-GST fusion protein (native RHAMM), HA-binding-domain deleted/ mutated RHAMM-GST fusion protein (mutated RHAMM) and with no addition (control).

Figure 37A:
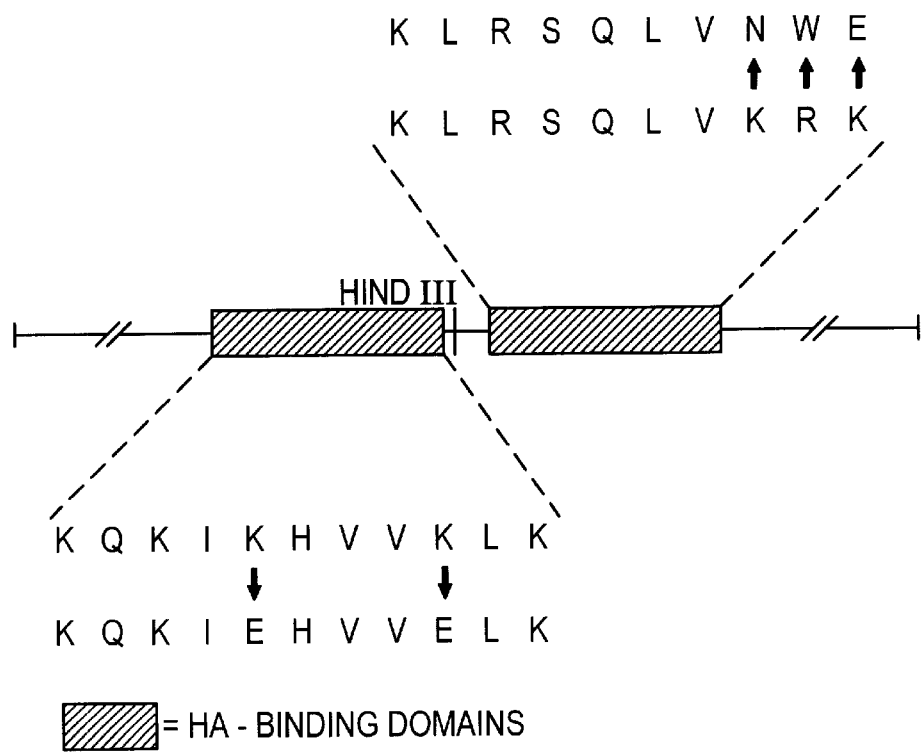

FIG. 37A shows a schematic representation of the strategy for directing point mutations to the second HA binding domain of RHAMM.

Figure 37B:
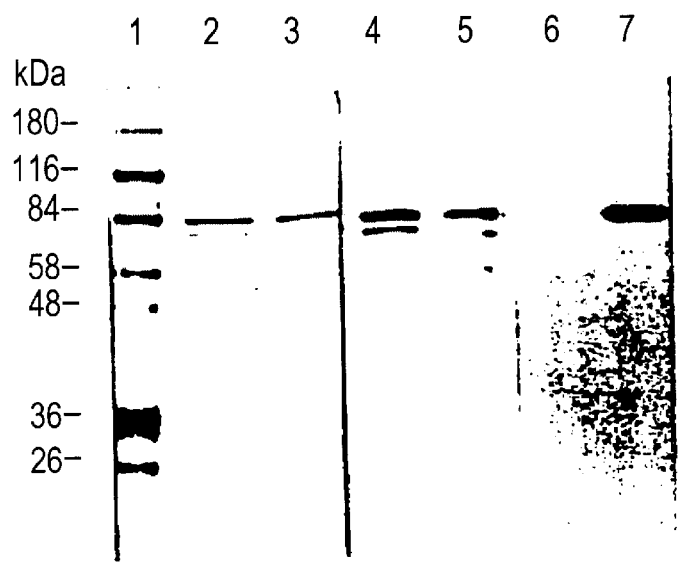

FIG. 37B shows a blot of purified native RHAMM-GST fusion protein and purified HA-binding-domain point mutated RHAMM-GST fusion protein. Blot visualized as described for FIG. 35, panel B.

Figure 37C:
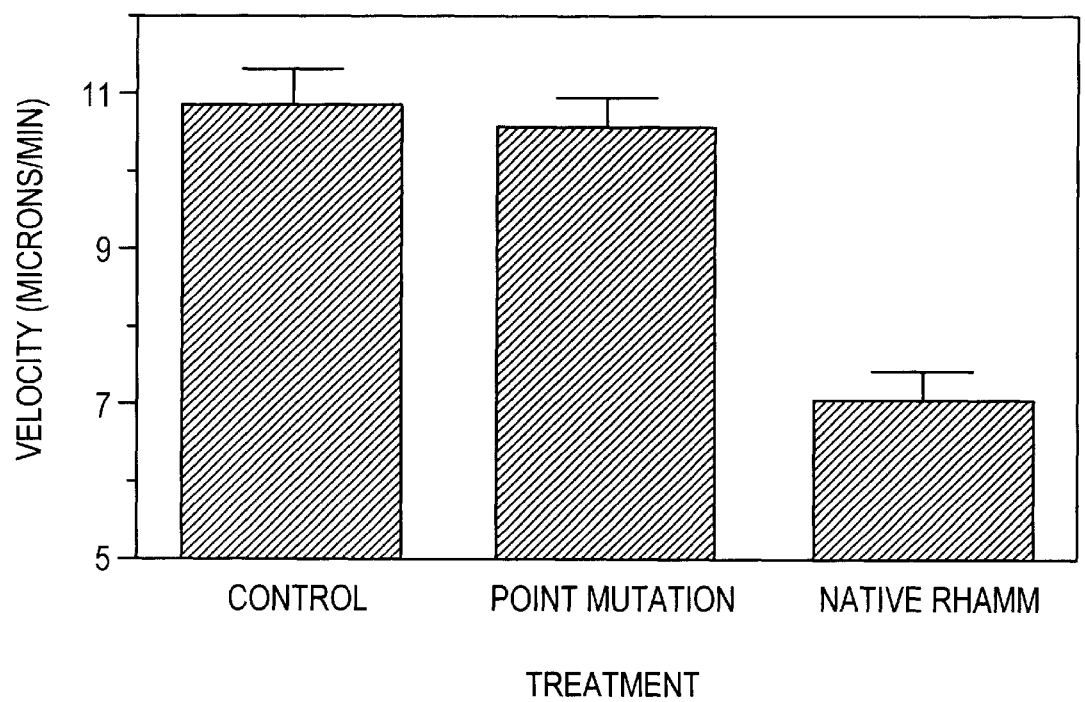

FIG. 37C shows C3 fibroblast locomotion (expressed as velocity in μm/min) in presence of RHAMM-GST fusion protein (native RHAMM), HA-binding domain point mutated RHAMM-GST fusion protein (point mutation) and no addition (control).

The top two amino acid sequences in FIG. 37A are represented by amino acids 23 to 32 of SEQ ID NO:39 and amino acids 23 to 32 of SEQ ID NO:38, respectively. The bottom two amino acid sequences in FIG. 37A are represented by amino acids 1 to 11 of SEQ ID NO:38 and amino acids 1 to 11 of SEQ ID NO:39, respectively.

Figure 38:
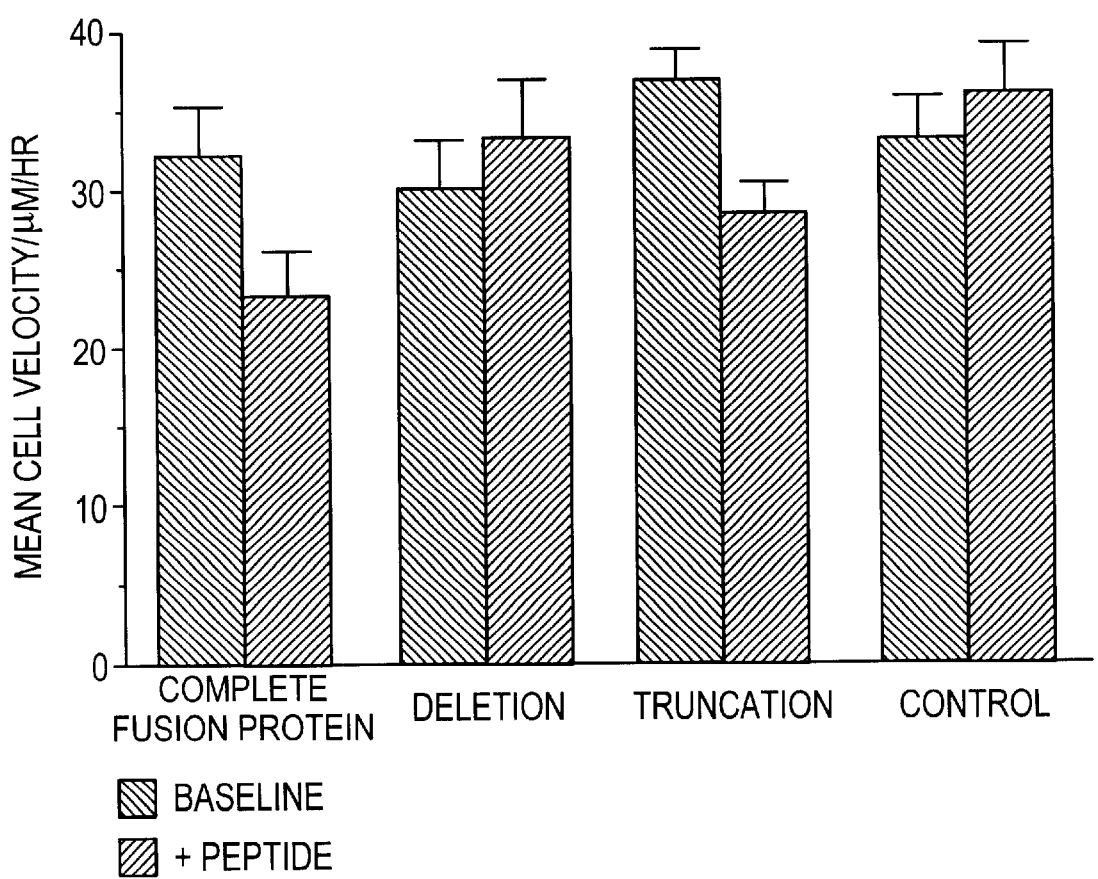

FIG. 38 shows a comparison of control C3 fibroblast locomotion (solid bars) with locomotion in the presence of various forms of RHAMM protein (hatched bars).

Figure 35A:
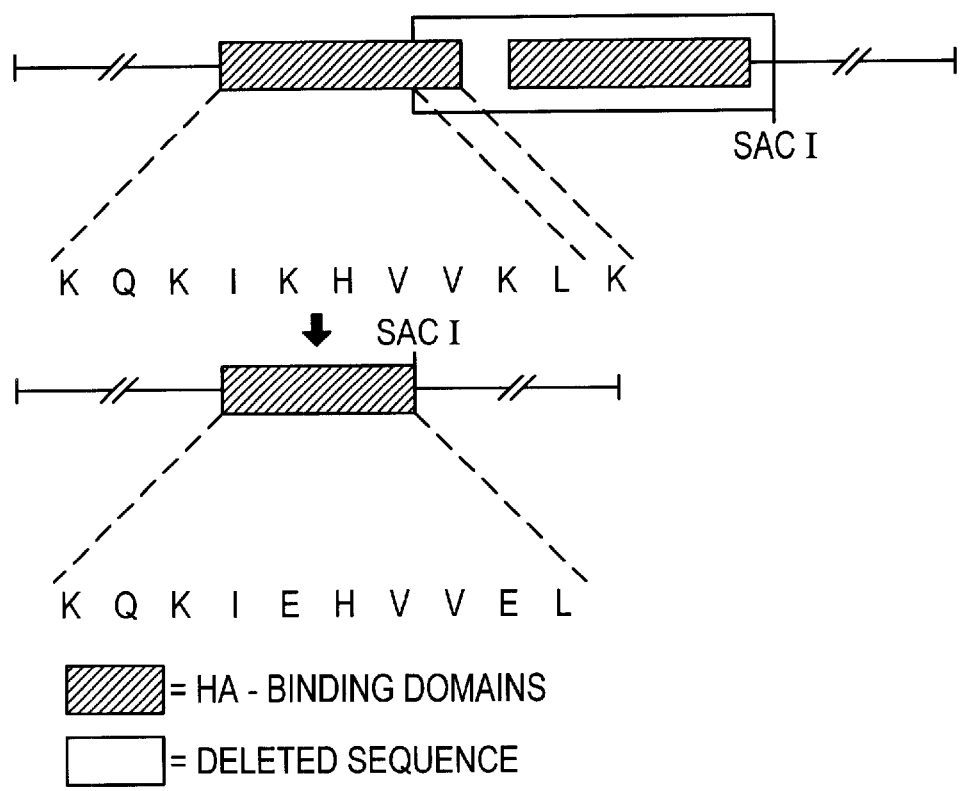

Complete fusion protein=RHAMM-GST fusion protein;

Deletion=RHAMM-GST fusion protein with deletions/ alterations as in FIG. 35A;

Truncation=RHAMM-GST fusion protein truncated from aa 435–aa 570.

Control=GST-bovine serum albumin fusion protein.

FIG. 39 shows morphology of cultured human breast cancer cell lines. Pictures were taken by using timelapse cinemicrography system with Sony video printer under contrast filed illumination. A. MDA-MB-231, B. MCF-7, C.

MDA-MB-468, D.ZR-75-1, E. T-47-D, F. Hs-578-T (original magnification ×100).

Figure 40A:
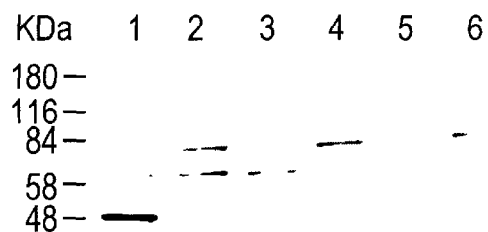

FIG. 40 shows in Panel A: Immunoblot analysis of RHAMM in human breast cancer cell lines. Equal protein concentration from cell lysates were electrophoresed on SDS-PAGE and transferred to nitrocellulose membranes. Membranes were probed with an antibody to RHAMM ($aa^{269-288}$) Three major protein bands, 77, 64 and 52 KDa, were detected in all six human breast cancer cell lines (Lane 1. MDA-MB-231; 2-MCF-7; 3. MDA-MB-468; 4. ZR-75-1, 5. T-47-D, 6. Hs-578-T. Panel B: Densitometric analysis of the protein bands of A. Panel C: Densitometric analysis of total RHAMM expression.

Figure 41:
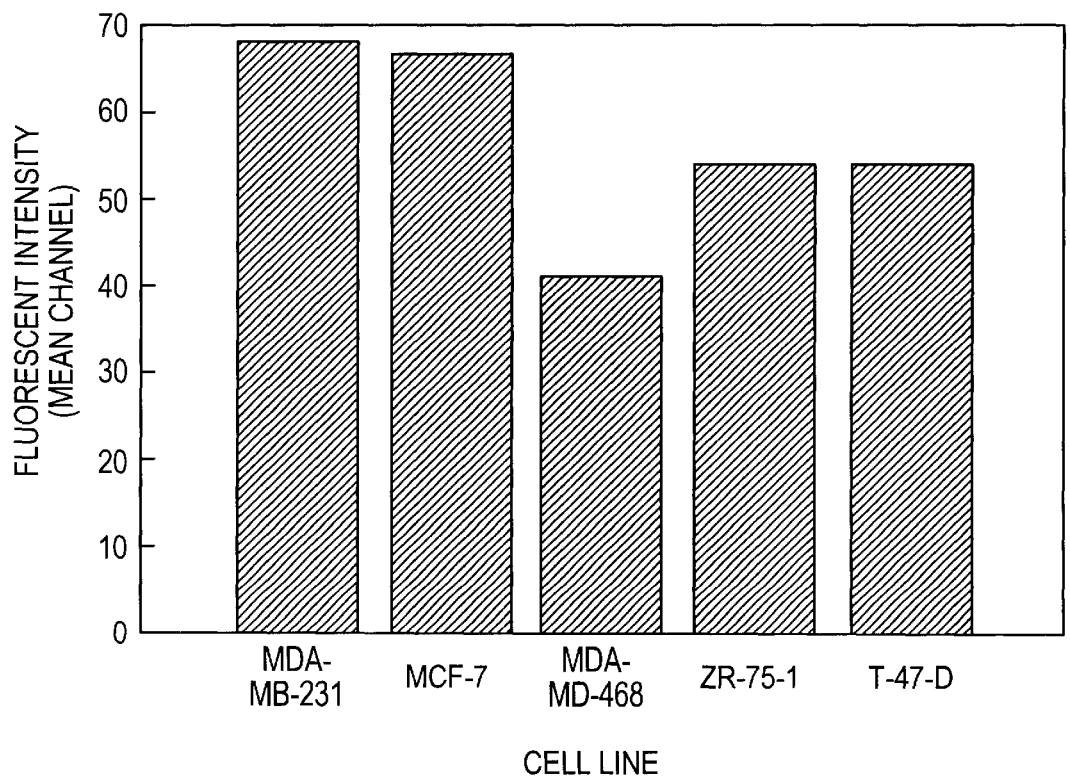

FIG. 41 shows RHAMM expression on cell surface of human breast cancer cell lines as demonstrated by flow cytometry analysis (FACS). Cells were stained with antibody to RHAMM ($aa^{269-288}$) or rabbit IgG and analysed on a EPICS Coulter Counter. Fluorescence intensity indicated here is the mean channel number of antibody to RHAMM staining minus rabbit IgG staining.

Figure 42A:
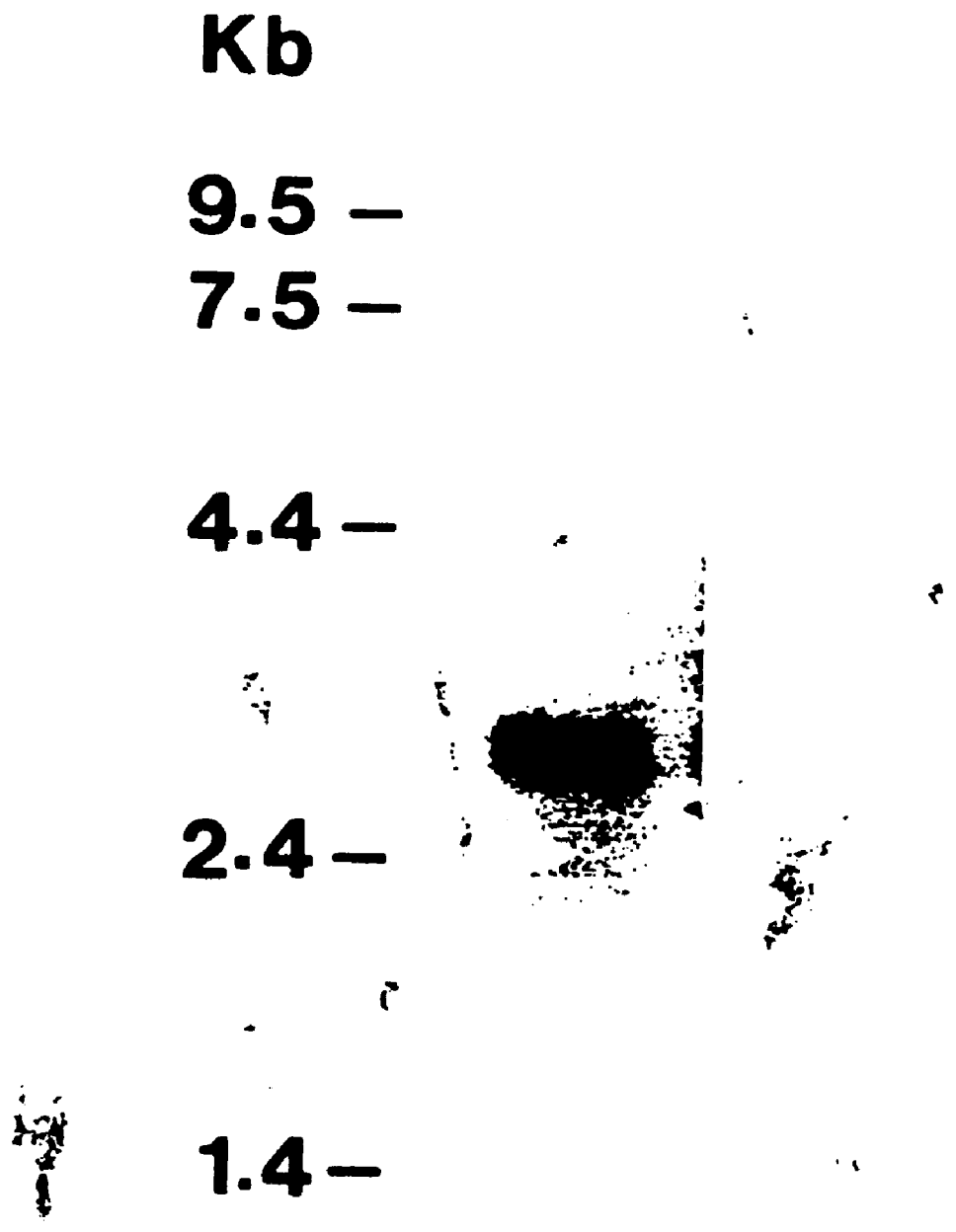

FIG. 42 shows (A) Northern blot analysis showing a 3.1 kb transcript of RHAMM in MDA-MB-231. (B) RT-PCR products electrophoresis. Lane 1.100 bp DNA marker, 2. human B-actin positive control, 3. MDA-MB-231, 4. MCF-7, 5. MDA-MB-468, 6. ZR-75-1, 7. T-47-D, 8. MDA-MB-231 RNA treated with RNAase. (C) Amino acid sequence of RT-PCR product from total RNA of human breast cancer cells (MDA-MB-231) compared to that of mouse RHAMM. The amino acid sequence of the human product is represented in SEQ ID NO:40. The amino acid sequence of the mouse product is represented in SEQ IN NO:41.

Figure 43:
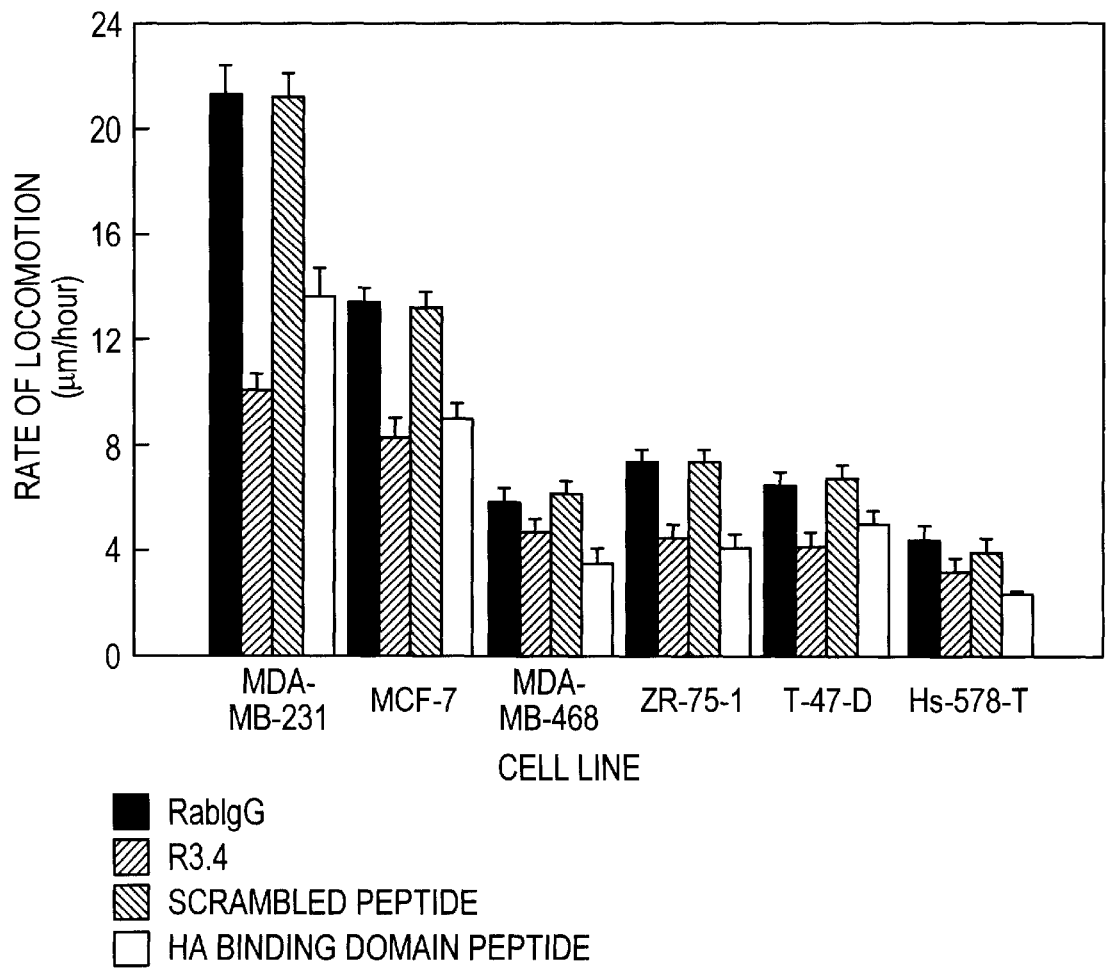

FIG. 43 shows cell locomotion and effect of presence of anti-RHAMM antibody and RHAMM peptide. Cell locomotion was recorded by using a computerized timelapse image analysis system. Anti-RHAMM ($aa^{269-288}$) antibody (5 μg/ml), control rabbit IgG (5 μg/ml), a synthetic peptide, mimicking HA binding domain I ($aa^{401-411}$) (2 μg/ml) and a scrambled peptide, consisting of the same amino acids arranged in a random manner (2 μg/ml) were examined for their effect on cell locomotion.

FIG. 44 shows invasion of cell lines into vitrogen (A), and effect of antibodies to RHAMM on invasion (B) The percentage of cells occurring below the surface of gels was calculated relative to the total cell number observed in 5 microscopic fields. For antibody effects, anti-RHAMM ($aa^{269-288}$) antibody, R3 or anti-RHAMM fusion protein antibody were used.

Figure 45:
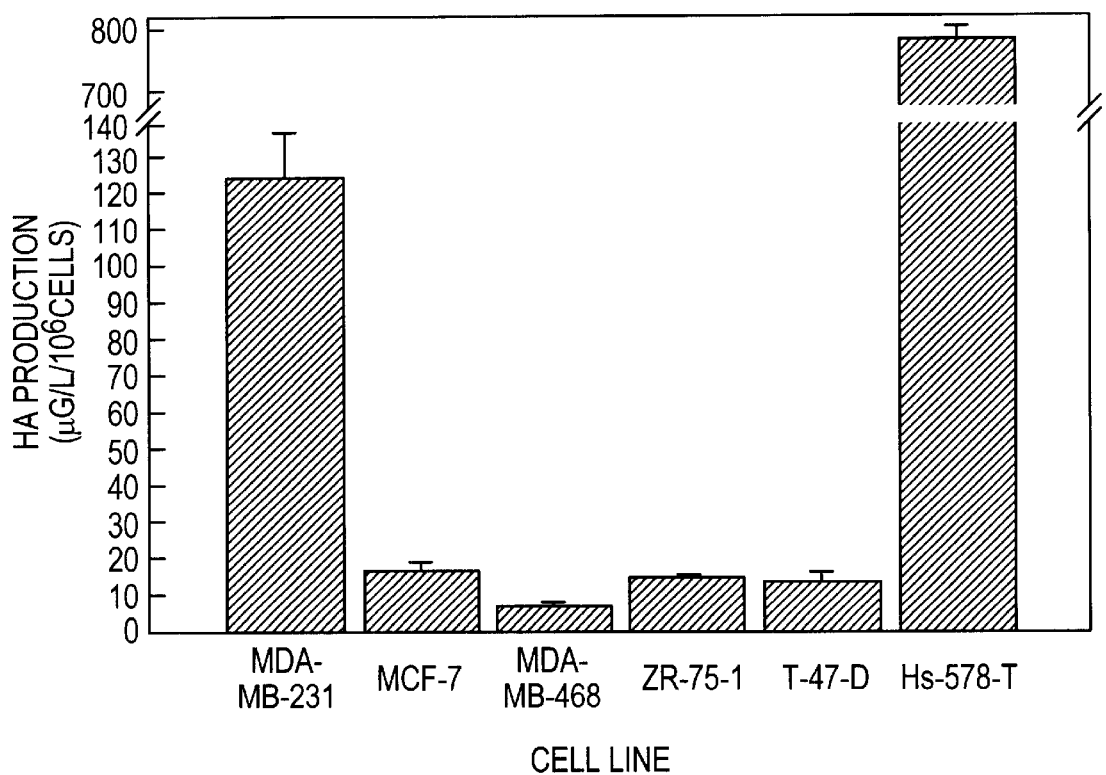

FIG. 45 shows HA production of cultured human breast cancer cell lines. HA concentration in the media was measured with a Pharmacia HA test kit 50, then normalized for cell number (I.E. μg/L/$10^6$ cells).

FIG. 46 shows imunocytochemistry of human breast cancer tissue for RHAMM. A. normal breast tissue from reduction mammoplasty, B. breast benign tumour (adenoma), C. breast malignant tumour (adenocarcinoma), and D. breast malignant tumour (adenocarcinoma) negative control (original magnification, ×400).

Figure 47A:
Figure 47B:
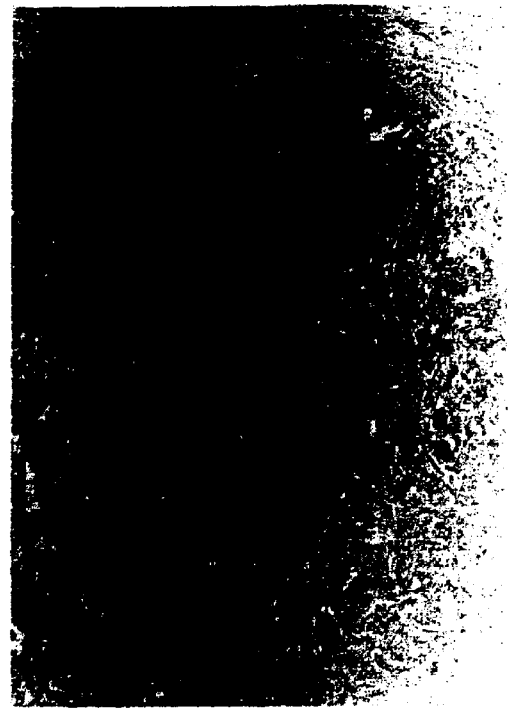

FIG. 47 shows immunocytochemistry of human breast cancer tissues for RHAMM. A. primary breast malignant tumour (adenocarcinoma), and B. lymph node metastasis of breast malignant tumour (adenocarcinoma) (original magnification, ×100).

Figure 48:
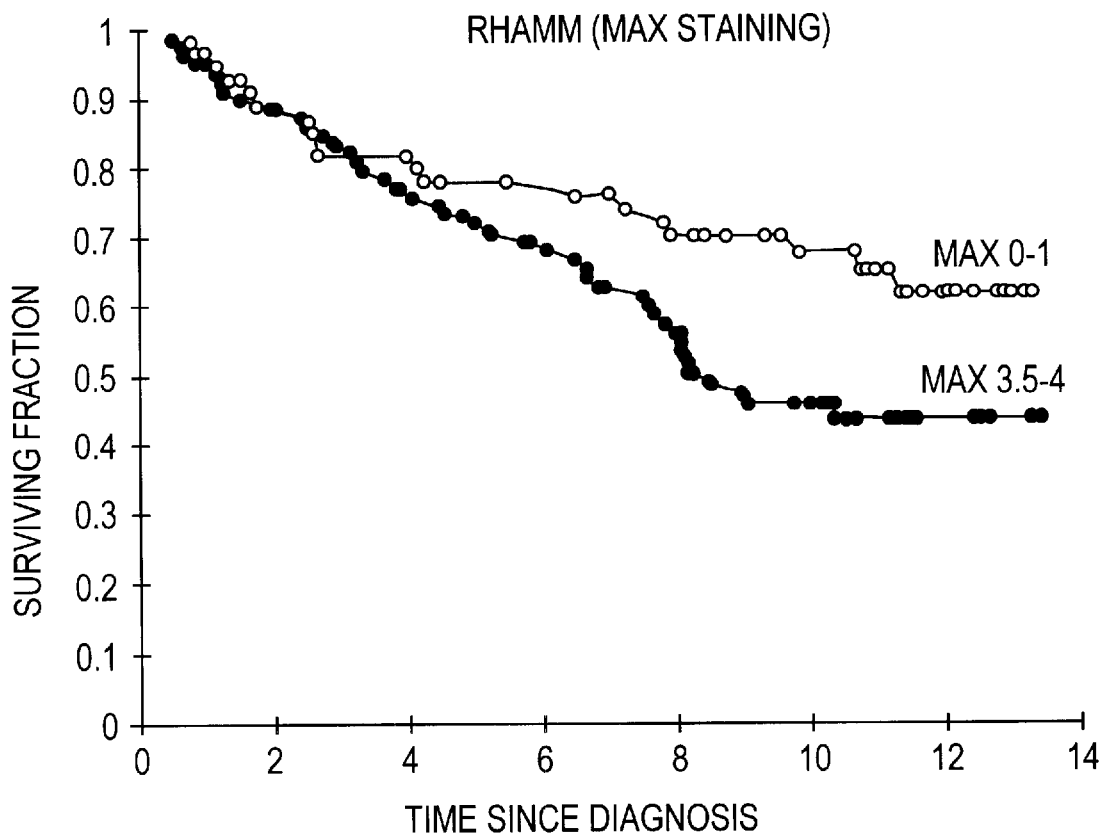

FIG. 48 shows survival of breast cancer patients over 14 years from diagnosis. (○) Patients with maximum RHAMM level of 0–1 in tumour (expressed as maximum density of staining); (●) patients with maximum RHAMM level of 3.5–4 in tumour (expressed as maximum density of staining).

FIG. 49 shows immunocytochemical localization of RHAMM in rat carotid arteries after balloon catheter injury to the endothelium, using antiserum raised in rabbits against sequence $aa^{268-288}$ of RHAMM [anti-peptide $aa^{268-288}$] (magnification: A–D: 630×; E & F: 400 x). Uninjured artery is represented in (A) and injured arteries were harvested at 2 hours (B), 6 hours (C), 48 hours (D), 7 days (E) and 14 days (F) after injury. Solid arrows indicate the internal elastic lamina and L represents the vessel lumen. Constitutive RHAMM expression was seen in the endothelial and medial layers of uninjured arteries. Two hours after removal of the endothelium, macrophages and neutrophils adherent to injured site expressed high levels of RHAMM. At 6 hours, a small proportion of smooth muscle cells within the medial layer showed increased expression of RHAMM. By 48 hours, smooth muscle cells adjacent to the internal elastic lamina demonstrated a phenotype distinct from those in the medial layer and also expressed high levels of RHAMM. From 7 to 14 days after injury, a neointimal layer increasingly narrowed the affected artery and demonstrated continued elevated RHAMM expression.

Figure 49A:
Figure 49B:
Figure 49C:
Figure 49D:
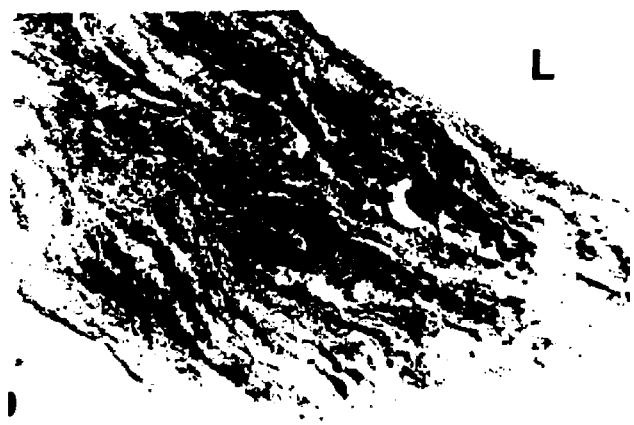
Figure 49E:
Figure 49F:
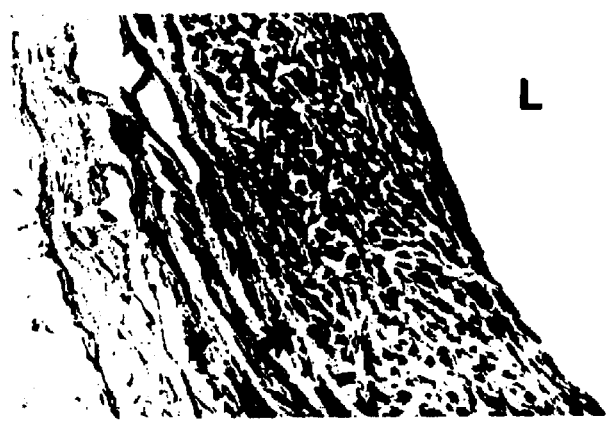
Figure 50:
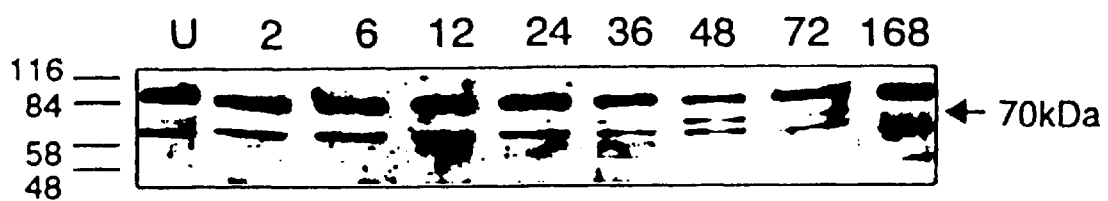

FIG. 50 shows immunoblot of rat carotid arteries following balloon catheter injury to the endothelium. Proteins extracted from uninjured (U) and from arteries between 2 and 168 hours after injury were separated by 10% SDS-PAGE. Antiserum against peptide $aa^{268-288}$ encoded in the RHAMM cDNA was used to identify RHAMM isoforms. Constitutive expression of 84 kDa and 65 kDa isoforms of RHAMM was noted in uninjured arteries. The expression of the 84 kDa isoform declined between 36 and 48 hours after which expression again increased up to to 168 hours. Expression of the 65 kDa isoform did not show significant changes following injury. Between 36 and 72 hours after balloon catheter removal of the endothelium, a 70 kDa isoform of RHAMM appeared, coincident with maximal RHAMM expression in smooth muscle cells migrating to form the neointima as seen in FIG. 49.

FIG. 51 shows immunohistochemical localization of hyaluronan (HA) in rat carotid arteries following balloon catheter injury to the endothelium using biotinylated aggrecan as a probe (magnification: A–D: 630×; E & F: 400×). The uninjured artery is represented in A. Injured arteries were studied at 2 hours (B), 6 hours (C)i 48 hours (D), 7 days (E) and 14 days (F) after injury. The solid arrows represent the internal elastic lamina and L indicates the vessel lumen. The endothelial and adventitial layers of uninjured arteries expressed low constitutive levels of HA. At 2 hours after injury, macrophages and neutrophils adherent to the injured site demonstrated slightly elevated HA expression. The increased expression of RHAMM noted at 6 hours after injury was not mimicked in sections stained for HA. However, at 48 hours after injury, smooth muscle cells adjacent to the internal elastic lamina showed markedly elevated expression of HA. With the formation of the neointimal layer, increased expression of HA was continued in cells adjacent to the internal elastic lamina (open arrow) at 7 to 14 days after injury.

Figure 52B:
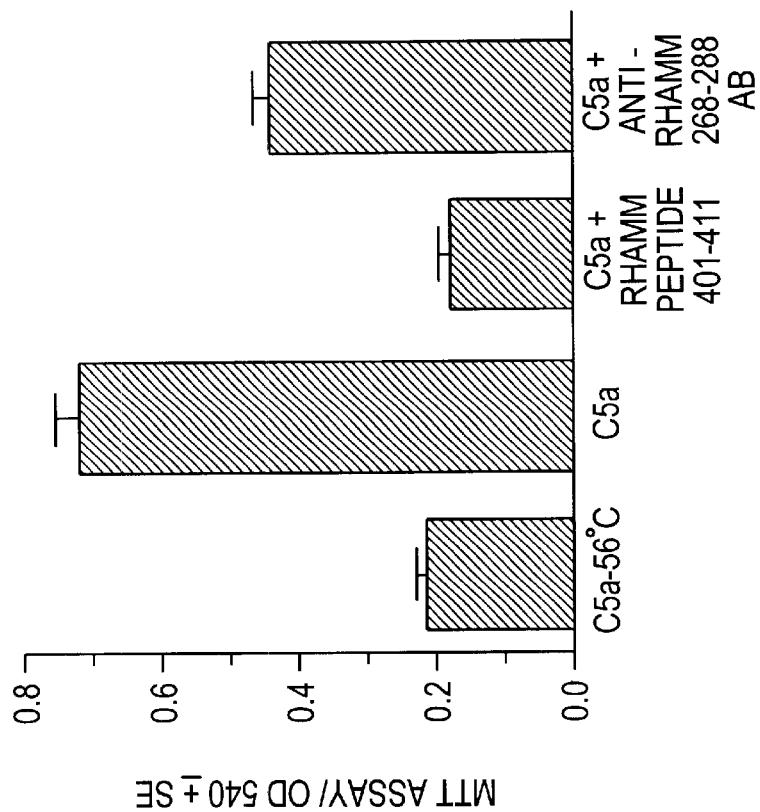
Figure 52A:
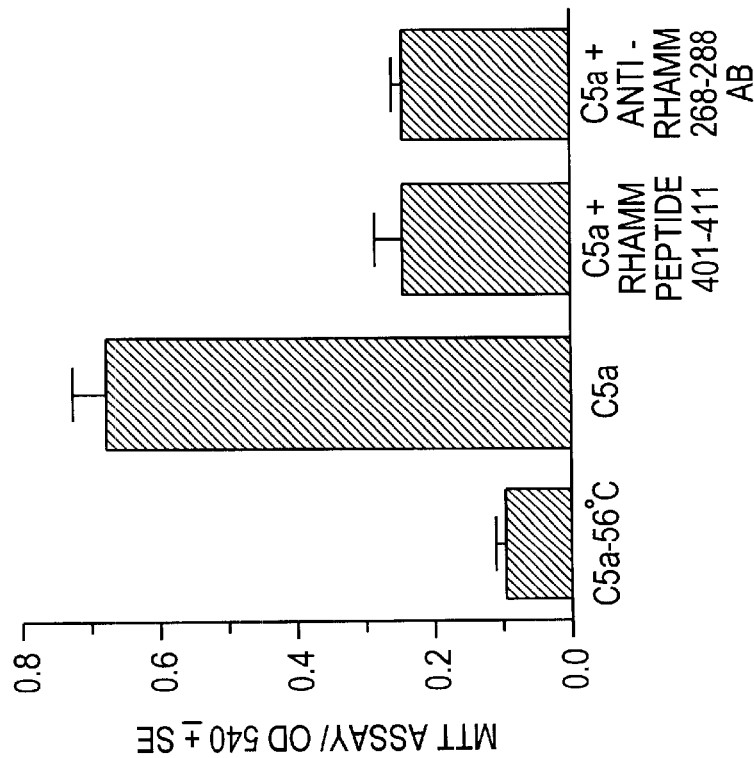
Figure 52C:
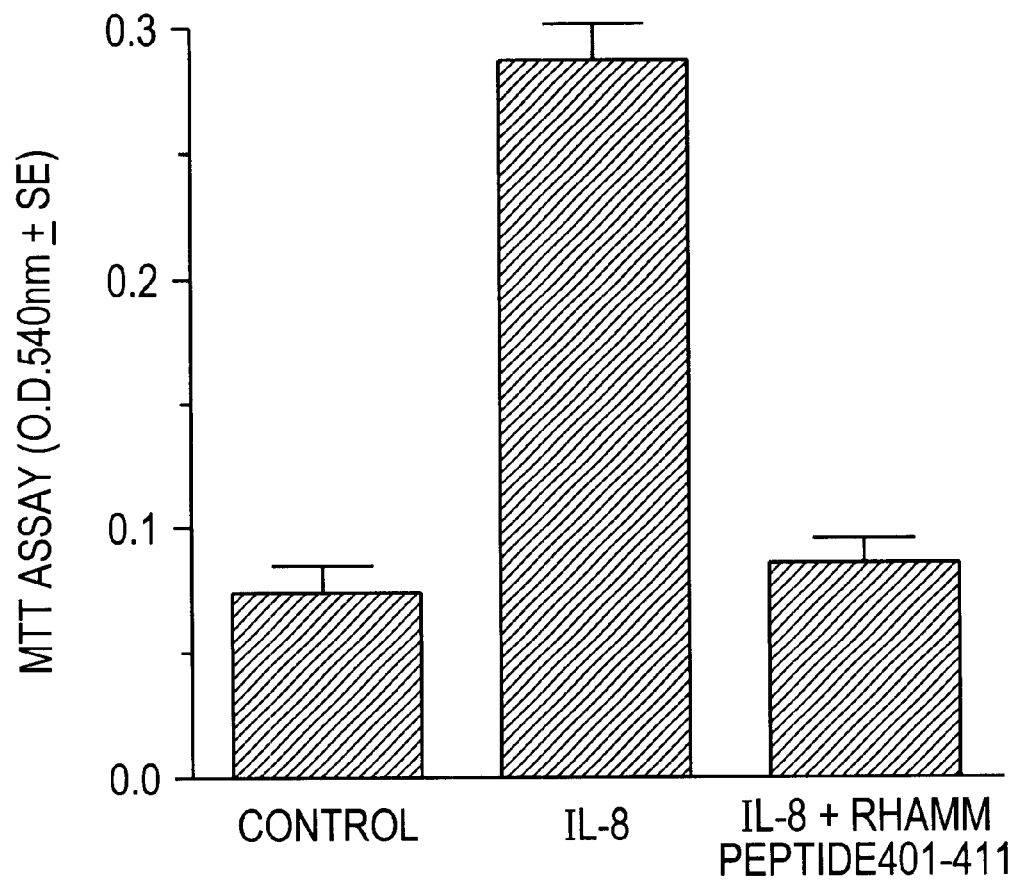

FIG. 52 shows effect of RHAMM peptide and antiserum on neutrophil and macrophage chemotaxis. Chemotaxis of human neutrophils and two macrophage cell lines (S1 and WEHI-3) to IL-8 and to endotoxin-activated mouse serum respectively was tested in a modified Boyden chamber assay. (a): Human neutrophil chemotaxis to IL-8 was completely inhibited by peptide $aa^{401-411}$, a peptide mimicking one of the HA-binding domains of RHAMM. (b): Both peptide $aa^{401-411}$ and anti-peptide $aa^{268-288}$ antiserum inhibited the chemotaxis of macrophage cell lines S1 and WEHI-3 to endotoxin-activated mouse serum. Heat-inactivated serum, used as a control, had no effect on neutrophil or macrophage chemotaxis.

Figure 53:
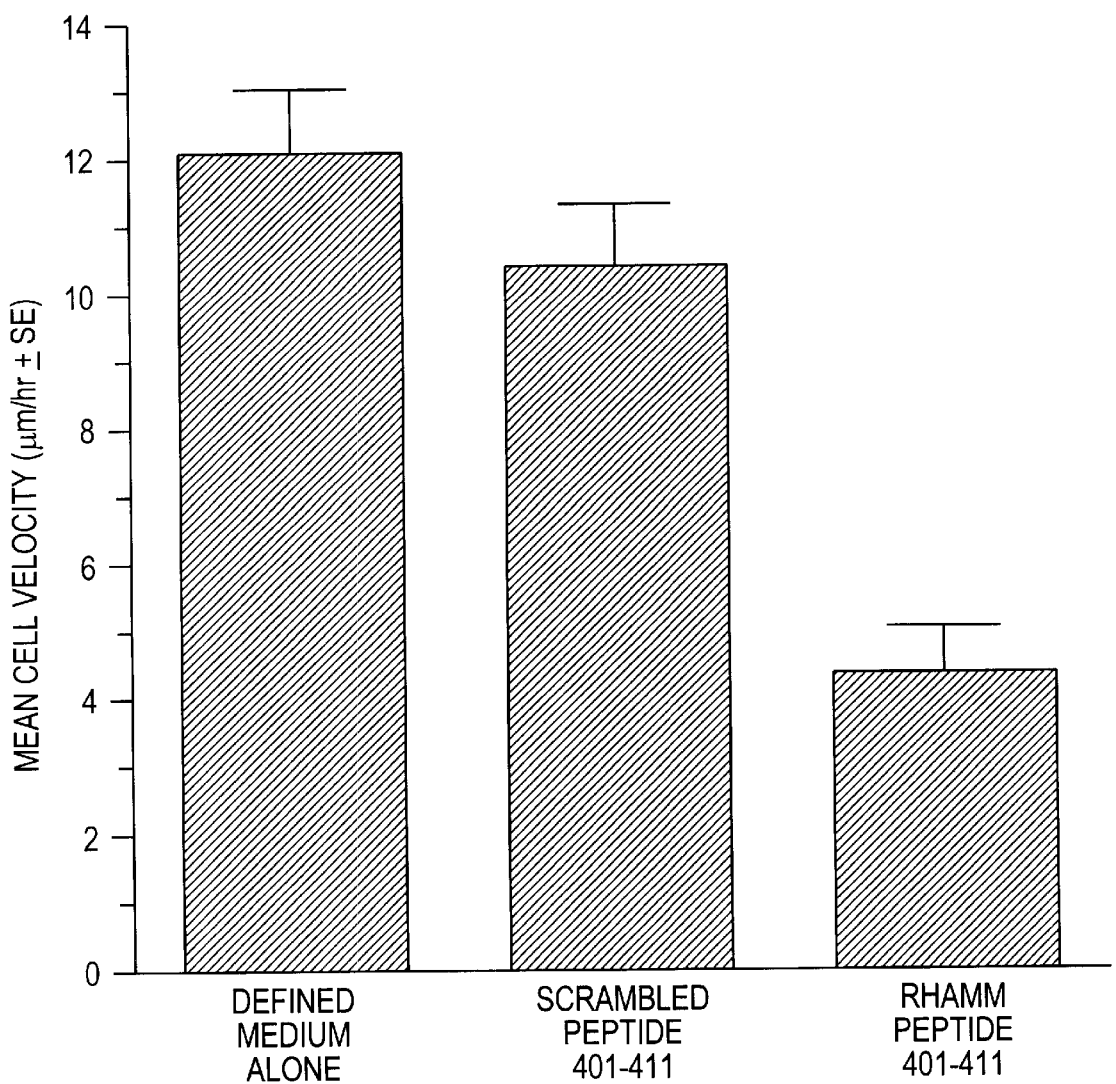

FIG. 53 shows RHAMM-HA-binding peptide ($aa^{401-411}$) inhibition of smooth muscle cell migration in vitro following single-scratch wounding of monolayers. Peptide $aa^{401-411}$, mimicking one of the HA-binding domains of RHAMM, significantly inhibited the rate of translocation of smooth muscle cells from the leading edge of wounds following single scratch wounding of monolayers. A scrambled peptide, containing the same amino acids but in a random orientation, had no effect on this migratory response to wounding.

Figure 54A:
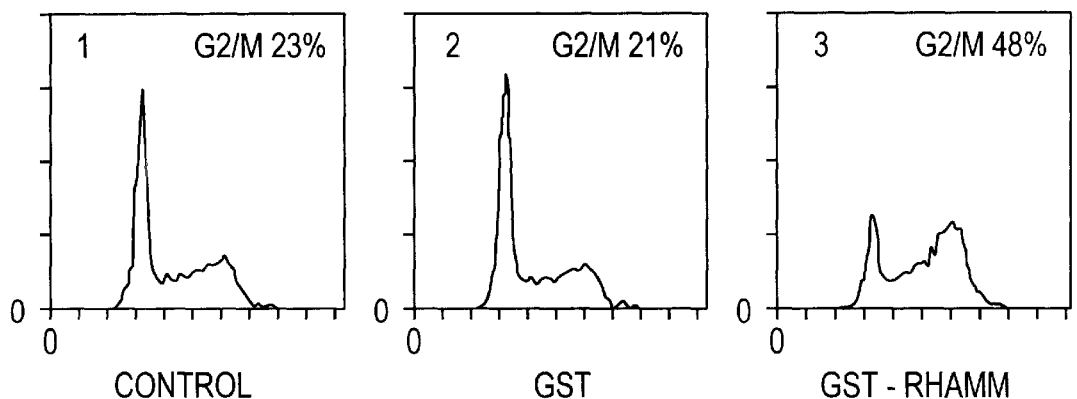

FIG. 54A shows flow cytometric analysis (relative DNA content plotted against cell number) of C3 cells serum starved for 40 hours and then serum stimulated in the presence of 5 µg/ml GST (Panel 2), 5 µg/ml GST-RHAMM (Panel 3) or control (Panel 1).

Figure 54B:
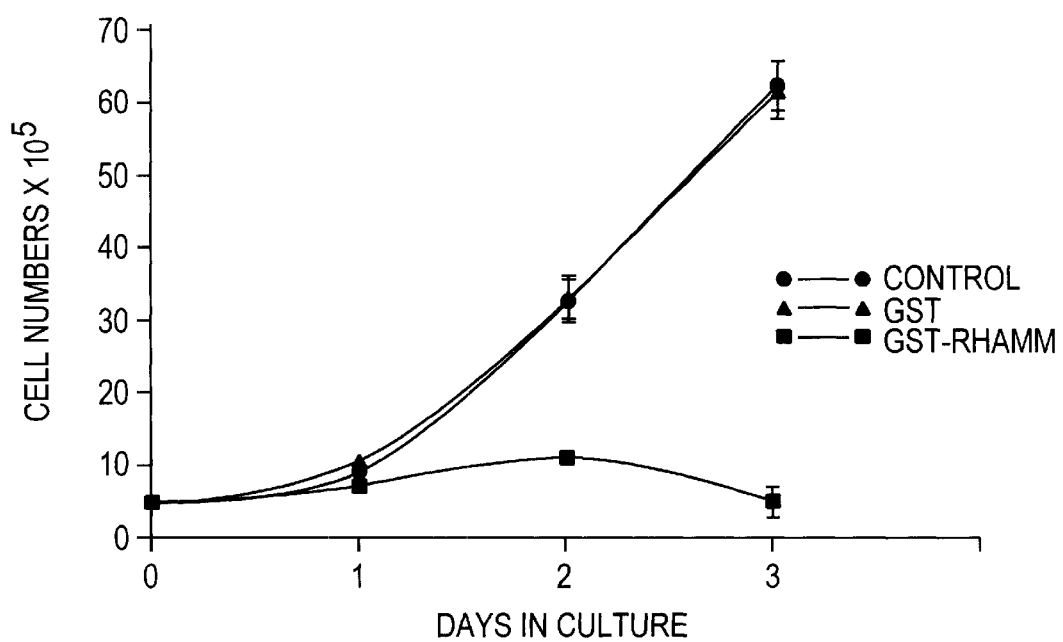

FIG. 54B shows growth curves of triplicate cultures of control C3 cells (●) and C3 cells cultured in the presence of 5 µg/ml GST (▲) or 5 µg/ml GST-RHAMM (■) Live cells were counted at daily intervals. Growth is expressed as cell numbers×$10^5$ (mean of triplicate with standard deviation) plotted against days in culture.

Figures 55A, 55B:
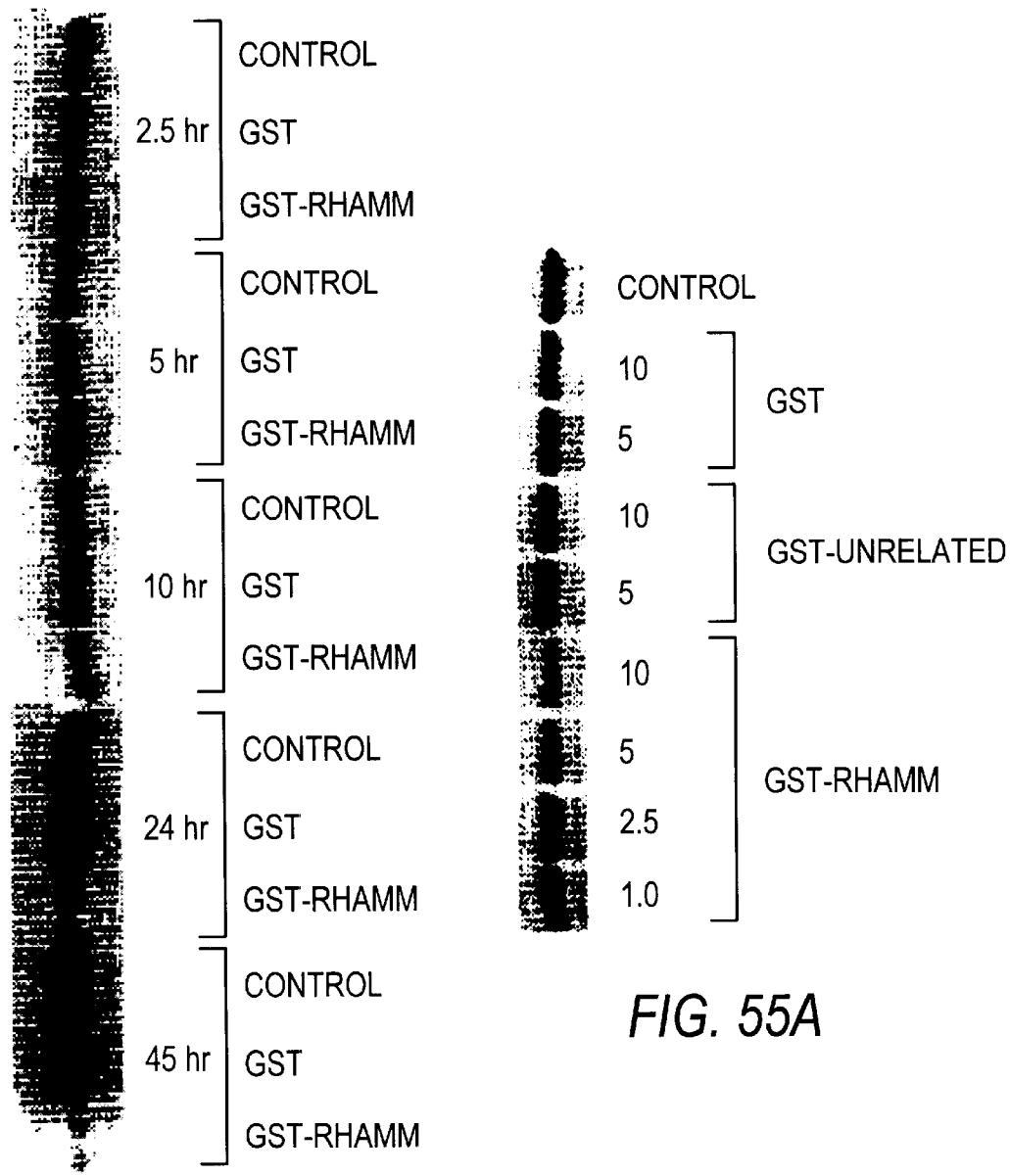

FIG. 55A shows a Western blot of $p34^{cdc2}$ protein expression in C3 cells serum starved then serum stimulated in the presence of the indicated concentrations (µg/ml) of GST alone (GST), GST-RHAMM fusion protein or GST fused to a protein unrelated to RHAMM (GST-unrelated).

FIG. 55B shows the time course of suppression of $p34^{cdc2}$ expression by GST-RHAMM in the cells of FIG. 55A.

Figures 56A, 56B:
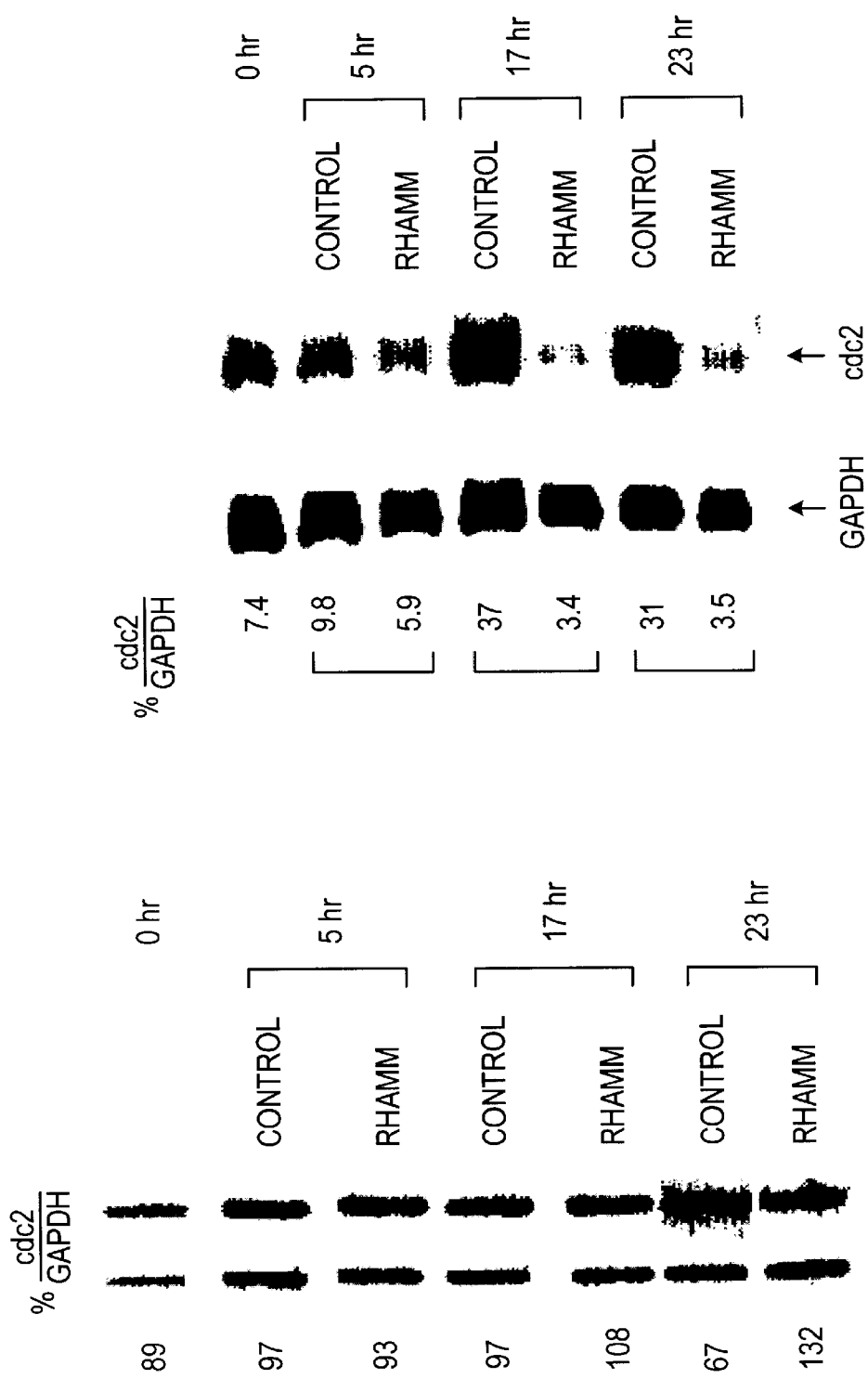

FIG. 56A shows a Northern blot of cdc2 mRNA expression over time in control C3 cells and in cells treated with GST-RHAMM. GAPDH served as housekeeping enzyme.

FIG. 56B shows the result of nuclear run-on assays on nuclei isolated from control and GST-RHAMM treated C3 cells.

Figure 56C:
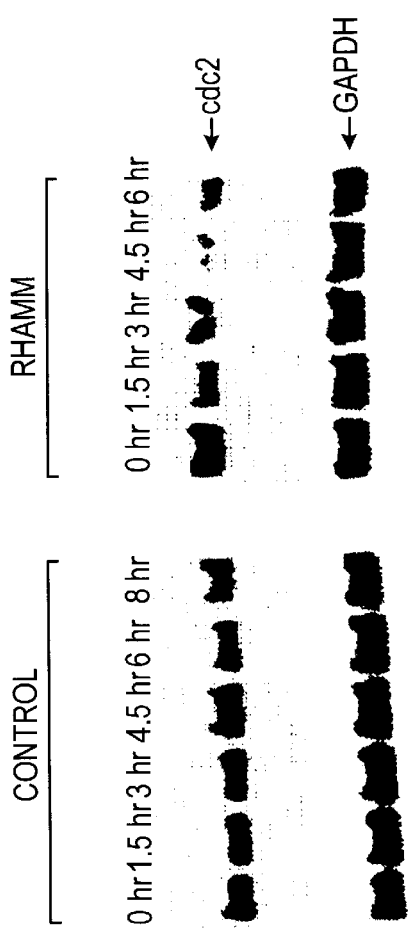

FIG. 56C shows cdc2 mRNA stability in control cells and GST-RHAMM-treated cells after actinomycin D treatment (20 µg/ml).

Figure 56D:
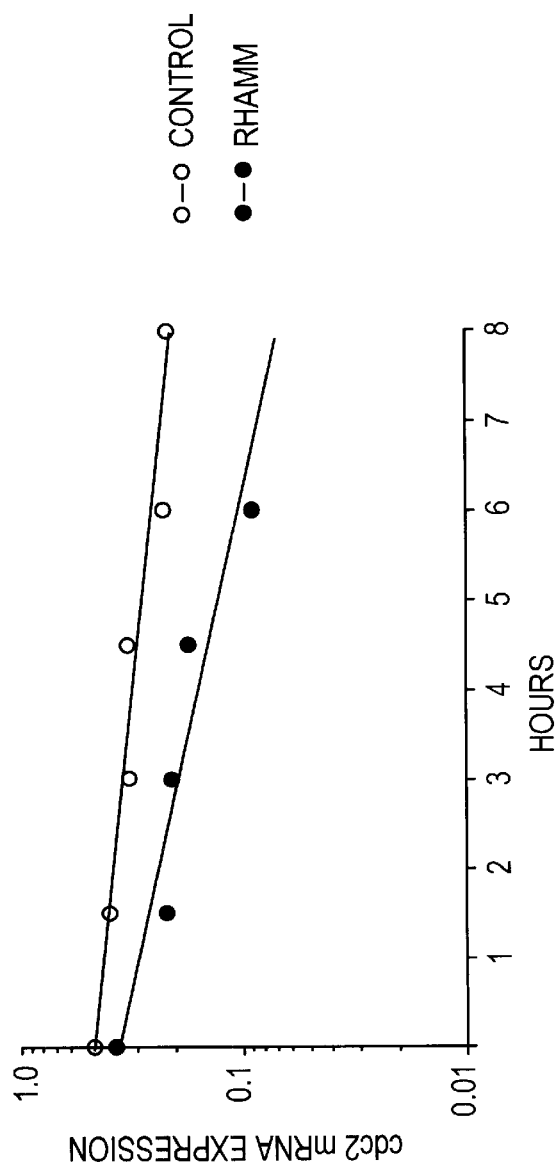

FIG. 56D shows determination of cdc2 mRNA stability in control cells (○) and GST-RHAMM treated cells (●) after actinomycin D treatment.

DESCRIPTION OF THE INVENTION

The inventors have previously cloned and sequenced the cDNA sequence coding for RHAMM II (Hardwick et al., 1992).

They have now obtained the complete genomic sequence for RHAMM II and for a longer version of the receptor protein, RHAMM I, and an alternate spliced variant, RHAMM I-2a. Both cDNA and genomic clones have been obtained for each of these isoforms.

The complete murine gene for the receptor protein spans 26 kilobases and comprises fourteen exons ranging in size from 60 to 1099 base pairs. Southern blot analysis indicates that the RHAMM gene occurs as a single copy.

Two new isoforms of RHAMM have been identified and cloned, the first, RHAMM I being encoded by exons 1 to 12, and the second, RHAMM I-2a, being encoded additionally by the alternatively spliced exon 2A, which encodes an additional insert of 25 amino acids.

FIG. 5 shows the nucleotide sequence (SEQ ID NO:3) and deduced amino acid sequence. (SEQ ID:4) of the alternately spliced exon 2A.

Two alternate mRNA's for RHAMM I have been found, RHAMM IA and RHAMM IB. The translated portion of these is identical and the divergence is in the 5' non-coding or untranslated region, apparently due to alternate splicing of exon 1B and alternate exon usage. The transcripts of RHAMM IA and RHAMM IB isoforms were synthesized from different start sites, separated by 1.8 kb.

FIG. 10 shows the nucleotide sequence of the shorter 5' sequence, RHAMM IB, and the longer 5' sequence, RHAMM I A (SEQ ID NO:5).

Primer extension studies indicated that the transcript start point (tsp) for RHAMM I is at portion−31. The protein (SEQ ID NO:2) has a deduced amino acid sequenced of 79 kDa; AUG 1 is used for translation initiation. The previously described RHAMM II is a shorter form of RHAMM I with multiple tsps initiating between AUG 1 and AUG 2. Exons 4 to 12 encode RHAMM II. Northern blot analyses of mouse fibroblast RNA using RHAMM cDNA probes identified at least two hybridizing species and in vitro translation of mRNA yielded proteins of 70 and 55 kDa. Transfection and overexpression of the RHAMM II isoform resulted in accumulation of a cellular 65 kDa protein. Similar transfection studies with the RHAMM I-2a isoform showed the overexpression of a 70 kDa protein in cell lysates and the accumulation of a 100 kDa secreted protein in the supernatant media. The complex structure of the gene therefore appears to allow multiple levels of expression and compartmentalization of the RHAMM protein.

RHAMM I and RHAMM II are predicted to be collinear isoforms such that RHAMM II is a truncated form of RHAMM I.

Evidence of the in vivo occurrence of RHAMM II is derived from several approaches. A previously published cDNA encoding RHAMM II has been isolated from a 3T3 expression library (Hardwick et al., 1992). The overexpression of the RHAMM II cDNA produces a 65 kDa protein which aligns with the size of a RHAMM protein seen in Western analyses of ras-transformed cells. Endoglycosidase treatment reduced the 65 kDa protein to a 55 kDa form which is consistent with the deduced amino acid sequence of RHAMM II and with the size of a protein immunoprecipitated after in vitro translation of RHAMM mRNA. Primer extension studies predict multiple potential transcription start sites for this isoform.

These data are consistent with the proposal that RHAMM II is generated from distinct transcripts rather than alternative initiation of translation from the longer RHAMM I. However, some of the tsps observed for RHAMM II may have resulted from secondary structures in the RNA creating pausing during the primer extension assays. The overexpression studies indicate that RHAMM II, unlike RHAMM I-2a, does not accumulate in the medium.

The heterogeneity manifested by the RHAMM gene has also been observed in another hyaluronan receptor, namely CD44. CD44 is by and large a constitutively expressed protein which occurs as a variety of isoforms that are generated by alternative exon splicing. However, the RHAMM gene appears to differ from that of CD44 in several important ways. Unlike CD44, the apparently more limited diversity of RHAMM is generated by some alternate splicing, alternate promoter usage and the translation of a truncated form which are targeted differently. Alternate splicing appears to be more restricted (data not shown) than that observed in the CD44 gene (Screaton et al., 1992). Although RHAMM and CD44 have both been implicated in cell adhesion, locomotion and tumour transformation (Stamenkovic et al., 1989; Stamenkovic et al., 1991), differences in their regulation predict that they may have distinct roles in these biological processes.

The nucleotide sequence of intron 2 is shown in FIG. 11 (SEQ ID NO:7).

Analysis of sequences both in intron 2 and 5' of RHAMM IA and RHAMM IB indicated the presence of several promoter regions (data not shown) predicting that the different isoforms are alternately regulated. A similar spatial separation of alternate promoters driving the transcription of different isoforms, is seen in the β-galactoside α2,6-sialyltransferase gene(Wang et al., 1990) and the angiotensin I-converting enzyme (ACE) gene (Hubert et al., 1991).

RT-PCR and Southern analysis have indicated the existence of additional alternate exons within intron 2.

RHAMM is a glycoprotein that is critical to cytokine, oncogene and injury-regulated locomotion: RHAMM is required for cell locomotion in response to TGF-$\beta_1$, the activated ras oncogene, bleomycin-induced lung injury and culture wounding, as demonstrated by antibody blockade and peptide mimicry studies (Khalil et al., 1989; Turley et al., 1991; Samuel et al., 1993). RHAMM is also critical to proliferation of normal and transformed cells. Expression of cell surface RHAMM is tightly regulated, being absent in most normal tissues, but increasing upon tissue injury in macrophages, epithelium, fibroblasts and smooth muscle cell populations. In vitro cell surface RHAMM expression is density-and transformation-dependent so that it is only expressed for a few days after the subculture of normal cells, but is elevated upon exposure to cytokines (Samuel et al., 1993) or to oncogenes (Turley et al., 1991). Collectively, these results indicate a critical role for RHAMM in cell locomotion, particularly during injury and oncogenesis.

RHAMM is expressed on the cell surface, as determined by surface labelling, FACS analysis, subcellular fractionation and sensitivity of RHAMM to light protease treatment.

High expression of surface RHAMM coincides with maximal rate of cell locomotion in ras-transformed cells and in cells after stimulation with TGF-$\beta_1$ (Samuel et al., 1993).

In contrast to the cell associated form of RHAMM, soluble forms of RHAMM have been shown by the inventors to inhibit cell locomotion.

C3 fibroblasts have been shown to secrete a soluble form of RHAMM as described in Example 5.

When culture medium was removed from these cells, treated to remove secreted RHAMM and returned to the cells, cell motility was found to increase.

The soluble form of RHAMM designated RHAMM I-2a has been shown to promote focal adhesion and cell spreading as seen in FIG. 12.

The inventors have also made soluble RHAMM-GST fusion proteins and shown that these inhibit cell locomotion, as described in Example 6. Cells in cultures supplemented with RHAMM, prepared as a glutathione S-transferase-RHAMM fusion protein, exhibited a significant (3.5 fold) reduction in locomotion at concentrations of GST-RHAMM as low as 1 ng/ml. GST-alone or GST/bovine serum albumin (BSA) fusion protein had no effect on cell locomotion. Addition of RHAMM fusion protein in which the HA binding domains were mutated was found to have no effect on cell motility indicating that these domains were critical to the inhibitory activity of secreted RHAMM. This is consistent with the observation that addition of peptides (10 ng/ml) that mimic the HA binding domains of RHAMM reduced locomotion to approximately 70% of control values. However, a GST-fusion protein generated by removal of the entire carboxy terminus region of RHAMM cDNA, which includes the sequence encoding the HA binding domains, retained a portion of the inhibitory effects seen with intact RHAMM thus revealing the presence of additional inhibitory sites within the protein.

Soluble RHAMM inhibits cell locomotion as a result of multiple sites within the protein that include its HA binding domains (Yang et al., 1993, 1994). Deletion/mutation of the HA binding domains via two distinct methods completely abolishes this protein's inhibitory effect. Likewise, peptides that mimic the HA binding domains of RHAMM produce the entire inhibitory action seen with the whole protein thus firmly establishing the importance of these domains for the effect of soluble RHAMM on cell motility.

It is proposed that one means of regulation of RHAMM-induced cell locomotion is the ratio of cell associated RHAMM: soluble RHAMM.

By providing the means of expressing RHAMM proteins, the inventors have provided a means of modulating this cell-associated/soluble RHAMM ratio and thereby of modulating or controlling cell adhesion or locomotion.

It is proposed that soluble RHAMM inhibits cell locomotion by binding to extracellular HA, thus preventing it from interacting with cell associated RHAMM.

The inventors have also shown that over-expression of RHAMM is oncogenic.

Overexpression of the RHAMM I gene by transfection into fibroblasts caused loss of contact inhibition of growth, elevated motility and anchorage-independent growth, as described in Example 4. When inoculated into mice subcutaneously or intravenously, the cells formed fibrosarcomas and lung metastases, respectively. H-ras-transformed fibrosarcomas transfected with a dominant suppressor mutant of RHAMM exhibited a 'revertant' phenotype and were completely non-tumorigenic and non-metastatic despite their continued elevated expression of p21™ oncoprotein. Fibroblasts stably expressing RHAMM in the antisense orientation produced low levels of RHAMM protein and were resistant to ras-transformation. These results provide the first evidence of the oncogenic potential of an ECM receptor that regulates cytoskeletal organization.

A similar oncogenic effect was seen with transfection into fibroblasts of a cDNA encoding RHAMM I-2a. In contrast, transfection with RHAMM II cDNA did not lead to transformation.

The invention provides a method for reversing the transformed phenotype resulting from H-ras transformation of mammalian cells comprising transfecting the cells with a dominant suppressor mutant of the RHAMM gene.

The invention provides a further method for reversing the transformed phenotype resulting from H-ras transformation of mammalian cells comprising transfecting the cells with an antisense RHAMM cDNA.

Breast cancer is the most common malignant disease among women and represents a major cause of death in Western countries (Harris et al., 1992). Invasion and metastasis of the primary tumour remains the major cause of the fatal outcome of this particular malignancy (Price, 1990). Several cellular growth factors, cytokines, and oncogenes may play critical roles in the process of malignant transformation and progression in human breast cancer (Dickson et al., 1992).

The present inventors have now shown that six human breast cancer cell lines express RHAMM and require this protein for locomotion. Levels of expressed RHAMM correlated positively with the motile properties of the cell lines. Conversely invasive properties correlated with high HA production. Although invasion required RHAMM, invasiveness did not consistently correlate with motility. Since normal human breast ducts and glands expressed little RHAMM, while malignant tumours expressed much higher levels of this protein, this receptor likely plays a critical role in breast cancer cell progression in vivo, possibly as a result of its ability to regulate fundamental properties such as invasion and locomotion.

The MDA-MB-231, MDA-MB-468 and Hs-578-T cell lines are oestrogen receptor negative and hormone independent, while MCF-7, ZR-75-1, and T-47-D are oestrogen receptor positive and hormone dependent. The MDA-MB-231 and Hs-578-T cell lines have previously been shown to form invasive, penetrating colonies in a Matrigel outgrowth assay, to be invasive and metastatic in NCr nude mice and to invade in Boyden chamber chemoinvasion assays (Sommers et al., (1991); Thompson et al., (1992); Bae et al., (1993)). Our results indicate that random locomotion is not related to oestrogen receptor status, but related to levels of RHAMM expression and HA release. our results that HA production is highest in the most invasive cell line is consistent with previous evidence linking HA to invasion (Knudson et al., 1989).

The precise role of HA in invasion is not clear. It is likely that at least part of the effects of HA is through an HA/RHAMM autocrine mechanism (Samuel et al., 1993) which results in a protein tyrosine phosphorylation cascade that effects focal adhesion turnover, initiating and enhancing cell locomotion that is necessary for invasion. Also, HA may indirectly influence cell behaviour by affecting the structure of the ECM (Knudson, supra).

The inventors' findings that RHAMM contributes to the motility and invasion of metastatic human breast cancer cells in vitro and that RHAMM expression is associated with tumourigenesis and progression in human breast cancer in vivo indicate that RHAMM provides a useful diagnostic marker as a prognostic indicator in human breast carcinoma.

It has been shown in animal models that control or suppression of tumours can be achieved by gene therapy, for example by administration of suitable anti-sense DNA sequences to suppress activity of a relevant gene.

The present inventors have shown that overexpression of the RHAMM gene is associated with transformed and oncogenic cell properties and that these properties can be suppressed and the oncogenicity of the cells reversed by suppression of RHAMM gene expression by transfection of a dominant suppressor mutant DNA or an antisense DNA directed against the RHAMM gene. Such transfections offer a therapeutic approach for tumour control or suppression. In particular, the work of the inventors indicates that the sequence encoded by the 2A exon is very important in the link between RHAMM expression and transformation and oncogenicity. Antisense sequences directed at the 2A exon can therefore be employed as the basis of therapeutic intervention to control or suppress tumours.

Antisense sequences can be applied for example, by injection into a tumour to control tumour growth. The inventors have shown that RHAMM I-2a is the isoform which is overexpressed in tumours and the overexpression of the 2A exon can be used as a diagnostic marker and a prognostic indicator in human cancer, as exemplified by the results described in Example 8.

The peptide encoded by exon 2A can be synthesised and antibodies to it can be raised by conventional methods, preferably after conjugating the peptide to another antigen such as keyhole limpet haemocyanin. If mice are inoculated with the conjugated antigen, spleen cells can be obtained and hybridomas produced, as will be understood by those skilled in the art. Screening by conventional methods can be carried out to obtain a hybridoma producing Monoclonal antibody with maximum affinity for the exon 2A peptide. The selected antibody to exon 2A peptide can be used to construct a conventional ELISA, permitting screening of human serum for soluble RHAMM containing that peptide. Comparison with standard values obtained from normal patients can be used for comparison to indicate overexpression and the presence of tumour.

Alternatively, biopsy samples of human tumours can be examined for the level of RHAMM protein or exon 2A peptide overexpression by histochemical means, (paraffin sections or frozen sections) to provide an indicator of likely prognosis. Histochemistry can be carried out as described in Example 7 for RHAMM overexpression. A similar method can be carried out employing an antibody specific for exon 2A peptide, prepared as described above. The higher the level of RHAMM or 2A expression, the poorer the prognosis for the patient, as shown in Example 8.

A further method of assessing tumour prognosis in humans is to assess the level of mRNA for RHAMM in tumour samples. A biopsy sample is sectioned and the RNA of a section of tumour tissue is solubilised and subjected to RT-PCR and Northern blotting, allowing quantitation of the level of mRNA for RHAMM. Overexpression of RHAMM RNA indicates a poor prognosis. This method also allows the determination of which RHAMM isoforms are being expressed by tumour tissue, by selection of appropriate primers for the RT-PCR process.

Smooth muscle cell migration forms a critical component of the pathogenesis of restenosis after balloon angioplasty (Cascells, 1992). Also the accumulation of inflammatory cells at sites of injury requires their chemotactic migration to the site of injury and subsequent adherence.

The observation that both neutrophil and macrophage chemotaxis can be blocked by using either anti-RHAMM antisera or a peptide mimicking one of the HA-binding domains of RHAMM suggests that RHAMM:HA interactions contribute to the accumulation of inflammatory cells at the injury site.

The present study showed that the uninjured carotid artery expressed a 65 kDa RHAMM and that following injury, a 70 kDa isoform appeared. This RHAMM isoform was expressed between 36 and 72 hours after injury, and coincided with reports of the timeframe for early migration of smooth muscle cells into the injured site. Increased staining for HA occurred within the time period of smooth muscle cell migration and coincided with the expression of the 70 kDa RHAMM isoform.

The results of the inventors on the inhibition of white cell infiltration by anti-RHAMM antisera or by peptides mimicking one of the RHAMM HA-binding domains indicates that these agents can be employed as therapeutic agents in any condition in which one wishes to suppress white cell infiltration. One example is the infiltration of grafted tissue by host white cells; anti-RHAMM antisera or peptides mimicking the HA-binding domains offer a means of controlling or reducing graft rejection in humans.

The work described in Example 9 also indicates that the present invention provides a means for controlling or reducing restenosis after angioplasty. It has been shown in animal models that sprinkling of anti-restenosis agents such as anti-sense oligonucleotides on restenotic plaques within a blood vessel can prevent/reduce restenosis (Simons et al., (1992), Nature, 359 (6390): 67–70).

Application of a peptide mimicking one of the HA-binding domains of RHAMM to a blood vessel after angioplasty will reduce both inflammatory cell and smooth muscle cell infiltration. The peptide can be applied to the surface of the vessel after surgery.

The RHAMM Gene Encodes Several Protein Isoforms

The genomic structure of RHAMM is more complex than was predicted by the previously reported cDNA (Hardwick et al., 1992). Exons 4 through 12 correspond to the previously isolated RHAMM cDNA (RHAMM II), whose deduced amino acid sequence predicted a 44 kDa protein. However, sequencing the genomic clones revealed that there were a further three exons of open reading frame (exons 1 to 3) upstream of exons 4–12. The deduced amino acid (sequence of exons 1 to 12 predict a 70 kDa protein (RHAMM I) (SEQ ID NO:1 and SEQ ID NO:2). The two proteins overlap such that the deduced amino acid sequence of RHAMM I includes the RHAMM II sequence plus an additional 129 amino acids at the amino terminal end (FIGS. 1, 2 and 3).

RT-PCR, sequencing and Western analysis were used to demonstrate the existence of the RHAMM I isoform and to confirm that exons 1–3 were coding exons. In RT-PCR analysis, 1st strand cDNA, derived from reverse transcribed cytoplasmic 3T3 RNA, was used as a template. Two primers, one at the start of exon 1 and one in the 3' non-coding region of RHAMM II, were used for amplification. The resulting 2.2 kb fragment was sequenced and shown to be identical with exons 1–12. RT-PCR, using the same two primers, also identified an alternately spliced exon of RHAMM I, namely exon 2A (SEQ ID NO:3), which a 25 amino acid insert in the amino terminal end of RHAMM (FIG. 5), this isoform being designated RHAMM I-2a. (cDNA sequence: Sequence ID NO:10 and amino acid sequence: Sequence ID NO:11.

Transfection and overexpression of RHAMM II cDNA resulted in an overexpression of a 65 kDa protein in cell lysates (FIG. 6A). RHAMM II protein did not accumulate in supernatant media. Endoglycosidase treatment of the 65 kDa protein reduced it to 55 kDa species (data not shown). A corresponding band of 55 kDa was seen when mRNA from 3T3 fibroblasts was translated in vitro (FIG. 7).

Transfection and overexpression of RHAMM I-2a produced two proteins of MW 70 kDa and 100 kDa. The 70 kDa protein was overexpressed in transfected cell lysates (FIG. 6B). The 100 kDa protein was overexpressed and accumulated in the supernatant media (FIG. 6C) of transfected cells. Ras-transformed cells also accumulated the 100 kDa RHAMM protein in the supernatant media. Endoglycosidase treatment of the 100 kDa protein reduced it to a 70 kDa form (data not shown) and a 70 kDa protein was observed from in vitro translation of mRNA (FIG. 7). Preabsorption of the anti-RHAMM peptide antibody with RHAMM fusion protein indicated the specificity of the 100 kDa RHAMM bands (FIG. 6C). The proteins encoded by RHAMM I, RHAMM I-2a and RHAMM II did not have transmembrane domains. Possible weak signal sequences exist in the proteins encoded in RHAMM I and I-2a isoforms. Neither protein has homology to other protein sequences recorded in the data banks.

RHAMM Contains Internal Transcription Start Points (tsys)

Figure 8A:
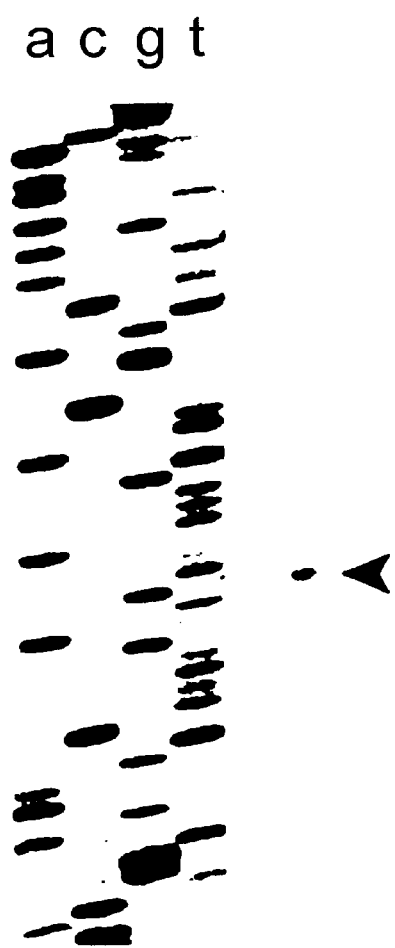
Figure 8B:
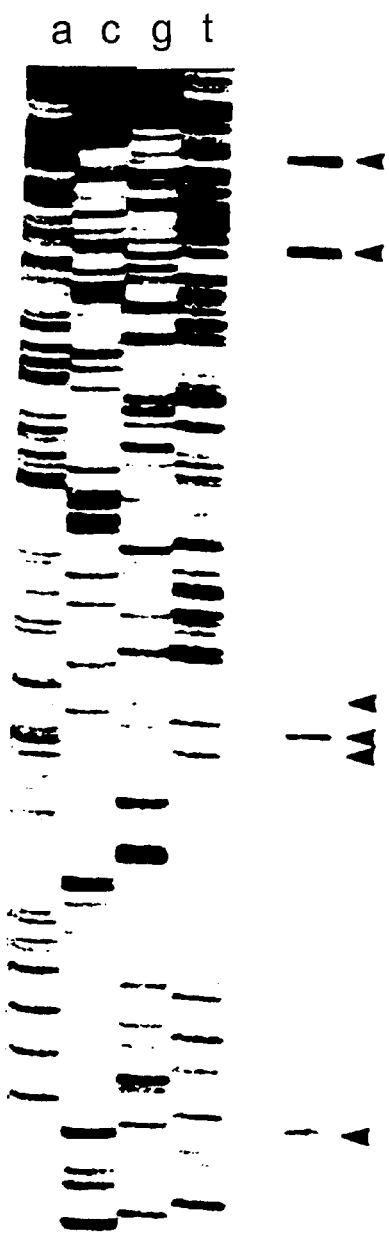

Primer extension assays predicted the occurrence of two classes of transcript and identified the transcript start points (tsps) that would theoretically yield two classes of RHAMM isoforms (FIGS. 8A and 8B). The tsp of RHAMM I was identified as a G residue-31 bases upstream of the AUG 1 codon (FIG. 8A). There were six tsps for the RHAMM II isoform which would initiate internally between AUG 1 and AUG 2 (FIG. 8B) in positions 83, 126, 129, 290 and 383 nt upstream of AUG 2. Products were sequenced for confirmation. Of the 6 tsps observed, three were strong bands and three were weak, (FIG. 8B). Transcript start points in positions 83, 126, 129, 134 and 290 use AUG 2 for initiation of translation. It is unknown whether tsp 383 would use AUG 2 given that there are other possible initiators prior to AUG 2. The results suggest the presence of a family of RHAMM mRNAs with 5' ends starting downstream of AUG 1 which will produce the truncated RHAMM II. Although these results are reproducible we cannot totally exclude that some of the weaker tsps were due to secondary structure interference in the primer extension assays. It is possible that a single transcript is made and that the RHAMM I and RHAMM II isoforms are produced by alternate initiation of translation. However, our data are consistent with production of alternate transcripts.

Several RHAMM mRNA Transcripts are Transcribed

There are multiple RHAMM transcripts which are consistent with the presence of several RHAMM proteins, found both in cell lysates and on in vitro translation of mRNA. Northern blots of 3T3 fibroblast total RNA, using cDNA derived probes, identified two hybridizing species of 4.2 kg and 1.7 kb. The 4.2 kb band is very broad spanning 3.9 kb to 4.2 kb and represents several message populations (FIG. 9). Indeed early exposures of Northern blots indicate several distinct bands in this region (data not shown). The origin of the 1.7 kb species is unknown. Given that two distinct 5' non-coding regions of RHAMM I have been identified, as described below, and given the alternately spliced exon 2A and the existence of the truncated RHAMM II transcripts, the presence of several messages of a similar size is not unexpected.

The RHAMM I Isoform has Different 5' Non-coding Regions

Figures 10A, 10B:
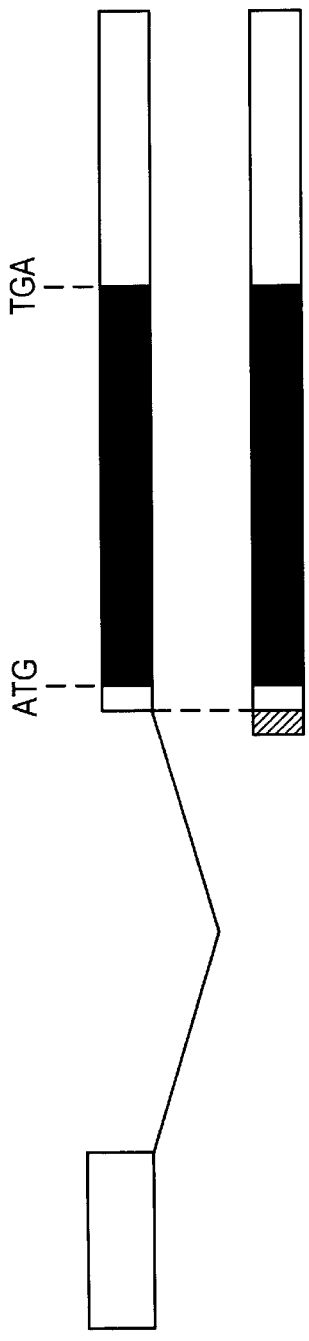
Figure 12A:
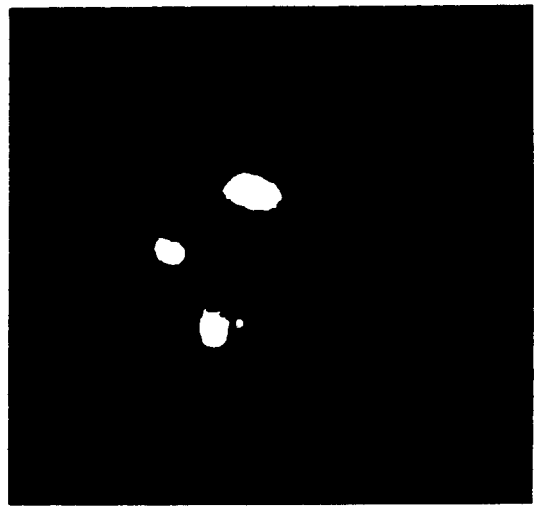
Figure 12B:
Figure 12C:
Figure 12D:
Figure 12E:
Figure 12F:

To determine the 5' end of the mRNA, the 5' RACE technique was used which yielded a 350 bp product that was subsequently sequenced. The sequence of this fragment is shown and compared to that already known from RT PCR studies on RHAMM I cDNA (FIG. 10A). The sequences are identical for 24 nt upstream of AUG 1 then the two sequences diverged. The longer sequence RHAMM IA, generated by the 5' RACE, is found in an exon 1.8 kb upstream from RHAMM IB. The protein coding sequences for both forms are identical, initiating with AUG 1. However, alternate splicing in exon IA and alternate exon usage produced two entirely different 5' non-coding regions, as shown in FIG. 10 (SEQ ID NO:5 and SEQ ID NO:6).

The Secreted RHAMM I-2a Induces Focal Adhesion Formation

While cell associated RHAMM has been implicated in elevated cell motility and focal adhesion turnover, a role for the secreted isoform of RHAMM had not been determined prior to the work of the present inventors. The inventors have prepared GST-RHAMM fusion protein and found that it was an effective inhibitor of cell motility in ng. quantities. Controls using GST (glutathione S-transferase) alone and GST fused to a control inactive protein had no effect on cell mobility, as described in Example 6. GST-RHAMM I-2a fusion protein was also prepared and added to the ras-transformed fibroblast cell line C3 at various concentrations for 2 hours and the effect on cell morphology was observed. Addition of RHAMM I-2a appeared to stimulate cell spreading of these normally rounded fibroblasts (data not shown).

The effect of RHAMM I-2a fusion protein on focal adhesion demonstrated by means of vinculin immunofluorescence, of the same C3 fibroblast line, was examined. As seen in FIG. 12, Panel A, untreated C3 fibroblasts showed only 5% of cells with vinculin positive plaques. In contrast, RHAMM I-2a treated cells showed a large increase in the number of plaque-positive cells (>50% with 100 ng/mL and 1 mg/mL treatments, as seen in FIG. 12, Panels D and E).

Focal adhesions are sites of ECM receptor-cytoskeletal interactions where second messenger signalling occurs in response to ECM and some growth factors. These structures are believed to be critical for the regulation of growth and motility (Woods and Couchman, 1988; Burridge et al., 1988).

This promotion of formation of focal adhesions by soluble RHAMM suggests that this isoform may antagonise the actions of cell-associated RHAMM.

Overexpression of RHAMM in Fibroblasts Induces Transformation

Since it had been previously shown that RHAMM expression was elevated in ras-transformed cells (Turley et al., 1991; Hardwick et al., 1993), the contribution of RHAMM to the transformation process was investigated by its overexpression in non-senescing fibroblasts. 10T½ fibroblasts were transfected with either a genomic RHAMM clone, from intron 2, which contains promoter elements, to the exon 12, (FIG. 13A) or a RHAMM cDNA encoding the isoform RHAMM I-2a (FIG. 13B). Both transfections were chemically selected in G418 and cell lines cloned. Five clones that overexpressed RHAMM as determined by Western blot analysis of cell lysates (Table 2) and Northern blot analysis of RHAMM RNA were selected from each transfection. These selected clones were further characterized and their properties are summarized in Table 2. Western and Northern analyses of one of these clones (G12) is diagrammed in FIGS. 13C & D. Cells transfected with the RHAMM gene overexpressed a 66–70 kDa protein consistent with the predicted size of RHAMM (Hardwick et al., 1992). The same cells displayed an increase in a 4.2 Kb message, the size of the major RHAMM mRNA transcript (Hardwick et al., 1992). The presence of the transfected RHAMM gene in all clones was confirmed by PCR detection of plasmid arms (data not shown). The selected clones overexpressed products of the RHAMM gene at the cell surface as determined by FACS analysis (Table 2). Transfected cells appeared morphologically transformed (FIG. 14A) in that they were rounded and showed no evidence of contact inhibition. Moreover, they exhibited a high nuclear overlap index comparable to that of ras-transformed cells (FIG. 14B, Table 2) and formed multiple foci in culture unlike the empty vector controls or the 10T½ parent cell line (Table 2, FIG. 16). Furthermore, transfected cells reached culture confluence at a 3–4 fold higher cell number relative to empty vector or parent line controls (FIG. 15). The rate of random locomotion of the transfected cells was 2 fold higher than control cell lines, a rate comparable to the ras-transformed C3 cell line (Table 2). This high motility was maintained at sub-confluence and was blocked by anti-RHAMM antibodies (Table 2). The rate of growth of RHAMM transfected cell lines was less than that of ras-transformed C3 cells, and in fact, identical to the control cells until confluence halted growth of the latter (FIG. 15). Nevertheless, RHAMM transfected cells grew in an anchorage-independent fashion in soft agar (Table 3). Similar results on cell behaviour were obtained after transfection of the RHAMM I-2a cDNA in a pHβAP-3P-Neo vector into 10T½ fibroblasts (Table 2). Transfection of RHAMM I-2A cDNA containing mutated HA binding domains had no effect on morphology, contact inhibition or motility (Table 2). Transfection of 10T½ cells with cDNA for RHAMM II did not lead to the appearance of transformed characteristics, suggesting that exon 2A is crucial in producing transformation.

Figure 17A:
Figure 17B:
Figure 17C:
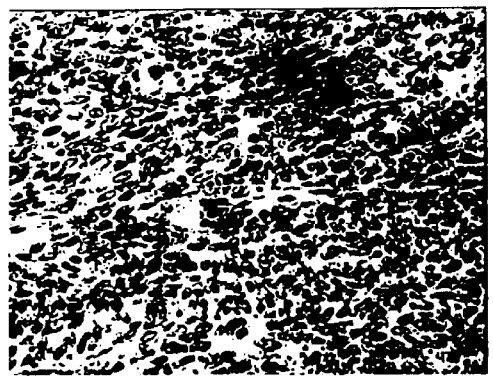
Figure 17D:
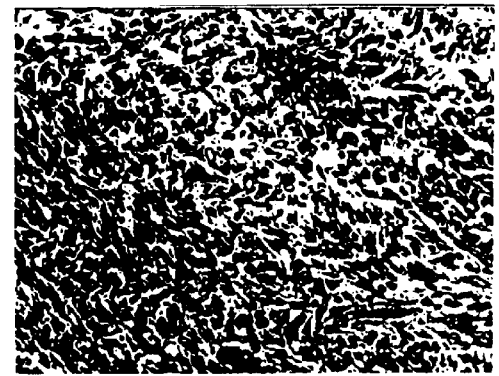

To determine whether cells transfected with RHAMM gene were tumorigenic, 1–5×10$^6$ cells were injected subcutaneously into the right hind leg of syngeneic mice. Fibrosarcomas formed within three weeks; no tumors formed in mice injected with vector or 10T½ parental control cells (FIG. 17 and Table 3). Tumors derived from the transfected cells were identical histologically to those formed by ras-transformed cells (FIGS. 17C, D) and expressed high levels of RHAMM as seen immunohistochemically. Cells injected into mice via the tail vein invaded lung tissue (FIG. 17a) and formed metastatic nodules (FIG. 17b). Cells transfected with RHAMM I-2a cDNA were also tumorigenic and metastatic, but cells expressing the mutated RHAMM I-2a were not (Table 2).

Reversion of H-ras-transformation with a Dominant Suppressor Mutant of RHAMM

The importance of RHAMM for maintenance of the transformed phenotype of H-ras-transformed fibrosarcomas was examined by blockade of RHAMM function with a RHAMM cDNA mutated at its HA binding domains (FIG. 18A). Such suppressor mutations have been previously prepared by mutating the kinase domain (Evans et al., 1993) or deleting the cytoplasmic domains of other receptors (Kashles et al., 1991). The present approach to functional ablation was taken since RHAMM is secreted, is localized at the cell surface and forms homodimers (Hardwick et al., 1992; Klewes et al., 1993). Furthermore, mutation of the RHAMM HA binding domains destroys its ability to morphogically transform fibroblasts (Table 2). Collectively, these conditions have been found to be sufficient to construct suppressor mutations of such growth factor receptors as TGFβ$_1$ (Brand et al., 1993). The details of the amino acid substitutions in the HA binding domains of RHAMM are outlined in FIG. 18A. Loss of HA binding was confirmed using the mutated RHAMM fusion protein in a transblot assay (FIG. 18B) the specificity of which has previously been demonstrated (Hoare et al., 1993). Ras-transformed C3 cells were transfected with the mutated RHAMM and chemically selected in G418. A flattened cell shape (ie. see FIG. 22c) was typically observed in 25% of the selected cells, and over 20 clones of these cells were obtained. Three clones containing the mutated RHAMM protein were selected for further analysis and all three were found to overexpress RHAMM by 2–3 fold as determined by Western blot analysis (see FIG. 19). Increased cell surface expression of RHAMM was detected by FACS analysis using antibody A268 (Hardwick et al., 1992), which specifically recognizes a peptide encoded in the RHAMM cDNA (aa$^{268-289}$) that is 5' to the mutated region of the protein (FIG. 20). All clones overexpressing mutant RHAMM exhibited levels of activated p21$^{ras}$ protein that were comparable to or higher than those seen in the control H-ras transformed C3 cells transfected with vector only (FIG. 21). GTP binding assays indicated similar levels of ras activity in the transfected and C3 cell lines (data not shown).

Clones expressing mutated RHAMM were contact inhibited and displayed a low nuclear overlap ratio comparable to the 10T½ cell lines (FIG. 22c). They had a lower saturation density than vector controls (FIG. 23) and suppressed rates of locomotion compared to transformed parental C3 tumor cells (Table 4). In contrast to empty vector controls, the cells failed to form foci in monolayer culture (FIG. 24) and did not form colonies in soft agar (Table 4). When injected subcutaneously into syngeneic mice, no tumors were detected after 6 months of observation (FIG. 25 [3 and 4]). Empty vector controls and the parent cell lines formed large tumors within 3 weeks (FIG. 25 [2 and 1]). In addition, the clones expressing mutated RHAMM did not develop tumors in the lung colonization assay for metastasis (FIG. 26, lower panel).

The present invention provides a method for controlling or preventing the proliferation of tumour cells by treatment with soluble RHAMM protein. Treatment with soluble RHAMM reduces or prevents the tumorigenicity and the metastatic capability of tumour cells.

"Soluble RHAMM protein" includes RHAMM II, RHAMM I and RHAMM I-2a.

The present invention provides a new therapeutic method and new pharmaceutical compositions for cancer treatment.

Administration of a pharmaceutical composition comprising soluble RHAMM protein to a mammal having a tumour,. including a human cancer patient, may be carried out by any of the usual methods known to those skilled in the art for administering anti-tumour agents. For example, the composition may be administered intravenously or by direct injection into the tumour.

A further therapeutic approach is to genetically manipulate a patient's tumour so that the tumour cells themselves commence or increase expression of soluble RHAMM, thereby controlling or preventing proliferation of the tumour cells. It is within the skill of those knowledgeable in the art to fashion a DNA construct comprising an appropriate cDNA encoding a RHAMM protein along with a suitable signal sequence so that the expressed RHAMM protein is secreted from the cells in soluble form.

Although the therapeutic methods and pharmaceutical compositions of the invention are not limited by the mechanism presently proposed for the action of soluble RHAMM, it is believed that the observed anti-tumour effect of soluble RHAMM is a result of the binding of soluble RHAMM to cell surface-associated RHAMM on the tumour cell surface, so as to prevent the binding of HA and the resulting signal transduction via protein kinase C, SrC and focal adhesion kinase.

Treatment with soluble RHAMM will be effective to prevent or control any disorder arising from unwanted or excessive stimulation of cell-associated RHAMM.

The methods and compositions described herein provide a means of modulating the activity of the RHAMM-regulated signal transduction pathway and of preventing or treating disorders associated with or characterised by an abnormality of that pathway by modulating the interaction of cell-associated RHAMM with its ligand.

It is believed that soluble RHAMM and cell-associated RHAMM bind by interaction of their repeat sequences, which are encoded by nucleotides 760 to 1071 of FIG. 2.

Antisense RHAMN Confers Resistance to Transformation by Mutant H-ras

Figure 30A:
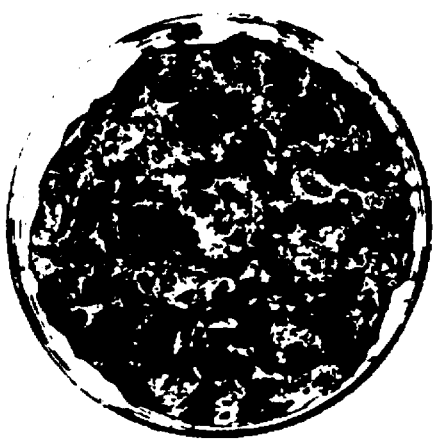
Figure 30B:
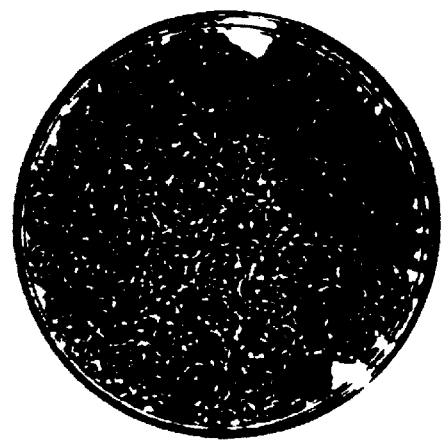
Figure 30C:
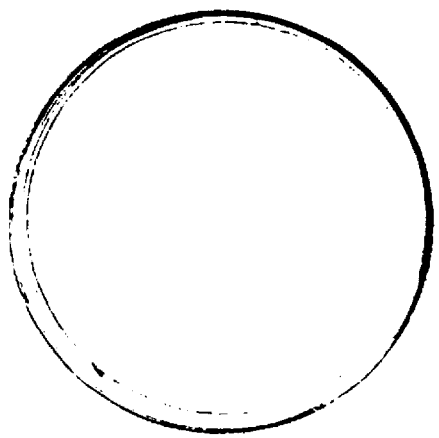
Figure 30D:
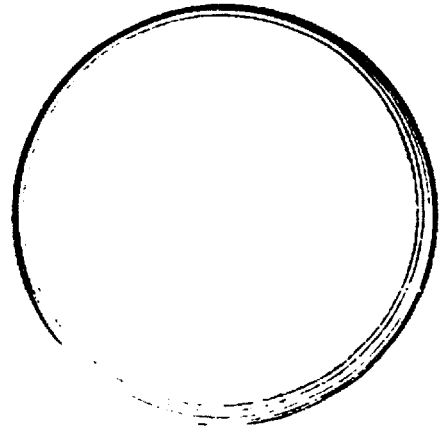

To determine whether fibroblasts with suppressed RHAMM expression could be transformed with ras, 10T½ cells were transfected with RHAMM cDNA in an antisense orientation using the vector illustrated in FIG. 27. Two G418 resistant clones (termed OR1 and OR2) that expressed 0 to 10% of the detectable RHAMM protein levels seen in vector controls were selected from over 60 clones with varying reductions of RHAMM expression (FIGS. 28A and B). The two clones expressing low levels of RHAMM protein were identical in their properties. The presence of RHAMM antisense and the reduction or lack of RHAMM message was demonstrated by RT-PCR (FIGS. 29A and B) and confirmed by Northern blot hybridization (data not shown). Antisense PCR product of OR1 was sequenced for confirmation. The two transfected cell lines, the empty vector control and the parent 10T½ cells were then grown to confluence and transfected with mutated H-ras. The parental line and the vector control formed multiple large and small foci after three weeks in culture (FIGS. 30A and B), whereas cultures containing the OR1 and OR2 constructs formed no foci (FIGS. 30C and D). Furthermore, these clones, unlike ras-transformed controls, retained a flat morphology. All ras-transfected cultures expressed $p21^{ras}$ protein (FIG. 31) at levels similar to those of C3 (FIG. 21).

EXAMPLES

Example 1

Isolation of Genomic Clones and Sequencing

RHAMM genomic clones were isolated by screening a mouse fibroblast genomic library in the lambda Fix II vector with the RHAMM II cDNA clone (Hardwick et al., 1992) as a probe. The probe was labelled with $^{32}p$ using the random oligonucleotide primer kit (Pharmacia, Piscataway, N.J.). Filters were hybridized overnight in 5×SSPE (1×SSPE is 150 mM NaCl, 1 mM $NaH_2PO_4$ and 1 mM EDTA (pH 7.5), 5×Denhardt's solution (1×Denhardt solution is 0.02% Ficoll, 0.02% polyvinylpyrrolidone and 0.02% bovine serum albumin, 0.2% sodium dodecyl sulphate) and 100 µg/ml denatured salmon DNA for 16 h at 65° C. Membranes were washed at 65° C. with 2×SSC, then 1×SSC and 0.1×SSC for a total of 90 minutes (1×SSC is 150 mM NaCl, 15 mM sodium citrate pH 7.0 and 0.1% SDS) and autoradiographed at −80° C. Positively hybridizing recombinant bacteriophage were plaque purified and phage DNA was prepared as described previously (Sambrook et al., 1989).

Restriction Endonuclease Mapping of the Genomic Clones

Phage DNA were digested with restriction endonucleases and the resulting fragments were separated on 0.9% agarose gels. After denaturing they were transferred to nylon membranes for Southern blotting. Filters were hybridized with the randomly labelled RHAMM II cDNA as a probe. Hybridization and washing conditions were as previously described. Detailed restriction maps of each lambda clone were made and selected restriction fragments were then either subcloned and sequenced using the T7 sequencing kit (Pharmacia, Piscataway, N.J.) or the cycle sequencing kit (Gibco BRL Gaithersburg, Md.) following the strategy depicted in FIG. 4. Sequencing primers were made using RHAMM II cDNA as a reference. Introns were sized either by sequencing or by using exon/intron flanking sequence to amplify the introns, using the polymerase chain reaction (PCR), followed by sizing on 1% agarose gels. PCR reactions were carried out as described below for the 5' rapid amplification of cDNA ends (RACE), except that lambda clones were used as a DNA template and 30 cycles of amplification were used.

Five genomic clones were isolated; their restriction digests indicated that the clones were overlapping (FIG. 4E). PCR analysis of these clones using primer at the start of AUG 2 (5' ATGCAGATCCTGACAGAGAGG 3') (SEQ ID NO:42) and a primer complementary to the end of intron 3 (5'CTGCATTCAGACAGGTAAGCA 3') (SEQ ID NO:43) produced one fragment of the same size for each clone, confirming that they contained overlapping regions. Sequencing the PCR products confirmed that a core fragment was identical in each clone. The entire RHAMM gene (FIG. 4E) was contained in clone 1 and clone 4. The PCR products and nucleotide sequencing strategy used to determine the RHAMM gene structure is shown in FIG. 4 and the sequence of the entire coding regions and exon/intron boundaries are shown in FIGS. 1 and 2.

Using the RHAMM II cDNA clone for reference, the gene was determined to be organized into 14 exons interrupted by 13 introns spanning 26 kilobases of DNA (FIG. 4). The exons range in size from 60 bp (exon 1) to 1.1 kb(exon 12) (Table 1). The intron sizes vary considerably, ranging from 90 bp (intron 1) to 6500 bp (intron 2) (Table 1).

The deduced amino acid $AA^{124-229}$ sequence encoded in the RHAMM II protein (Hardwick et al, 1992) which comprises five perfect repeats of 21 amino acids occurs in one exon (exon 6). The two HA binding domains (Yang et al., 1993) are encoded in exons 10 and 11 separated by a 2.2 kb intron (FIG. 4D).

Isolation of DNA and Southern Blots

High molecular weight DNA was isolated from 3T3 fibroblast cells (Sambrook et al., 1989). Approximately $5 \times 10^6$ cells were washed twice with Tris-buffered saline, removed from the culture dish by scraping and centrifuged at 1000 g for 5 min. Mouse genomic DNA was isolated by proteinase K-SDS as previously described (Sambrook et al., 1989). DNA samples were incubated with restriction endonucleases and electrophoresed through a 0.7% agarose gel and transferred onto a nitrocellulose membrane. The membrane was hybridized with randomly labelled RHAMM II cDNA. Hybridization and washing conditions were exactly as described above for the isolation of genomic clones. The restriction pattern obtained is shown in FIG. 3 and is consistent with the RHAMM gene being a single copy gene.

Cloning RHAMM I cDNA

Two μg of cytoplasmic RNA from 3T3 fibroblasts was subjected to first strand cDNA synthesis as described in the cDNA first strand synthesis kit (Clontech Palo Alto, Calif.). A primer from thee start of exon 1, 5'GCGGTCGACAT-GAGAGCTCTAAGCCTGGAA 3' (SEQ ID NO:59), and one from the 3' non coding region of RHAMM II, 5' CGCGGATCCCCTTTGGTGATGAACAGCAG 3' (SEQ ID NO:60), were used to amplify a 2.2 kb fragment. The primers contained a Sal 1 and a BamH1 restriction site respectively to facilitate cloning into the expression vector (pH βAPr-1-neo) (Gunning et al., 1987) which contained a neomycin resistance gene for selection. The plasmid construct was sequenced and subsequently stably transfected into 10T½ fibroblasts using the lipofection kit (Gibco, BRL, Gaithersburg, Md.). Selected clones were analyses by Western analysis for protein size and elevated RHAMM expression, at confluence, using the anti-RHAMM antibody R.3.2 (Hardwick et al., 1992).

Rapid Amplification of cDNA Ends (RACE)

The 5' sequence of the RHAMM transcript was cloned using the rapid amplification of cDNA ends (RACE) technique. Briefly, an oligonucleotide complementary to residues 490–469 of the existing RHAMM II cDNA was used to prime cDNA synthesis from 3T3 fibroblast mRNA, as described in the 5' amplifinder RACE kit protocol (Clontech, Palo Alto, Calif.). A single stranded oligonucleotide anchor was then ligated directly to the 3' end of the first strand cDNA. Following ligation, the cDNA template was used for polymerase chain amplification (PCR) using a primer complementary to the anchor and a nested gene specific primer complementary to residues 81–60. PCR cycling parameters were denaturation at 94° C. for 4 min, denaturation at 94° C. for 45 sec, annealing at 55° C. for 45 sec and extension at 72° C. for 2 min. 35 cycles were used with a final extension time of 7 min. PCR amplification yielded a faint band of 350 bp. Reamplification using the same primers and conditions yielded a strong band of 350 bp which was then directly sequenced using cycle sequencing.

Mapping the 5' End by Primer Extension

Primer extension assays were performed with $^{32}$P-end-labelled oligonucleotide primers as described (Sambrook et al. 1989), using the following two primers: A 22-mer primer (5'-TTCCAGAGCCAGCCTCTCTGT-3') (SEQ ID NO:44) complementary to the region of RHAMM II located 34–59 bp 3' of AUG 2; A 25-mer primer (5'-TCATCTTTGTCTCTCTCTTATTTCT-3') (SEQ ID NO:45) complementary to the region of RHAMM 1 located 11–36 bp 3' of AUG 1. Primers complementary to 5'-untranslated regions of RHAMM I and RHAMM II were radiolabelled at their 5' termini, hybridized to total RNA isolated from 80% confluent cultures and extended with reverse transcriptase. Products were separated on 6% sequencing gels adjacent to sequencing reactions (Lane a,c,g and t) for sizing. Six ng of end labelled primer were hybridized with 15 μg total RNA from C3 cells. The extension reaction was done with 20 units AMV reverse transcriptase (Clontech, Palo Alto, CA) for 1.5 hr at 42° C. The same primer was used on cloned genomic DNA template to generate dideoxy sequencing ladders for sizing the primer extension initiation sites. Results are shown in FIG. 8.

In Vitro Translation

The messenger RNA, obtained from 3T3 cells with Pharmacia Quick-Prep mRNA Purification kit, was translated into protein using rabbit reticulocyte lysate (Amersham Oakville, Ontario) and $S^{35}$-L-methionine-$S^{35}$-L-cysteine mix, (TRAN$^{35}$S-label)(ICN, Mississauga, Ontario). Tobacco mosaic virus was used as a positive control. One μl RNA guard (Pharmacia 27-0815-01) was used to protect the 50 μl reaction mixture during incubation at 30° C. for 90 min. One μl was precipitated onto a glass filter and counted in scintillation fluid for the confirmation of Trans $^{35}$S-label incorporation. The remaining reaction mixture was immunoprecipitated with normal rabbit IgG or the anti-RHAMM peptide antibody as described (Hardwick et al., 1992; Yang et al., 1993). The resulting samples were run on a mini-gel, fixed and subjected to fluorography.

Northern Blot Analysis

Total RNA was extracted from 80% confluent 3T3 fibroblasts using the guanidinium thiocyanate method (Sambrook et al., 1989). Eighty Ag of total RNA was electrophoresed in a 1.3% agarose gel, transblotted onto Hybond N$^+$ membrane and hybridized with $^{32}$P-labelled RHAMM II cDNA as a probe (Hardwick et al., 1992). The hybridization was carried out in 5×Denhardt's solution, 10% (w/v) Dextran solution, 50% formamide and 50 μg/ml denatured Salmon sperm DNA at 42° C. overnight (Sambrook et al., 1989). Washing conditions were 2×SSC and 0.1% SDS, then 1×SSC and 0.1% SDS and finally 0.1×SSC and 0.1% SDS at 42° C. for a total of 30 min. The blot was exposed to Kodak X-Omat film at −80%C for 1–2 days.

Western Blot Analysis

Eighty percent confluent cultures were lysed in RIPA buffer (Sambrook et al., 1989) and solubilized protein was quantified with a protein assay kit (Biorad Mississauga, Ontario). Ten μg of protein was electrophoresed in SDS-PAGE and transferred electrically to nitrocellulose membranes. Remaining protein binding sites on the membrane were blocked with 5% defatted milk and the membranes were incubated with 1:1000 dilution anti-RHAMM antibody, R.3.2 (Hardwick et al., 1992). Membranes were washed in Tween (0.05%)-Tris-buffered saline (TTBS); probed with the second antibody (goat anti-rabbit-HRP) and visualized by the chemiluminescence method (Amersham Oakville, Ontario).

Example 2
Transfection of RHAMM I-2a and RHAMM II cDNA

The RHAMM I-2a and RHAMM II cDNAs were inserted into the pHβAPr-1-neo vector (Gunning et al., 1987) containing a neomycin resistance gene for a selection marker. 10T½ fibroblasts were transfected with the plasmid using a lipofectin kit (Gibco BRL, Gaithersburg, Md.). Cells were selected in G418 and cloned. Clones were analyses for increased RHAMM expression at confluence by Western transblot analysis using the anti-RHAMM peptide antibody (Hardwick et al., 1992). Fifteen μg of protein were loaded per Lane. Transfections using the vector (pHβAPr-1-neo) alone were used as a control. Fifteen clones of each transfection were obtained that overexpressed RHAMM by 2–3 fold as determined by densitometric analysis of Western blots. Three clones of each transfection were then characterized in detail.

Isolation of RHAMM from the Supernatant Media

10T½ transfected cells were grown to confluence. Ten ml of supernatant medium was collected, concentrated to 2 ml and desalted using centripreps (Amicon, Oakville, Ontario) and Affi-gel Blue buffer (0.1M $K_2HPO_4$, 0.15M NaCL pH 7.25). The 2 ml concentrate was further concentrated to 1 ml using centricons (Amicon, Oakville, Ontario) and protease inhibitor (1 μM leupeptin, 1,000 KU/ml Aprotinin, 1 μg/ml PMSF and 1 mM sodium orthovanadate) was added. The 1.0 ml concentrated sample was then added to a 1.0 ml Affi-gel Blue (Biorad) column to remove BSA. Fifteen mg of protein were used for Western analysis, using 1:1000 dilution anti-RHAMM peptide antibody R10.1 (Hardwick et al., 1992).

Example 3
Focal Adhesion

The ras-transformed 10T½ cells termed C3 (Egan et al., 1987) were grown on fibronectin coated glass coverslips for 24 hrs. The cells were then exposed to RHAMM I-2a (1 ng/ml to 1 mg/ml) for 2 hrs at 37° C. before fixing with 3% paraformaldehyde/phosphate buffered saline (PBS). Cells were then washed three times with 10% fetal calf serum PBs, permeabilized with 0.2% triton X-100/PBS for 3 min, and washed again. The coverslips were then incubated with anti-vinculin (Sigma, 1:75 dilution) or an identical concentration of nonspecific mouse IgG for 1 hr at 37° C. After washing, the coverslips were incubated with rhodamine labelled goat anti-mouse antibody (1:200, Sigma) for 2 hrs at room temperature. After further washings, the coverslips were mounted on glass slides and viewed on a Zeiss Axiovert 35 M fluorescent microscope.

Results are shown in FIG. 12.

Example 4
Fibroblast Transformation Resulting from Over-expression of RHAMM (a) Methods

Cell Culture and Cell Lines

The murine fibroblast cell line 10T½ was cultured in alpha-minimal essential medium (aMEM, Gibco, Grant Island, N.Y., USA) containing 10% dialyzed calf serum (Gibco) as described previously (Samuel et al., 1993). The calf serum was dialyzed against 10 volume of 0.8% sodium chloride for 10 changes in dialysis tubing with a 12,000–14,000 molecular weight cut-off (BRL, Gaithersburg, Md., USA).

Timelapse Cinemicrography

To monitor random locomotion, $6 \times 10^4$ cells were plated in 25 $cm^2$ tissue culture flasks 24 hours prior to measurement. Cell locomotion was quantified using an IM 35 inverted microscope (Zeiss, Germany) to which a video camera (Hamamatsu CCD, Inc., Japan) was attached. The cells were maintained at 37° C. using a heated platform (TRZ 3700, Zeiss, Germany). Motility was measured using image analysis (Image 1, Universal Imaging Corp., Westchester, Pa., USA). This program allows quantification of nuclear displacement in a sequence of digitalized images.

The baseline random locomotion of each cell line was measured for a period of 1.5 hours with images obtained at 20 minute intervals. Antiserum specific to RHAMM (see below) was added at a dilution of 1:300 and motility was again measured for a further 1.5 hours in the same manner. The mean cell velocity of 15 cells per measurement period was calculated. Control experiments, performed simultaneously on cells passaged at the same time and at the same cell density, used normal IgGT (Sigma Chemical Co., St. Louis, Mo., USA) in place of anti-RHAMM antiserum.

Anti-RHAMM Antiserum

A polyclonal antiserum (anti peptide$^{aa268-288}$ antiserum, Hardwick et al., 1992) was raised in rabbits to a specific peptide$^{aa268-288}$ encoded in the RHAMM cDNA. The antiserum has previously been shown to recognize only recombinantly expressed RHAMM proteins containing the amino acid sequence to which it was raised. In addition, preincubation of the antiserum with complete RHAMM fusion protein blocks the recognition of RHAMM in Western blots, and preabsorption of the antiserum on a Sepharose-RHAMM fusion prevents immunostaining for RHAMM in tissue sections.

Flow cytometry

Cells were harvested using Hank's Balanced Salt Solution (HBSS) plus 20 mM Hepes, 0.05% sodium azide and 2.0 mM EDTA for 5 minutes, and were maintained at 4° C. throughout the procedure. The cells were washed in the same solution lacking only EDTA, and then incubated with anti-peptide$^{aa268-288}$ antiserum (1:50 dilution) for 30 minutes. Following this, the cells were incubated with fluoroscein-conjugated goat anti-rabbit antiserum (1:300 dilution, Sigma) for a further 30 minutes and were then fixed with 3% paraformaldehyde. The surface expression of RHAMM was studied using immunofluorescence flow cytometry. Normal IgG was used as a control at each time point analyzed.

Western Blots and HA Binding Assay

Proteins were electrophoresed on 10% SDS-PAGE gel and transblotted onto a nitrocellulose membrane in a Tris-HCl buffer containing 25 mM Tris, 192 mM glycine and 20% methanol, pH 8.3 at 80 v for 1 h in a cold room. The membrane was blocked in TBSTS (10 mM Tris-Cl, pH 8.0, containing 150 mM NaCl, 0.05% Tween 20 and 5% skim milk powder) for 1 h at room temperature and then incubated with anti-RHAMM antibody (R3.0), diluted in TBSTS (1:2000) overnight at 4° C. The membrane was washed with TBST extensively and then incubated with an appropriate second antibody diluted in TBSTS. Antibody binding was visualized with chemiluminescence according to kit instructions (ECL Kit, Amersham), using luminal and hydrogen peroxide to visualize the bound antibody.

For the HA-binding assay, cell lysates were separated on SDS-PAGE, transblotted onto nitrocellulose membranes, then blots were incubated with biotinylated HA instead of primary antibody (Yang et al., 1993). Streptavidin-peroxidase conjugate (Sigma) was used as a second antibody, and blots were processed as above.

Northern Assays

Total RNA was extracted from confluent cells by lysing cells in a buffer containing 4 M guanidinium thiocyanate, 0.1 M Tris-HCl, 1% β-mercaptoethanol, pH 7.5 for 10 min at room temperature. The lysate was centrifuged at 13,000 rpm for 15 min. The supernatant (1.5 ml) was loaded into an ultracentrifuge tube that contained 5 ml of 5.7 M CsCl, 0.01 M EDTA (pH 7.5) and centrifuged at 38,000 rpm (Ti 70) for 20 h at room temperature. The pelleted RNA was dissolved in 500 µl DEPC-treated dd H$_2$O and incubated at 65° C. for 20 min. The undissolved materials were pelleted at 13,000 rpm for 10 min and removed. The RNA was concentrated by three volumes (v/v) of absolute ethanol, washed with 75% ethanol and dissolved in DEPC-treated ddH$_2$O. 60 µg of total RNA was electrophoresed in 1.3% agarose gel, transblotted on Hybond N$^+$ and hybridized with RHAMM cDNA (Samuel et al., 1993) as a probe. The hybridization was carried out in a buffer containing 5×SSPE, 5×Denhardt's solution, 10% (w/v) Dextran sulphate, 50% (v/v) formamide and 0.5 mg/ml denatured non-homologous DNA at 42° C. overnight. Non-specific binding was removed from the membrane with 2×SSPE, 1×SSPE, 0.5×SSP and 0.1×SSPE at 42° C. for 4×30 min. The blot was then exposed to Kodak Xomat film at −80° C. for days.

(b) Transfection of 10T½ Cells with the RHAMM Gene

The RHAMM gene from intron 2 to exon 12 was isolated from a 3T3 cell line genomic library as in Example 1. The gene for RHAMM, harboured in EMBL3 phage arms, was cotransfected with PSV$_2$ plasmid into 50% confluent fibroblast 10T½ cells with CaPO$_4$ precipitation in DMEM as described (Felgner et al, (1987) P.N.A.S. U.S.A., 84: 7413–7). The transfected cells were selectively grown in DMEM medium containing 10% dialyzed calf serum and 0.6 mg/ml geneticin (G418) for 3 weeks. The selecting medium was changed every 3 days. G418 resistant colonies were cloned by selectively trypsinizing colonies using a micropipet tip containing 1 µl of trypsin (from DIFCO, 1:50 dilution) containing 2 mM EDTA, then cloning by limiting dilution. Fifteen clones were isolated. Cell lysates of clones were prepared and screened with antibody to RHAMM (R3.0) in a Western blot assay. Five clones overexpressing RHAMM were selected for further studies.

To assure that the RHAMM gene was stably integrated into the cell genome, total DNA, prepared as described in Sambrook et al., 1989, was digested with several restriction endonucleases described below, separated on 0.8% agarose gel and transblotted onto Nylon Hybond N$^+$ membranes in 0.4 M NaOH. The Hybond N$^+$ membranes were then probed with 1) RHAMM cDNA using DNA that was digested with HindIII and SalI, 2) left arms of phage vector, using DNA that was digested with PvuI, BglII and BamHI, and 3) right arms of phage vector using DNA that was digested as in 2). The hybridization was carried out at 65° C. in a solution containing 6×SSC, 5×Denhardt's solution, 0.5% SDS, and 20 µg of denatured salmon sperm DNA/ml hybridization solution overnight as described (Sambrook et al., 1989). The membranes were washed at 65° C. with 2×SSC, 1×SSC+0.1% SDS, 0.1×SSC+0.1% SDS (30 min for each washing) and exposed to Kodak Xomat film as described (Sambrook et al., 1989).

(c) Transfections with RHAMM cDNA's

Cell lines were transformed by transfection with either H-ras or RHAMM I-2a cDNA as described in (b) above. Plasmid pH06Ti contains T24 H-ras linked to the aminoglycoside phospho-transferase gene to confer resistance to G418 (Egan et al., 1987) and RHAMM I-2a was cloned into the pHβAPr-3-Neo expression vector (Gunning et al., 1987).

Transfections were accomplished using CellPhect kits (Pharmacia, Uppsala, Sweden). A total of 2×10$^5$ cells were transfected 18 h after subculture. A 120 µl aliquot of buffer containing 0.28 M sodium chloride, 0.05 M Hepes and 0.75 mM sodium hydroxide phosphate was added, mixed and incubated for 15 minutes at room temperature. The calcium phosphate-DNA precipitate was added to cells on culture plates, which were then incubated for 6 h at 37° C. in a humidified 5% carbon dioxide atmosphere. The culture plates were then washed with growth medium (α-MEM, plus 10% dialyzed calf serum) and then treated with 1.5 ml of 15% glycerol in isotonic Hepes, pH 7.5, for 3 minutes, and then washed again and replenished with fresh growth medium. Transfection of 10T½ cells was carried out with 0.4 µg of pH06Ti, or transfection with 2 µg of pHβAPr-3ρ-neo plasmid.

(d) Construction of a RKAMM Dominant Negative cDNA by Site-directed Mutagenesis of the HA Binding Domain Mutagenesis of specific basic amino acids in both of the HA binding domains of RHAMM were generated in two steps. In the first step, site-directed mutations were confined to basic amino acids K$^{405}$ and K$^{409}$. In the second step, the basic amino acids, also 430–432, previously shown to be critical to HA binding were mutated using the RHAMM cDNA in Step I. These mutations abolished the HA binding ability of both domains (Yang et al., 1994).

(e) Focus Formation

Cells were grown to 50% confluence and transfected with RHAMM constructs or H-ras with CellPhect, as described above. The transfected cultures were grown in a DMEM medium containing 20% FBS. The medium was changed every 3 days for up to 4 weeks until foci formed. Foci that were detectable with methylene blue staining were counted.

(f) Determination of Culture Monolayer Density

Cell density assays were carried out in 24-well plates and conducted by inoculating 5×10$^4$ cells in each well together with 1 ml DMEM medium supplemented with 10% FCS and 0.6 mg geneticin. Cultures were maintained at 37° C. and 5% CO$_2$ and the medium was changed every three days. At each time point, cells were harvested by trypsination 10–25% and cell concentrations were determined by counting cells in a Colter counter.

(g) Growth in Soft Agar

5×10$^3$ cells/ml were plated in AMEM containing 10% FBS on to bactoagar (1.25%) for 7–10 days. Colonies of cells were counted/plate. The plating efficiency of each cell line was similar (75%). Values represent the mean of 6 replicates±S.E.M.

(h) Transfection of RRAMM Antisense cDNA Expressing Clones

RHAMM cDNA (Hardwick et al., 1992) was used as a PCR template to generate a 1.7 kb fragment containing the entire coding region (amino acid 1 to 477) and 172 nucleotides of 3' flanking sequence. The fragment was cloned in an antisense orientation into the pHβApr-3P-Neo expression vector (Gunning et al., 1987). The PCR product was sequenced for confirmation.

To produce stably transfected cell lines, 10T½ fibroblasts using lipofectin were transfected with RHAMM antisense plasmid constructs according to the manufacturer's instructions (Gibco BRL, Gaitherburg, Md., USA). Briefly, 1–2×10$^5$ of the 10T½ cells were seeded into 60 mm tissue culture dishes and cultured in growth medium containing DMEM and 10% fetal bovine serum. After reaching 50–70% confluence, cells were transfected with 10–20 µg of RHAMM plasmid or the empty vector PY3 plasmid containing hygromycin B gene. The transfected cells were subsequently cultured in growth medium and selected with 0.6 mg/ml G418 (for 10T½) or 0.2 mgml hygromycin (for C3 cells, which contain a neomycin resistance gene).

(i) Tail Vein Assay and Tumor Formation

Cells were grown to confluence, washed with Hanks and released from the substratum in Hanks containing 2.5 mmi EDTA. If cells did not release (i.e. 10T½ cells) they were scraped from the substratum with a rubber policeman. Exclusion of trypan blue indicated that >90% of cells were viable. C3 female mice were injected with $1–5 \times 10^6$ subcutaneously into the right hind leg and maintained for 3–6 weeks when tumors routinely become apparent. Animals were euthanized and tumors were removed, weighed and pieces processed for histology using paraffin embedding techniques.

For experimental metastasis assays (Egan et al., 1989) $5 \times 10^5$ cells were injected into the tail vein. In some animals, the lungs were removed aseptically 24 hr after injection and explanted into 60 mm culture dishes in the presence of 5 mg/ml of geneticin. Cells that migrated out of the lungs were trypsinized and subcultured. The remainder of the mice were maintained for six weeks, euthanized, lungs removed and occurrence of tumor nodules assessed by processing tissue for histology and examining tissue sections for tumour nodules.

(j) RT-PCR and Southern Blotting

Reverse-transcriptase-PCR was utilized to determine the presence of RHAMM sense and antisense transcripts and was carried out using MMLV reverse transcriptase and the 1st strand cDNA synthesis kit (Clontech, Clontech Lab, Inc., CA). Briefly, total RNA was isolated from parent and transfected cell lines using the guanidinium method (Kingston et al., 1993). RHAMM sense and antisense cDNA were synthesized on 1 μg total RNA template by using an oligo dT and the primer 5' . . . GGA TCC AGT ACT TCT GAG AAG AAC GTC TTT A (SEQ ID NO:46). An aliquot of the synthesized cDNA was used as the template for subsequent PCR amplification. Primers 5' AGT GGA TCC CAA GCC ATC TTG AT GCA CAA GAG (SEQ ID NO:47) and 5' TGG AGT AAA ATT CTC CTT AGA (SEQ ID NO:48) were used for synthesizing RHAMM sense fragment and 5' AAA TAG AAG ATC TTA AAC TGG (SEQ ID NO:49) and 5' TGG AGT AAA ATT CTC CTT AGA (SEQ ID NO:50) for the antisense fragment. The PCR reaction was performed in the order of 94° C. (45 sec), 56° C. (45 sec) and 72° C. (2 min) for 30 cycles. The PCR products were electrophoresed on 1.0% agarose gel and stained with ethidium bromide. The occurrence of sense and antisense fragments were confirmed by Southern blot analysis using RHAMM cDNA as a probe (Hardwick et al., 1992).

Example 5

(a) Competitive Displacement ELISA

A 200 μg/ml HA solution in $H_2O$ was heated at 100° C. for 40 min. to eliminate any residual binding of possible contaminating HA binding proteins. The cooled solution was diluted at 1:1 with 0.2 M sodium carbonate. Nunc ELISA microtitre plates (covalink) were coated with the HA solution (250 μl/well) overnight at 20° C. The wells were washed and then incubated with 250 μl of 5% or 0.5% defatted milk in 0.1 M sodium carbonate (pH 9.0) overnight at 20° C. Two hundred μl of the purified 58 kDA RHAMM protein (1.25 μg/ml phosphate buffered saline) was allowed to react with $0–10^{-7}$ μM of intact HA, chondroitin sulphate or heparin polymers, as well as hexasaccharides of HA or buffer alone at 20° C. for 1 h. The mixture was then added to the HA coated surfaces for 2 h at 4° C. The plates were washed three times with 0.01 M sodium phosphate/0.15 M NaCl at pH 7.4, and then incubated with a non-blocking Mab, shown to be specific for the 58 kDa protein (3T3-7 1 μg/ml, Hardwick et al., 1992), overnight on a gyratory shaker at 4° C. The plates were again washed and then incubated with goat anti-mouse IgG coupled to alkaline phosphatase for 1 h. Bound IgG was detected by NBT-BCIP (Bertrand and Delpech, 1985). Absorbance was measured at 405 nm on a Pharmacia multiscan ELISA plate reader.

(b) Cell Locomotion Assay

For motility experiments, $10^5$ cells were subcultured into 25 $cm^2$ tissue culture flasks (Corning), and maintained for 12 h as above. The medium was then aspirated, cells were rinsed with Hanks Balanced Salt Solution (HBSS) (Gibco) and fresh, serum-free α-MEM containing 4.0 μg/ml transferrin (Gibco) and 2.0 μg/ml insulin (Sigma) (defined medium) was added to the flasks.

Cell locomotion was recorded using a computerized time-lapse analysis system (Image 1, Universal Imaging Corporation, Westchester, Pa.) that measures nuclear displacement. During the filming period, cells were maintained at 37° C. in defined-media at physiological pH.

(c) Cell Culture and Radiolabelling with $^{35}S$-Methionine

The 10T½ fibroblast cell line transfected with H-ras and $neo^R$ genes, termed C3, has previously been described (Egan et al., 1987). C3 fibroblasts were maintained at 37° C. and in 5% $CO_2$ on plastic tissue culture dishes (Corning Glassworks, Corning, N.Y.) in alpha-modified Eagles medium (α-MEM) supplemented with 10% fetal calf serum (FCS) (Hyclone, Gibco, BRL, Burlington, ON) and 10 mM HEPES (Sigma Chemical Co., St. Louis, Mo.) pH 7.2. Cells were subcultured using 0.25% tryspin/2 mM EDTA when the cultures reached 80% confluence.

For metabolic labelling studies, C3 fibroblast cells were grown to 80% confluence, rinsed with PBS and then DMEM. The cells were incubated with 1 ml/well DMEM containing 5% FCS at 37° C. for 1 h and trans-methionine 35Slabel (1 mCi/ml, Amersham) for a 10 min pulse. $^{35}S$-label in the medium was removed and the cells were washed. DMEM containing 10% FCS (1 ml/well) was added to each well as a chase. The "chase" medium was removed at 0, 5, 10, 15, 20, 30 and 60 min and radiolabelled RHAMM accumulated in the medium was immunoprecipitated with an anti-RHAMM antibody prepared against a sequence encoded in the RHAMM cDNA (Hardwick et al., 1992). The immunoprecipitates were electrophoresed on SDS-PAGE and the gel was dried, then exposed to Kodak X-Omat film to detect the proteins incorporating $^{35}S$-methionine.

As seen in FIG. 32, a 90–100 kDa protein was rapidly secreted into the growth medium, significantly accumulating by 20 minutes after the chase. Secreted RHAMM was collected in the spent culture medium of C3 cells, then chromatographed on an anti-RHAMM and hyaluronan-Sepharose affinity column. The protein was then separated with high performance electrophoresis (32B) and the resulting eluted protein was then electrophoresed on SDS-PAGE and the gel stained with silver (32A). This method of purification allowed isolation of a single protein band of $MW_E$ 100 kDa. The $MW_E$ of the arrows are 200, 120, 84 and 45 kDa respectively.

Hyaluronan was absorbed to ELISA plates and then incubated with purified RHAMM (FIG. 32C) in the presence or absence of $0-10^{-7}$ μM of hyaluronan (○-○) and hexasaccharides of hyaluronan (◆-◆). Plates were washed, then incubated with a non-blocking monospecific monoclonal antibody. Values represent the means of 5 replicates.

(d) Collection of RHAMM from Supernatant Media

3T3 fibroblasts and 10T½ transfected cells (C3) were grown to confluence. 10 ml samples of supernatant media were collected and concentrated to 2 ml and desalted using centripreps (Amicon, Oakville, ON) and Affi-gel Blue buffer (0.1M $K_2HPO_4$, 0.15M NaCL pH 7.25). The 2 ml concentrate was further concentrated to 1 ml using centricons (Amicon, Oakville, ON) and protease inhibitor was added (Turley et al., 1987). The 1.0 ml concentrated sample was then added to a 1.0 ml Affi-gel Blue (Biorad) column to remove BSA Fifteen μg of protein were used for Western analysis, using 1:1000 dilution anti-RHAMM antibody R3.2 (Hardwick et al., 1992).

(e) Removal of RHAMM from Spent Medium

RHAMM was removed from culture medium from subconfluent ras-transformed fibroblasts by modifying a method of de Wet et al., (1984) for IgG purification. Polyclonal antibodies to RHAMM fusion protein raised in rabbit were bound to cyanogen bromide-activated Sephanose 4B with end-over-end mixing at 4° C. overnight. The mixture was packed into a column. The unbound active sites of the gel were blocked by flushing the column with excess 0.1 M sodium bicarbonate, pH 8.3, containing 0.5 M NaCl at a flow rate of 50 ml/h, followed by washing with 1 M Tris-Cl, pH 8.0 at the same flow rate. Unbound polyclonal antibodies were removed with successive cycles of washing with 0.1 M sodium bicarbonate buffer, pH 8.3, and 0.1 M sodium acetate buffer, pH 4.0 (each containing 0.5 M NaCl). The processed gel was then incubated with spent culture medium for 30 min at room temperature to absorb soluble RHAMM from the medium.

(f) Effect of RHAMM Removal on Cell Locomotion

RHAMM-free medium prepared as in (e) above was added to subconfluent monolayers of C3 fibroblasts and cell locomotion was determined using image analysis, as described above. Spent culture medium chromatographed over a Sepharose column and medium with added RHAMM fusion protein were applied to similar cultures as controls. As seen in FIG. 33, removal of RHAMM from spent growth medium significantly enhanced cell locomotion ($p<0.0001$) relative to controls.

(g) Effect of HA-Binding Peptides on Cell Locomotion

A 10 amino acid peptide corresponding to one of the HA binding domains of RHAMM, peptide$^{aa423-432}$ (Yang et al., 1993), was synthesised and added at various concentrations (0,0.1, 1.0, 5.0, 10.0 and 50.0 ng/ml) to 70% confluent C3 fibroblasts. Cell locomotion was monitored by image analysis for 2 h from the addition of the peptide. A scrambled peptide was used as control.

As seen in FIG. 34, peptide$^{aa423-432}$ significantly inhibited cell locomotion at 5 ng/ml ($p<0.001$) and higher. Control peptide had no effect (data not shown).

Example 6

(a) Truncations of RHAMM cDNA and Construction of RHAMM-GST Fusion Protein

RHAMM II cDNA was cloned into pGEX-2T plasmid and the recombinant plasmid was truncated with Sac 1 restriction enzyme as described previously (Yang et al., 1993) and transformed into HB101. RHAMM cDNA was isolated from colonies as described (Yang et al., 1993). For the other mutations, the RHAMM cDNA reading frame was amplified with Polymerase Chain Reaction (PCR, Sambrook et al., 1989). The complete open reading frame was amplified with two oligonucleotides as primers: one complementary to the translation initiation region (nucleotides 1–22) creating a BamHI site linked to nucleotide 1 (5'GT GGA TCC ATC CAG ATC CTG ACA GAG AGG C) (SEQ ID NO:51), the other to the region 280 bp after the translation stop codon (nucleotides 1685–1706) creating an EcoRI site linked to nucleotide 1706 (5'AAT GAA TTC CTT TGG TGA ACA GCA GT) (SEQ ID NO:52). The reaction was carried out at 94° C. (30 sec), 54° C. (30 sec) and 72° C. (90 sec) for 25 cycles. The PCR product (1.7 Kb) was treated with double Geneclean using a kit from BioRad and conducted according to the manufacturer's instruction.

In the restriction endonuclease digestion step, BamHI and EcoRI were used. The EcoRI-BamHI DNA fragment was ligated to an EcoRI and BamHI opened pGEX-2T (Eaton et al., 1986; Smith and Johnson, 1988, Pharmacia). The ligation mixture was transformed into *Escherichia coli* HB101 (Sambrook et al., 1989). DNA samples were prepared from 12 randomly picked clones and digested with BamHI and EcoRI. The clones containing the correct insert were issued for fusion protein preparation.

(b) Expression and Purification of RHAMM GST-Fusion Protein

A clone containing the correct insert in pGEX-2T was grown in 20 ml LB/amp medium at 37° C. overnight and then diluted to a density of 0.2 $O.D._{590}$. Isopropylthio-β-D-galactoside (IPTG) was added to the cultures, to a final concentration of 0.1 mM IPTG, and incubated for 2 h at 37° C. to induce the biosynthesis of fusion protein. Cells were harvested by centrifugation at 5,000 g for 5 min, then resuspended in 20 ml 50 mM Tris-Cl, pH 8.0, containing 2 M urea, 1% Triton X-100 and 1× protease inhibitors (Hardwick et al., 1992). Cells were disrupted by sonication. Bacterial debris was pelleted by centrifuging at 10,000 g for 20 min and the supernatants containing the extracted fusion protein were recovered for further protein purification.

Glutathione Sepharose 4B powder was brought to 10 ml suspension in $H_2O$, packed into a column and stabilized with 50 ml PBS containing 1% Triton X-100. Cell-free extract (20 ml) was applied to the column and the column was washed with 200 ml PBS containing 1 Triton X-100. RHAMM-GST fusion protein was eluted with 50 mM Tris-Cl, pH 8.0 containing 20 m/M glutathione as 5 fractions and then elecrophoresed on SDS-PAGE to evaluate the purity and concentration of the fractions.

(c) Preparation of Antibodies to RHAMM Fusion Protein

Antibody was prepared against RHAMM-GST fusion protein excised from SDS-PAGE gels in New Zealand white rabbits by intramuscular injection of 100 μg fusion protein together with RIBI adjuvant (Cedarlane). A second injection of 50 μg fusion protein with RIBI adjuvant was carried out 3 weeks later in each leg. Blood was withdrawn after two weeks and serum was tested in a ELISA method described by Douillard and Hoffman (1983) to ascertain antibody titres. The specificity of the antibody was determined by the ability of excess fusion protein (70 μg/ml) to compete for binding of antibody to purified RHAMM expression protein in a Western blot assay.

(d) Purity and HA Binding Ability of RHAMM-GST Fusion Protein

Figure 35B:
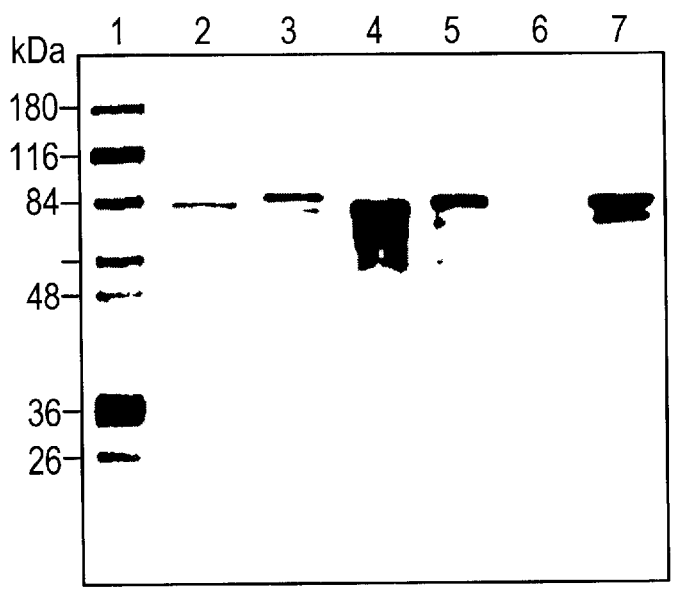

RHAMM-GST fusion protein was expressed and purified as described in (b) above and examined after electrophoresis on SDS-PAGE. Visualisation with Coomassie Blue showed a single band (FIG. 35B, lane 3). The protein showed binding to anti-RHAMM antibody (FIG. 35B, lane 5). In a transblot binding assay, the protein showed binding to biotinylated HA (FIG. 35B, lane 7).

(e) Effect of RHAMM-GST Fusion Protein on Cell Locomotion

RHAMM-GST fusion protein prepared and purified as described in (b) above was added at concentrations of 1 pg/ml, 1 ng/ml, 1 μg/ml and 1 mg/ml to 70% confluent C3 cultures and cell locomotion was monitored by image analysis for 2 h from protein addition as described in Example 5.

For each experiment, 30 cells were tracked every 10 min for a 1 hr period. Three trials of each group were observed for a total of 90 cells per group.

The results of the cell locomotion study are showed in FIG. 36A. Fusion protein at concentrations of 1 ng/ml and greater significantly inhibited cell locomotion.

Inhibition was concentration dependent. Addition of GST alone or GST-bovine serum albumin fusion protein had no effect on locomotion (data not shown).

(h) Partial Deletion of HA-Binding Domains in RHAMM

RHAMM cDNA was amplified in PCR using two oligonucleotides as primers: one complimentary to the translation initiation region (nucleotide 1–22 of RHAMM cDNA), the other complimentary to the nucleotide 1206–1230. The resulting PCR product encoded RHAMM cDNA in which the HA binding domain peptide$^{aa423\text{-}432}$ was completely deleted while the other HA binding domain peptide$^{aa401\text{-}411}$ was partially deleted. The two basic amino acids ($K^{405}$ and $K^{409}$) of domain I, shown in contribute to HA binding, were mutated to $E^{405}$ and $E^{409}$. The PCR product was doubly digested with BamHI and SacI. The plasmid containing RHAMM cDNA was also digested with BamHI and SacI. Plasmid-containing fragments (5.3 kb) were recovered by using a Prep-A-Gene Kit. The fragment was ligated to the BamHI-SacI fragment of the PCR product and transformed into E.coli HB101. DNA samples prepared from randomly picked clones were confirmed to contain correct inserts by restriction digestion with BamHI+SacI and by sequence analysis. Those clones containing a correct BamHI-SacI insert were used to make fusion proteins. Undeleted RHAMM fusion protein and HB101 lysate were used as controls. The results are shown in FIGS. 35A and B and 36B.

(g) Site Directed Mutagenesis of HA Binding Domains in the RHAMM cDNA

Mutation of specific basis amino acids shown to be critical for binding of RHAMM to HA (Yang et al., 1993) in domain I and II of RHAMM was accomplished in two steps. In the first step, site-directed mutations were confined to basic amino acids $K^{405}$ and $K^{409}$ which were altered to $E^{405}$ and $E^{409}$ as shown in FIG. 7A. This was carried out by making a primer (3'TAG CTT GTA CAA CAC CTT AAC TTC GAA AAT 5') (SEQ ID NO:53) contaning the above alteration. A mutated RHAMM cDNA was generated with PCR by using this primer and a primer complementary to the translation initiation region of the RHAMM cDNA.

Using the mutated RHAMM cDNA obtained in step I, we proceeded to modify the second HA binding domain to change $K^{430}$, $R^{431}$ and $K^{432}$ to $N^{430}$, $W^{431}$ and $E^{432}$, as shown in FIG. 37A. This was carried out by making a primer (3' CAA TTA ACC CTT GTT TTA CTC GAG TCT GAA 5') (SEQ ID NO:54) that contained the alteration of the 3 basic amino acids. A mutated RHAMM cDNA was generated by using this primer, a primer complementary to the translation initiation region and the mutated cDNA obtained as described in the above paragraph as a template. This mutated RHAMM cDNA was expressed as a mutated RHAMM fusion protein as above. The results are shown in FIG. 37B.

(h) Purity and HA Binding of HA-Binding Domain Deleted Mutated RHAMM(M-GST Fusion Protein The HA binding domains in the RHAMM fusion protein were altered as shown in FIG. 35A, in which the HA binding domain II (Yang et al., 1993, aa$^{423\text{-}432}$) of RHAMM cDNA was completely deleted and HA binding domain I(aa$^{401\text{-}411}$) was partially deleted. Two basic amino acids (aa$^{405}$ and aa$^{405}$) that were shown to be critical in HA (Yang et al., 1994) were then mutated to $E^{405}$ and $E^{409}$ to ablate binding of domain I.

The altered RHAMM cDNA was expressed and purified as described in (b) above and examined by SDS PAGE gel electrophoresis.

Visualization with Coomassie Blue showed a single band (FIG. 35B, lane 2).

The deleted/mutated fusion protein retained its antigenicity, as seen by binding to anti-RHAMM antibody (FIG. 35B, lane 4) but completely lost HA-binding ability, as seen by its failure to bind to biotinylated HA (FIG. 35B, lane 6).

(i) Effect of HA-binding Domain Deleted/mutated RHAMM-GST Fusion Protein on Cell Locomotion RHAMM-GST fusion protein, as described in (d) above, and deleted/mutated RHAMM-GST fusion protein, as described in (h) above were added at 5 ng/ml to subconfluent cultures of C3 cells and cell locomotion was monitored by image analysis for 2 h from protein addition as described in Example 5.

The results are shown in FIG. 25. The altered RHAMM-GST fusion protein had no significant effect on locomotion, while the unaltered fusion protein significantly reduced locomotion (40% at 1 ng/ml; $p<0.0001$).

To reduce possible conformational effects resulting from the above described deletion that might introduce artificial results, aa$^{405,409}$ in domain I and aa$^{430\text{-}432}$ were site mutated and the altered cDNA was expressed as a GST-fusion protein as described in (g) above. This altered protein also retained its antigenicity but failed to bind HA and had no significant effect on cell locomotion (FIG. 37C).

(j) Effect of Truncated RHAMM on Cell Locomotion

RHAMM-GST fusion protein was truncated to remove the carboxy terminus containing both HA binding domains (aa$^{435}$ to aa$^{570}$ of RHAMM II) as described in Yang et al., 1993.

The truncated protein shows inhibition of cell locomotion ($p<0.005$), although less than that of the intact fusion protein ($p<0.001$). Results are shown in FIG. 38.

Example 7

RHAMM and Human Breast Cancer (a) Methods (a) Cell Lines

Human breast cancer cell lines, MDA-MB-231, MCF-7, MDA-MB-468, ZR-75-1, T-47-D and Hs-578-T used in this study were purchased from American Type Culture Collection (Rockville, Md.) and were routinely maintained on the surface of plastic tissue culture plates (Corning Glassware, Corning, N.Y.) in growth media—Dulbecco's Modified Eagle's Medium (DMEM, Gibco BRL, Burlington, Ontario) supplemented with 10% (v/v) fetal calf serum (FCS, Hyclone laboratories, Inc., Logan, Utah) and 20 mM HEPES (Sigma Chemical Co., St. Louis, Mo.), PH 7.2. Cells were incubated at 37° C. in a 95% air, 5% $CO_2$ atmosphere in a humidity controlled incubator and subcultured with 0.25% trypsin (Gibco BRL)/2 mM EDTA (Sigma) in PBS (38 mM NACL, 8.1 mM $Na_2HPO_4$, 2.7 mM $KCl_2$ and 1.1 mM $KH_2PO_4$, PH 7.4).

(ii) Human Tissues

Paraffin-embedded section of human breast tissue including normal tissue (from reduction mammoplasties), benign and malignant tumours were obtained from Dr. R. Stern, University of California at San Francisco.

(iii) Antibodies and Peptides

Both polyclonal antibodies used in this study, R3 and anti-fusion protein antibody, were raised in rabbits to a specific peptide (aa$^{269\text{-}288}$) encoded in the murine RHAMM cDNA (Hardwick, 1992) and to glutathione transferase (GST)-RHAMM fusion protein (Yang et al., 1993), respectively. The specificity of both antibodies has been confirmed. Normal rabbit IgG was used as control. A synthetic designated peptide I, mimicking the hyaluronan binding Domain I (aa$^{401-411}$)—YKQKIKHVVKLK—and a scrambled peptide I, consisting of the same amino acids arranged in a random manner—YLKQKKVKKHIV—were used in locomotion assays.

(iv) Timelapse Cinemicrography and Cell Locomotion

Cells were cultured as described above. For cell locomotion studies, aliquots of $10^5$ cells were added to a 25 cm$^2$ tissue culture flask (Corning). After 24 hours of growth, cells were washed with calcium and magnesium free Hank's balanced salt solution (HBSS) (Gibco BRL), the defined serum-free media (DM), DMEM supplied with 4.0 µg/ml transferrin (Human, Gibco BRL), 0.5 U/ml Lente insulin (beef and pork, Connaught Novo Ltd., Willowdale, Ontario) and 20 mM Hepes, PH 7.2, was added to the flasks. Twelve hours later, cell locomotion was recorded by using a computerized timelapse image analysis system (Image-1, Universal Image Corporation, Westchester, Pa.) which quantitates nuclear displacement Antibody—R3 (5 µg/ml), peptide I (2 µg/ml), control rabbit IgG (5 µg/ml) or scrambled peptide I (2 µg/ml) were added to media 20 min before the beginning of filming. Images were taken with a Zeiss inverted microscope (model IM35, Zeiss) using a 10× objective every 30 min for 3 hours. A minimum of 30 cells were tracked in each above experimental condition; experiments done in triplicate.

(v) Western Immunoblot Analysis

The cells were grown in growth media and changed to defined media for 24 hours before harvest. After washing with ice cold PBS, the cells were lysed with ice cold modified RIPA lysis buffer (25 mM Tris HCl, PH 7.2, 0.1% SDS. 1% triton-X, 100 1% sodium deoxycholate, 0.15 M NaCl, 1 mM EDTA) containing the proteinase inhibitors leupeptin (1 µg/ml), phenylmethyl sulfonyfluoride (PMSF, 2 mM), pepstatin A (1¾ g/ml), aprotinin (0.2 TIU/ml) and 3,4-dichloroisocoumarin (200 µM) (all chemicals from Sigma). Lysates were scraped into microcentrifuge tubes, and then centrifuged at 13,000 rpm for 20 min at 4° C. (Heraeus Biofuge 13, Baxter Diagnostics Corporation, Mississauga, Ontario) after waiting for 20 min on ice. Protein concentrations of the supernatants were determined using the DC protein assay (Bio-Rad Laboratories, Richmond, Calif.). Five µg of total protein from each cell lysate in an equal volume of SDS reducing sample buffer was loaded and separated by electrophoresis on a 10% SDS-PAGE gel together with prestained molecular weight standards (Sigma) (Laemmli, 1970). Separated proteins were transferred onto nitrocellulose membranes (Bio-rad) in a buffer containing 25 mM Tris-HCl, 192 mM glycine, 20% methanol, pH 8.3, using electrophoretic transfer cells (Bio-Rad) at 100 V for 1 hour at 4° C. Additional protein binding sites on the membranes were blocked with 5% defatted milk in TBST (10 mM Tris base, 150 mM NaCl, pH 7.4, with 0.1% Tween 20, Sigma). The membranes were incubated with the primary antibody (R3, 1:100, 1 µg/ml in defatted milk TBST) overnight at 4° C. on a gyratory shaker. After washing 3 times with TBST, the membranes were incubated with horseradish peroxidase-conjugated goat anti-rabbit IgG (1:5000 dilution in 1% defatted milk in TBST) for 1 hour at room temperature and washed with TBST, then TBS. Blotting was visualized by chemiluminescence (ECL) Western blotting detection system (Amersham International Plc., Amersham UK) according to the manufacturer's instructions. The quantitation of optical densities of the resultant bands was performed on the Bio-Rad Model 620 Video Densitometer and analysized using the 1-D Analyst II software. The specificity of the antibody was confirmed by probing the blots with both rabbit IgG and R3 pre-incubated with RHAMM fusion protein.

(vii) Flow Cytometry (FACS)

Cells grown on 100 mm culture plates were cultured in defined media for 24 hours before harvesting with 2 mM EDTA in HBSS and washed once with HBSS containing 10% FBS and 0.02% sodium azide (FACS buffer). The viability of cells was between 85% and 95% as determined by Trypan blue exclusion. An aliquot of $2 \times 10^6$ cells was incubated with primary antibody R3 (1:50, 20 µg/ml) in a total volume of 200 µl of FACS buffer for 30 min on ice and washed once in cold FACS buffer. Then FITC-conjugated goat anti-rabbit IgG antibody (1:300 dilution, Sigma) was added and incubated for 30 min in the dark on ice. The cells were washed again, fixed in 400 µl of freshly prepared 1% paraformaldehyde in PBS and examined with a Coulter Electronics EPICS flow cytometer (Model 753, Epics, Inc. New York) (500 mW, 488 nM). Forward and 90° light scatter measurements were used to establish gates for intact, viable cells. Fluorescence was detected at 525 nM. Signal parameter, 255 channel, log integral green florescent histogram were obtained, based on $5 \times 10^3$ gated events. Rabbit IgG was used as a negative control for each cell line.

(vii) Collagen Gel Invasion and Antibody Blockade Assay

Vitrogen 100 (Celtrix Laboratories, Palo Alto, Calif.) from bovine dermal collagen, containing predominately type I collagen, was used. Neutralized isotonic vitrogen collagen solutions were prepared and added to a 24-well plate (Falcon, Becton Dickinson Labware, Lincoln Park, N.J.). Aliquots of $10^4$ cells were added per well in a volume of 1 ml growth media on the surface of the polymerized collagen. For antibody blockade, antibodies R3 (from 5–20 µg/ml) or anti-fusion protein antibody (from 5–20 µg/ml) were added to the media at the beginning and after 24 hours incubation. Collagen invasion was quantitated after 48 h by counting the number and the depth from the surface of each cell in several fields that were randomly selected using an inverted phase-contrast microscope (Schor, 1980). The percent invasion relates the number of the cells that are located at 25 or more micrometers below the surface, to the total number of cells in 5 fields.

(ix) Determination of HA Production

When cultured cells reached 80% confluence, the media was aspirated, cells were washed with HBSS and the defined serum-free media was added to plates. The cells were then maintained for 48 hours. The media were collected and cell number was determined. The HA concentration in the media was measured in duplicate using a commercially available HA test kit from Kabi Pharmacia Diagnostics AB (Uppsala, Sweden) by radioimmunoassay) and normalized for cell number (µg/L/$10^6$ cells).

(x) RNA Extraction and Northern Blot Analysis

Total cellular RNA was isolated by lysis of the cells in guanidinium thiocyanate, followed by centrifugation over a cesium chloride gradient (Chirgwin et al., 1979). Purity and quantity of the RNA was assessed by determining optical density at 260 and 280 nm using LKB spectrophotometer (LKB Biochrom, UltraSpec) and running a denaturing 2.2 M formaldehyde/1.3% agarose gel. One hundred µg of total RNA was electrophoresed through formaldehyde/agarose gels and transferred to Hybond™-N hybridization transfer membrane (Amersham) by capillary action. After fixation by UV crosslink using Stratalinker™ UV Crosslinker (Stratagene, La Jolla, Calif.) according to the manufacturer's instruction, the membrane was prehybridized in a buffer containing 50% formamide. 6×SSPE=0.18 M Na Cl, 10 mM Na$_2$PO$_2$,PH 7.7, 1 mM Na$_2$EDTA), 5×Denhardt's solution [1×Denhardt's=0.02% (W/V) each of Ficoll (Type 400, Pharmacia), PVP-40 (polyllidone) and BSA], 0.1% SDS, 10% (W/V) Dextran sulfate, and 100 μg/ml denatured salmon sperm DNA for a minimum of 5 hour at 42° C. Then the membrane was hybridized with the same buffer plus $2\times10^6$ cps of $^{32}$P-labelled 528 bp RT-PCR products of human breast cancer cell line total RNA (see below), which has 84% homology to murine RHAMM cDNA (Hardwick, 1992), overnight at 42° C. After hybridization, the membranes were washed twice in 2×SSC (1×SSC=0.15 M NaCl, 15 mM Sodium citrate), 0.1% SDS for 30 min at room temperature, and twice in 0.4×SSC, 0.1% SSC for 10 min at 65° C. to remove non-specifically bound probe and exposured to Kodak X-OMAT™ AR film at −80° C. with two intensifying screens. The size of transcripts identified by hybridization was calculated using an external RNA ladder (0.24–9.5 Kb, Gibco BRL). The probes were then stripped by incubating the blots for 2 hours in 5 mM tris-HCl, pH 8.0, 2mM $Na_2EDTA$, 0.1×Denhardt's solution, and 0.05% Na pyrophosphate at 65° C. and reprobed with 28s ribosomal RNA as control for equal loading.

(xi) RT-PCR Analysis

Total cellular RNA was isolated from cultured cell lines as described above. For cDNA synthesis, 1 μg of total RNA, oligo (dT) primer, MMLV reverse transcriptase and the first strand cDNA synthesis kit (Clontech, Clontech lab, Inc., CA) were used under conditions recommended by the manufacturer in a 20 μl reaction volume. After dilution to 100 μl, 2 μl was used for PCR amplification. PCR reaction was conducted following the protocol of Clontech Amplimer Kits in Rt-PCR. PCR reactions were carried out at 94° C. (45"), 56° C. (45") and 72° C. (2') for 30 cycles. The primers used for RHAMM were 5' primer AAATAGAAGATCT-TAAACTGG (SEQ ID NO:50) and 3' primer TTTGAGT-TGGCTATTTTCATC; (SEQ ID NO:55) a 528 bp fragment resulted. RT-PCR products were analyzed by agarose gel electrophoresis, and also sequenced; sequence analysis and comparisons were conducted using the BLAST algorith (Altschul et al., 1990). Quantitative analysis of the relative amounts of RHAMM transcripts expressed was determined by comparing the expression of the RHAMM gene with that of human β-actin gene, the primer for which were 5' primer, ATCTGGCACCACACCTTCTACAATGAGCTGCG (SEQ ID NO:56) and 3' primer, CGTCTACACCTAGTCGT-TCGTCCTCATACTGC (SEQ ID NO:57). This resulted in a 838 bp fragment (Clontech).

(xii) Immunocytochemistry

The Avidin-biotin-peroxidase complex method was used as described for the staining of CD44 (Wang et al., 1992). Briefly the slides were incubated with 1.5% goat serum in 0.01 M Tris-buffered saline (TBS) for 1 hour to block non-specific binding. The primary antibody, anti-RHAMM peptide $aa^{268-288}$, (R3) diluted with 1.5% goat serum/TBS (1:500), was incubated on slides overnight at 4° C. Endogenous peroxide activity was blocked by incubating the slides with 0.6% $H_2O_2$ in methanol (Mallinckrodt) for 30 minutes at room temperature. The slides were then incubated with biotinylated goat anti-rabbit IgG (Vectastain ABC peroxidase kit, Vector Labs, Burlingame, Calif. 1:200 in 0.01 M TBS) for 1 h at room temperature, followed by an avidin-biotin-peroxidase complex (Vectastain, Vector labs, 1:200 in 0.1 M TBS). Between each step, the slides were washed three times with 0.01 M TBS. The peroxidase activity was developed by incubation in 0.05% DAB (3,3'-diaminobenzidine, Sigma) and 0.1% $H_2O_2$ in 0.05M TBS. Some slides were counter-stained with 0.25% methyl green. Some slides were not counter-stained and were used for image analysis (below). Both non-immune sera and antibody preabsorbed with RHAMM fusion (recombinant) protein were used as negative control.

(xiii) Computer-Assisted Image Analysis

A microscope coupled to a Cohu high-resolution black-and-white camera was connected to a Packard Bell 386 computer via a PC Visionplus board. The intensity of RHAMM peroxidase staining was measured using the Densitometry/Fluorometry module (IM4100) of the Image-Measure software package (Phoenix Biotechnology, Seattle, Wash.). Quantitation of peroxidase staining was done by using standard densitometric techniques (Brown 1990) on non-counterstained sections by the repeated placement of a 100-pixel window over section areas selected by random cursor movement in a 200× magnified image. 200 non-overlapping area measurements were taken for each section.

(xiv) Statistical Analysis

Student's t-test was used for the effect of RHAMM antibodies and peptides on cell locomotion and for collagen gel invasion data, and one way analysis of difference was used for computer-assisted image analysis of RHAMM staining in human breast tissue slides.

(b) Cell Lines in Their Morphology

All cell lines employed exhibited an epithelial-like morphology and were cohesive (FIG. 39). However, the precise morphology of the epithelial cell lines varied. MDA-MB-231 are spindle-shape cells. MCF-7 cells exhibit a polygonal shape while MDA-MB-468 cells are small and round. ZR-75-1 cells are pleomorphic epitheloid cells, the colonies of which are usually densely packed with polygonal or cuboidal cells that formed in what appeared to be multi-layered colonies or single cells. T-47-D cells formed predominantly polygonal cell colonies with a typical epitheloid appearance. Hs-578-T cells are most spread (FIG. 39).

(c) RHAMM Expression in Cell Lines

Figure 40B:
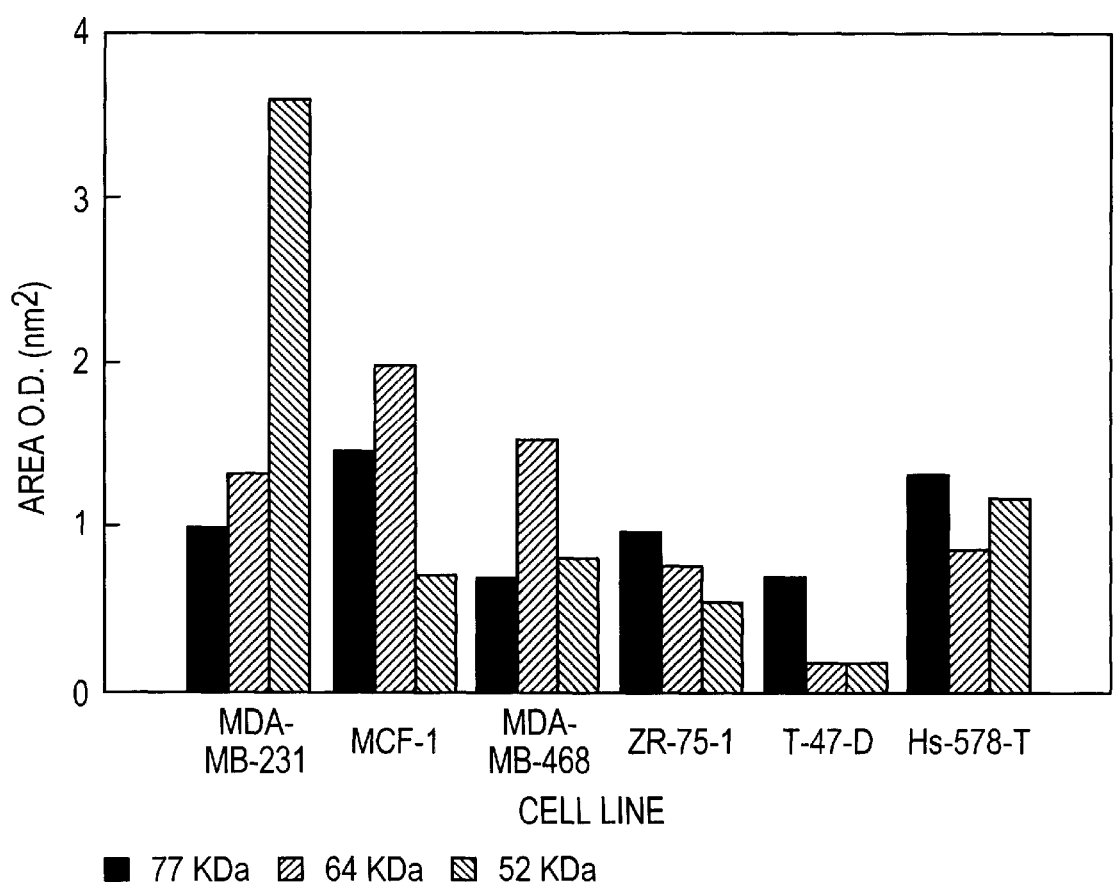
Figure 40C:
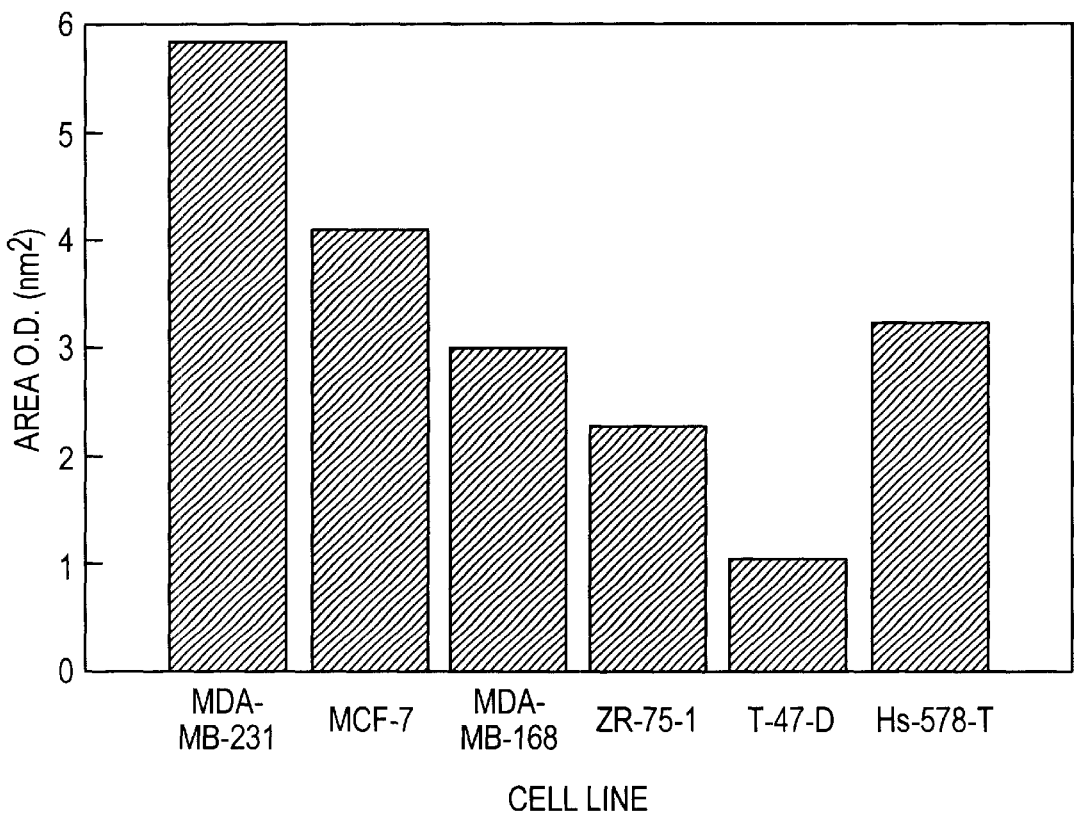

The expression of RHAMM in the human breast cancer cell lines of (a) (i) above was investigated by a number of methods. First, lysates of each of the six cells lines were subjected to SDS-PAGE, transblotted onto nitrocellulose membrane and incubated with anti-RHAMM peptide antibody (R3). The antibody detected 3 major bands—77 Kd, 64Kd and 52Kd (FIG. 40A), all of which were specifically blocked by competition with RHAMM fusion protein. Total RHAMM expression measured by densitometry was MDA-MB-231>MCF-7>Hs-578-T>MDA-MB-468>ZR-75-1>T-47-D (FIG. 40C). Densitometric analysis of western blots indicated that 77 and 64 Kd protein band expression was elevated in the MCF-7 cell lines, while the 52 Kd protein band was expressed in a 3 fold greater amount in MDA-MB-231 cell line than in the other cell lines (FIG. 40B). In order to assess whether RHAMM was localized at the cell surface in the breast carcinoma cell lines, flow cytometry analysis (FACS) was performed. Cell surface expression of RHAMM occurred in all cell lines, but the greatest intensity of staining was found in the MDA-MB-231 and MCF-7 cell lines (FIG. 41). This elevation correlated well with the total increase in RHAMM detected by densitometry of Western blot, but clearly different forms were elevated in the two maximally motile cell lines.

(d) RHAMM mRNA Expression is Elevated in Metastatic Cells

Figure 42B:
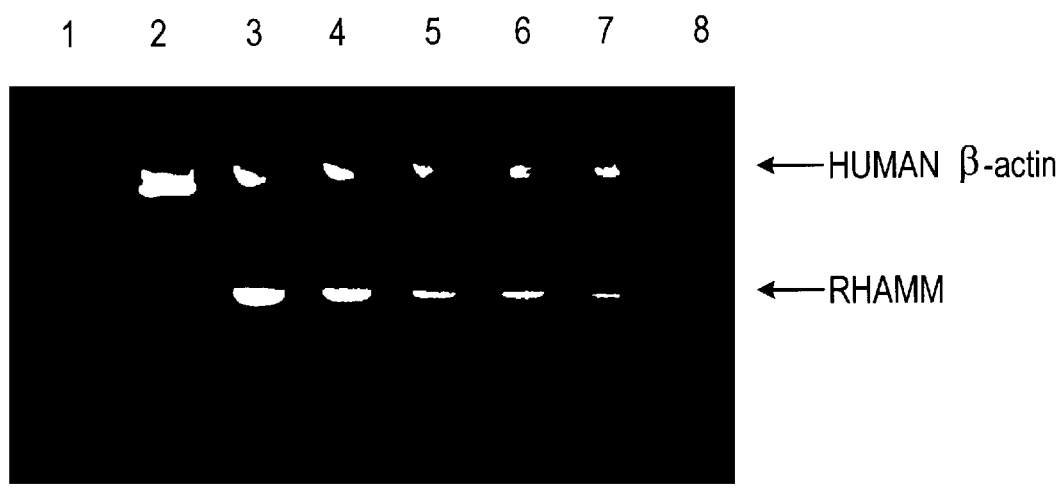

Northern blot analysis of total RNA extracted from cultured cells revealed a 3.1 Kb transcript (MDA-MB-231 shown, FIG. 42A) that occurred in all cell lines. Since the levels of mRNA in most of the cell lines was near background, to assess any difference, "quantitative" RT-PCR analysis was used. Results confirmed that RHAMM mRNA was highest in MDA-MB-231 cell line, followed by MCF-7, followed by ZR-75-1 and MDA-MB-468 (approximately equivalent), followed by T-47-D (FIG. 42B).

RT-PCR product sequence analysis on MDA-MB-231 confirmed that it was 78% identical to mouse RHAMM at protein level (FIG. 42C).

(e) RHAMM is Critical to Locomotion of All Cell Lines in vitro

Random cell locomotion was measured by using a computerized timelapse image analysis system. MDA-MB-231 locomotion, at 23.3 μm/h and MCF-7, at 14.4 μm/h were significantly more rapid (P<0.001) than all other cell lines tested (FIG. 43). The rate of random cell locomotion correlated well with the level of RHAMM expression.

In order to establish the RHAMM was indeed involved in the mechanism of locomotion in these cell lines, the ability of anti-RHAMM peptide antibody (R3) and of a peptide mimicking the HA binding domain I of RHAMM (Yang, 1993) to block locomotion was assessed (FIG. 43). In the presence of either anti-RHAMM antibody R3 or peptide, the locomotion of all cells was reduced significantly (P<0.001).

(f) RHAMM is Required for Invasion into Collagen Gels in vitro

Figure 44A:
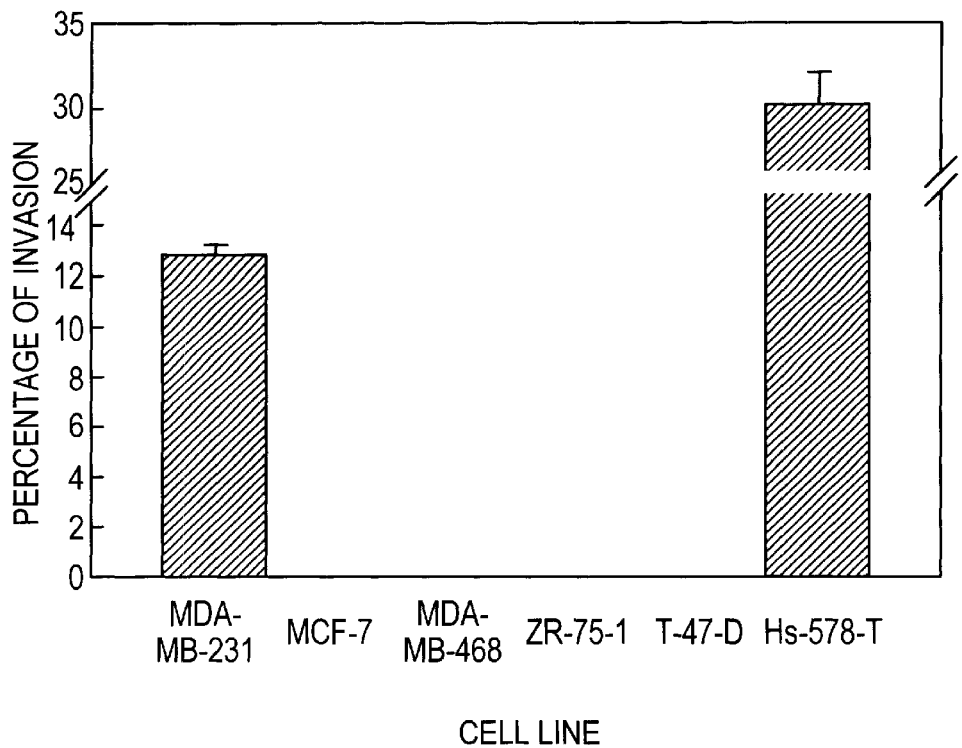
Figure 44B:
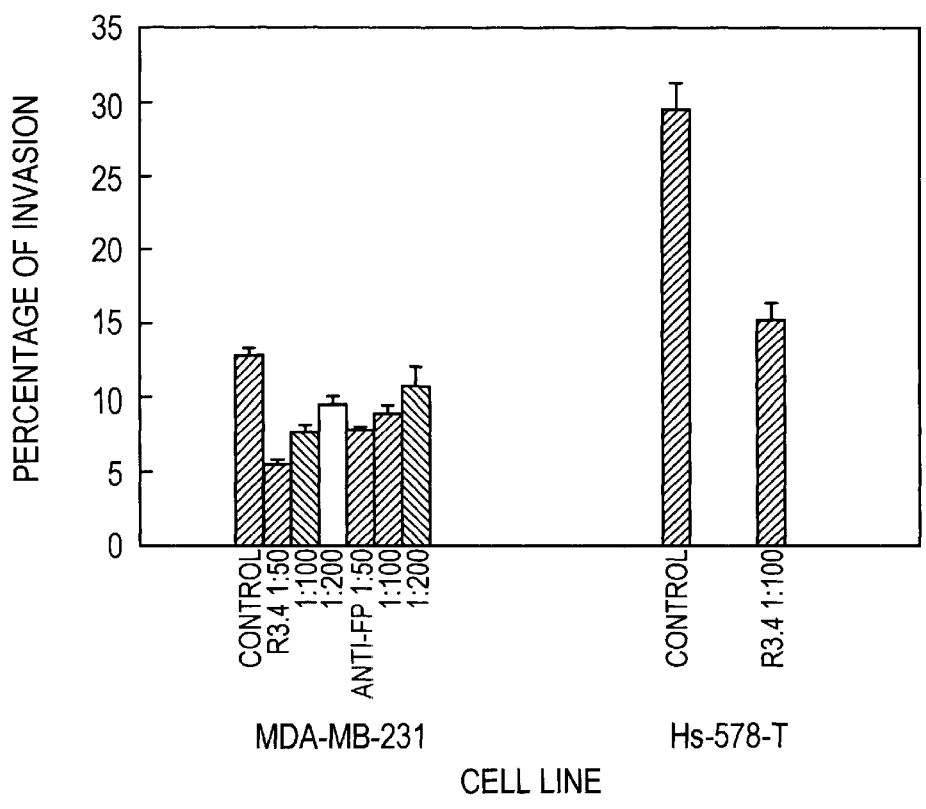

The invasive behaviour of the human breast cancer cell lines into collagen gels was investigated. Only MDA-MB-231 and HS-578-T cells significantly invaded gels (25 to 100 μm) 48 h after plating the cells onto the gel surface (FIG. 44A). In order to evaluate the role of RHAMM in MDA-MB-231 invasion, anti-RHAMM peptide antibody (R3) and anti-RHAMM fusion protein antibody were added to the media. Invasiveness of these cells was significantly inhibited by anti-RHAMM antibodies (P<0.001) (FIG. 44B).

(g) HA Production Correlates with Invasive Potential

HA production by human beast cancer cell lines was determined by measuring HA concentrations released into defined serum-free media ($\mu$g/L/$10^6$ cells). MDA-MB-231 and HS-578-T cells produced 7.5–18 times and 47.5–114 times more HA respectively than the other cell lines (FIG. 45). Since only the MDA-MB-231 and Hs-578-T cells were invasive, HA production correlated well with invasive potential.

Figure 46A:
Figure 46B:
Figure 46C:
Figure 46D:

(h) RHAMM Expression is Associated with Tumorigenesis and Progression of Human Breast Cancer in Vivo Low levels of RHAMM were expressed in normal mammary ducts and glands (FIG. 46A). Staining intensity was increased significantly in benign tumours (FIG. 46B) but was far more intense in malignant breast tissue (FIG. 46C). In particular, metastatic breast tumour in lymph nodes expressed higher levels of RHAMM than the primary tumour tissue (FIG. 47). Analysis of densitometric quantification of staining demonstrated differences in RHAMM staining among normal, benign and malignant breast tissues, and between primary and metastasis tumour tissues were statistically significant (P<0.01).

Example 8

Screening of Breast Cancer Biopsies

In a blinded study, 400 slides from human breast cancer biopsies were stained for RHAMM as described in Example 7. Biopsy samples were from many patients and, in some cases, there were multiple biopsies from individual patients at different stages of their disease.

Densitometry was performed on the slides as described in Example 7, and the level of RHAMM elevation (level of staining) was ranked on a scale of 0 to 5 above background, background staining being that of reduction mammoplasty samples.

After the level of RHAMM was ranked, the blinding code was broken and the level of RHAMM was compared with the history and prognosis of the patients.

As seen in FIG. 48, there was a very significant difference in patient survival between patients with a maximum RHAMM level in the range of 0–1 and those with a maximum in the range of 3.5–4. Analysis of the level of RHAMM expression in breast tumours provides a new and valuable indicator of the likely outcome in human breast cancer patients.

Example 9

RHAMM and Muscle Cell Migration

Animals

Male Sprague-Dawley rats (Charles River) weighing 325–350 g and aged 15 weeks were used throughout these experiments.

Balloon Catheter Injury

Animals were anesthetized with 80 mg/kg of ketamine (Aveco) and 6 mg/kg xylazine (Haver) intramuscularly. The left carotid artery was exposed and a 2F Fogarty balloon catheter (Baxter, model 12-060-2f) was introduced into the lumen. With the balloon inflated, the catheter was passed through the common carotid three times to remove the endothelium. The injured common carotid artery was harvested at various times after de-endothelialization. Sham operated animals had their left carotid artery exposed without passage of the catheter and the right artery was harvested for study.

Cells and Cell Lines

Smooth muscle cells were isolated from bovine aorta as described previously from rat aorta (Majack et al., 1984) and were maintained in Dulbecco's Modified Eagles medium (DME) supplemented with 10% fetal calf serum (FCS) and 20 mM HEPES buffer, pH 7.2 at 37° C. and 5% $CO_2$ in air. All experiments were performed using defined medium [DME with 20 mM HEPES buffer, pH 7.2, 0.5 U/ml insulin (beef and pork zinc suspension, Novo Laboratories Ltd., Willowdale, Ontario) and 4 μg/ml transferrin (Sigma Chemical Co., St. Louis, Mo.)], and the culture medium was replaced 24 hours before filming. Wounding injury to confluent monolayers consisted of removal of half the monolayer using a cell lifter followed by the addition of fresh defined medium in the presence of either RHAMM peptide aa401-411 or the scrambled peptide of the same domain as described above.

The macrophage cell lines S1 and WEHI-3 (Branch et al., 1989) were used to analyze the effect of antibodies and synthetic peptide on macrophage chemotaxis to endotoxin-activated mouse serum (AS). These cells lines were also maintained in DME with 10% FCS and 20 mM Hepes buffer, pH 7.2 at 37° C. and 5% $CO_2$ in air.

Human neutrophils were obtained from peripheral blood samples of normal volunteers and mixed in ACD solution (0.085 M trisodium citrate, 0.065 M citric acid, 2% dextrose) to prevent clotting. Five percent dextran was added and the separated plasma and white blood cells were removed. The cells were washed twice in PBS, pH 7.2 and a Ficoll gradient was used to separate the lymphocytes. The isolated neutrophils were then washed and resuspended in PBS. Red cells were lysed by brief exposure to hypotonic PBS.

Anti-RHAMM antiserum and RHAMM HA-binding Peptide

A polyclonal antiserum (anti-peptide $aa^{268-299}$ antiserum) was raised in rabbits to sequence $aa^{268-288}$ encoded in the RHAMM cDNA. This antiserum has been shown to block both HA-stimulated random locomotion and migration of smooth muscle cells following wounding and to partially block HA-binding to RHAMM.

The HA-binding region of RHAMM consists of two 10 amino acid domains located close to the carboxy terminus of the protein (Yang, 1993). A peptide mimicking Domain 1

(amino acids 401–411)—YKQKIKHVVKLK—and a scrambled peptide consisting of the same amino acids arranged in a random manner—YLKQKKVKKHIV—were synthesized. Both peptides were used at a final concentration of 2 µg/ml in locomotion assays.

Immunocytochemistry

Arteries harvested for immunocytochemistry were fixed in 10% phosphate buffered formalin, embedded in paraffin and processed to obtain 5 µm sections. Non-specific sites in the section were blocked with 1.5% goat serum in 0.01 M Tris buffered saline (TBS) for 1 hour. The sections were incubated overnight either with anti-peptide aa268-288 antiserum (1:100 dilution) dissolved in 0.01M TBS with 1.5% goat serum to detect RHAMM, or with the biotinylated HA-binding region of aggrecan (1:300 dilution) isolated from bovine nasal cartilage (Ripellino et al., 1985) to detect HA. The sections stained for RHAMM were incubated with biotinylated goat anti-rabbit IgG (Vectastain ABC peroxidase kit, Vector Laboratories, Burlingame, Calif., 5 µl/ml of 0.01M TBS). The activity of endogenous peroxidases was quenched with 0.6% hydrogen peroxide in methanol (Mallinckrodt) for half an hour at room temperature (RT). All sections were then incubated with an avidin-biotin-peroxidase complex (Vectastain, Vector Labs) for 1 hour at RT. Staining was obtained using diaminobenzadine (DAB, Sigma, 10 mg/ml in 0.05M TBS) and the reaction was stopped with distilled water. The colour of the reaction product was enhanced with 0.5% copper sulfate in 0.9% NaCl for 10 minutes. Sections were counterstained using 0.25% methyl green for 15 minutes. After clearing in n-butanol and xylene, the sections were mounted in Permount® (Fisher Scientific). The specificity of staining for RHAMM was confirmed by the greatly reduced staining observed following the use of serum from which RHAMM antibodies had been removed by affinity chromatography. Specificity of staining for HA was confirmed both by incubation of the probe with excess HA prior to staining, and by pretreatment of the sections with Streptomyces hyaluronidase to degrade HA prior to staining. Normal rabbit IgG (5 µg/ml, Sigma) was also used as a negative control.

Immunoblots

Carotid arteries were snap frozen in liquid nitrogen and maintained at −80° C. until further analysis. The tissue was homogenized in lysis buffer [25 mM Tris HCl, 0.1% sodium dodecyl sulfate, 1% triton X-100, 1% sodium deoxycholate, 0.15 M NaCl, 1 mM EDTA, and the protease inhibitors leupeptin (1 µg/ml), phenylmethyl sulfonylfluoride (2 mM), pepstatin A (1 µg/ml), aprotinin (0.2 TIU/ml) and 3,4-dichloroisocoumarin (200 µM)]. Protein concentration was determined by the DC protein assay method (BioRad, Richmond, Calif.) using an equal sample of the lysis buffer for background determination. Five µg of protein from each sample was separated on 10% SDS-PAGE, transblotted onto nitrocellulose membranes. Additional protein binding sites were blocked with 5% defatted milk in TTBS (0.01 M Tris base, 150 mM NaCl, pH 7.4, with 0.05% Tween 20, Sigma Chemical Co., St. Louis, Mo.). Blots were incubated with the primary antibody (anti-peptide aa$^{268-288}$ antiserum, 1:250 dilution in 1% defatted milk in TTBS) overnight at 4° C. The primary antibody was detected using goat anti-rabbit IgG antibody conjugated to horse radish peroxidase (Sigma Chemical Co., St. Louis, Mo.; 0.2 µg/ml in 1% defatted milk in TTBS) incubated for one hour at room temperature and was visualized with chemiluminescence (ECL, Amersham) as per manufacturer's instructions.

Timelapse Cinemicrography

Injured cell monolayers were monitored for motility using an IM 35 Zeiss inverted microscope to which a video camera (Hamamatsu CCD, Inc., Japan) was attached. The cells were maintained at 37° C. using a heated platform (TRZ 3700, Zeiss, Germany). Cell locomotion was followed by using image analysis (Image 1, Universal Imaging Corp., Westchester, Pa. This program allows quantification of nuclear displacement from a sequence of digitalized images. The motility of thirty cells in each experiment was followed for a period of 24 hours with mean velocities calculated every hour.

Chemotaxis Assay

Chemotaxis was stimulated using either bacterial endotoxin-activated mouse serum (AS), prepared according to Stevenson et al. (1981) for macrophages and macrophage cell lines, or 100 ng/ml interleukin-8 (IL-8) for neutrophils. Heat-inactivated serum (56° C. for 20 mintes) or medium served as negative controls respectively. The chemotactic assay used was a colorometric assay described in Shi et al., (1993). Briefly, a 96-well chemotaxis chamber with a lower recess large enough to hold a microtiter plate (Neuro Probe, stock#MBA96) and a 5 µm framed filter (Neuro Probe, stock#PFD5/A) were used. The microtiter plate was filled with chemoattractants and controls and placed in the recess of the chemotaxis chamber. The framed filter was then placed on the top of the filled microtiter plate. The chamber was then closed and 200 µl of a cell suspension ($2.5 \times 10^5$ cells/ml) in DME was then added to the wells of the upper plate. The chamber was incubated at 37° C. for 4 to 6 hours in 5% $CO_2$ in air. After incubation, the medium in the wells of the upper plate was replaced with 200 µl of PBS containing 20 µM EDTA and incubated at 4° C. for 30 minutes. Cells remaining on the top of the polycarbonate membrane were removed with cotton Q-tips. The cells which had migrated into or through the filter were collected by centrifugation with a 50 ml tube adaptor at 500 g for 10 minutes and transferred into a 96-well plate. The number of displaced cells was quantified by the addition of 3-(4.5-dimethylthiazol-2-yl)-2,5-diphenol tetrazolium bromide (MTT) to a final concentration of 250 µg/ml that was incubated at 37° C. for 4 hours. The dark purple crystals produced by the reduction of MTT were dissolved by mixing with 100 µl of acid-isopropanol (2 mM HCl). The plate was analysed within 2 hours on a microtiter plate ELISA reader with a filter of 540 nm. The degree of MTT reduction corresponds to relative cell number[20].

RHAMM and HA Expression Increase Following Balloon Catheter Injury of the Carotid Artery The endothelial and smooth muscle cells of carotid arteries obtained from uninjured rats were weakly positive for RHAMM (FIG. 49A, arrow points to internal elastic lamina). Two hours after injury, neutrophils and macrophages adhered to the denuded area and strongly expressed RHAMM (FIG. 49B, arrow points to internal elastic lamina). By six hours after injury, a small proportion of smooth muscle cells showed increased expression of RHAMM (FIG. 49C, arrow points to internal elastic lamina), and by 48 hours, smooth muscle cells adjacent to the internal elastic lamina stained strongly for RHAMM (FIG. 49D, arrow points to internal elastic lamina). By 7 days, and up to 14 days after injury, there was an increase in the size of the neointimal layer. Cells in this layer continued to express high levels of RHAMM (FIGS. 49E & F). Sections incubated with preimmune IgG or anti-RHAMM antisera that had been passed through a RHAMM-GST fusion protein column to remove anti-RHAMM antibodies showed no staining (data not shown). Sham operated controls showed no changes in the staining for RHAMM or HA and did not develop a neointimal layer (data not shown).

The expression of RHAMM was further investigated using western blot analysis of arteries from injured and sham operated animals using anti-peptide aa$^{268-288}$ antiserum. Constitutive expression of two major isoforms of RHAMM of 84 and 65 kDA was observed in uninjured arteries (FIG. 50). These isoforms were also expressed in injured arteries, although a slight decrease in the 84 kDA protein was seen at 48 hours and a slight increase in the 65 kDA protein was noted at 12 hours (FIG. 50). Interestingly, an additional isoform of 58 kDa was expressed between 12 and 36 hours, while a 70 kDa form appeared between 36 and 72 hours after injury (FIG. 50), coinciding temporally with the intense staining for RHAMM and HA observed in injured arteries (FIG. 49).

Figure 51A:
Figure 51B:
Figure 51C:
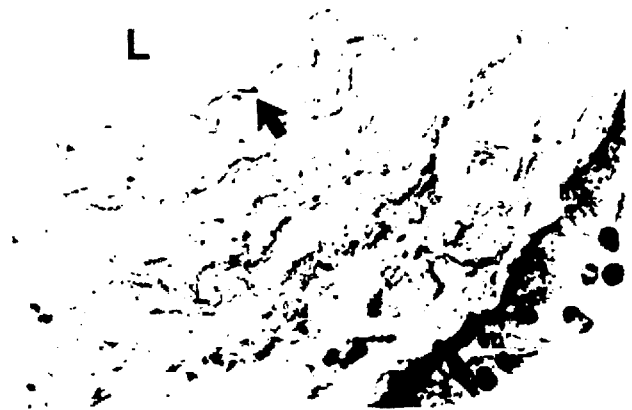
Figure 51D:
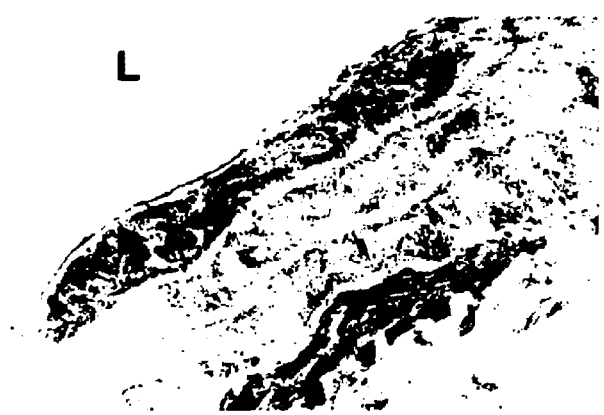
Figure 51E:
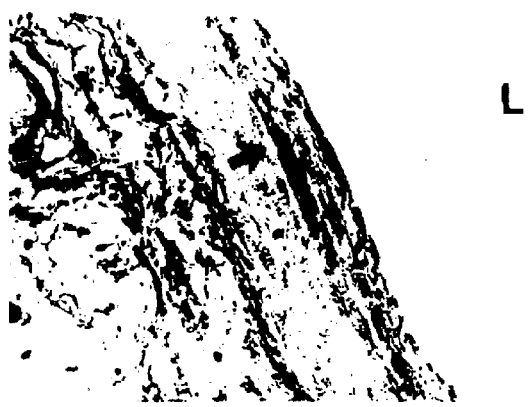
Figure 51F:
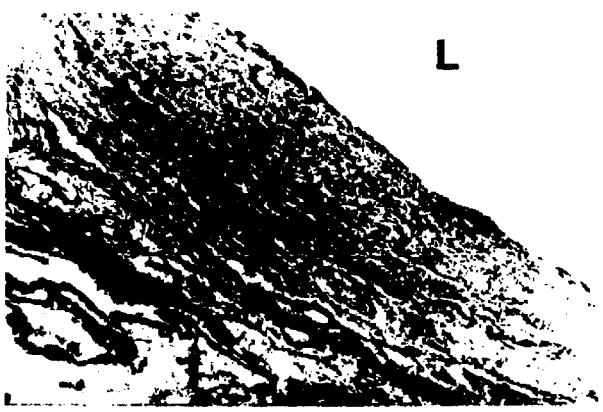

Distribution of HA in the uninjured carotid was restricted to the endothelium and the adventitia (FIG. 51A). Two hours after injury, the neutrophils and macrophages adherent to the denuded area showed a slight degree of HA-staining (FIG. 51B). By 48 hours, the smooth muscle cells adjacent to the internal elastic lamina were strongly positive for HA (FIG. 51D), coincident with their expression of high levels of RHAMM (FIG. 51D) and subsequent migration to form the neointima. By 14 days, the staining for HA decreased and became restricted to cells at the junction of the media and the neointima (FIGS. 51E & F). Sections pretreated with hyaluronidase or preincubation of the biotinylated HA-binding probe with HA prevented staining (data not shown), confirming the specificity of the assay.

RHAMM Antisera and Peptides Regulate Inflammatory Cell Chemotaxis

Since the expression of RHAMM was increased in the inflammatory cells adherent to the injured area of the carotid artery, the role of the RHAMM:HA interaction in neutrophil and macrophage chemotaxis was studied using both a peptide encoding one of the two HA-binding domains of RHAMM (aa$^{401-411}$), and rabbit anti-peptide aa$^{268-288}$ antiserum previously shown to interfere with HA-binding to RHAMM. Human neutrophil chemotaxis to IL-8 was significantly inhibited by peptide aa$^{401-411}$ (FIG. 52a), and both peptide aa$^{401-411}$ and anti-peptide aa$^{268-288}$ antiserum inhibited the chemotaxis of the two human macrophage cell lines, S1 and WEHI-3, to endotoxin-activated mouse serum (FIG. 52b). Heat-inactivated serum, used as a control, had no effect on neutrophil or macrophage chemotaxis (FIG. 52).

RHAMM:HA Interaction Regulates Smooth Muscle Cell Migration After Wounding Injury We investigated the effect of a peptide encoding one of the HA-binding domains of RHAMM (aa$^{401-411}$) on the ability of cells to respond to injury. This peptide significantly reduced the rate of translocation of smooth muscle cells into the denuded area following wounding of monolayers (FIG. 53). A scrambled peptide containing the same amino acids as peptide aa$^{401-411}$ had no effect on the wounding response (FIG. 53).

Example 10

Cell Cycle Analysis

For cell cycle analysis, cells of the ras-transformed fibroblast cell line C3 were harvested and fixed with 70% ethanol. The fixed cells were denatured by 2N HCl containing 0.5% Triton X-100 at RT for 30 min and then neutralized by treatment with 0.1 M Na$_2$B$_4$O$_7$, pH 8.5. Total DNA content was detected by propidium iodide staining. The stained cells were analyzed by flow cytometry using a Coulter Electronics Inc. EPICS 753 cell sorter and PARA1 cell cycle analysis software.

Growth Analysis

Cell density assay was carried out by seeding 5×10$^4$ cells in 60 mm dishes. Cells were cultured in DMEM supplemented with 10% FCS. At each point, cells were harvested by trypsinization and cell concentrations were determined by counting cells by trypan blue exclusion method.

Western Blot Analysis

For Western blot analysis, C3 cells in 100 mm dishes were washed 2× in PBS and then lysed in 0.25 ml ice cold buffer containing 50 mM β-glycerophosphate (pH 7.3), 1% Nonidet p-40, 10 mM NaF, 1% aprotinin and 1 mM Sodium Vanadate. The lysates were centrifused at 30,000 g for 20 min at 4° C. Protein concentration was determined by Biorad protein assay kit. Proteins were resolved on 10% SDS-polyacrylamide gels and transferred to nitrocellulose membranes in a Tris-Cl buffer containing 25 mM Tris, 192 mM Glycine and 20% (v/v) methanol, pH 8.3 at 100V for 1 hour at 4° C. Filters were incubated with antibody to p34$^{cdc2}$ (1:5000 dilution of polyclonal rabbits antiserum raised against the C-terminal peptide (LDNQIKKM) (SEQ ID NO:58) of Human p34$^{cdc7}$ protein) and developed with horseradish peroxidase-conjugated goat antibody to rabbit immunoglobulin G (sigma). Blotting was visualized by enhanced chomilumineacence Western blotting system (Amersham) following manufacturer's instruction.

RHAMM Treatment

RHAMM-II-GST fusion protein was prepared as described in Example 6.

Northern Blot Analysis

Total cellular RNA was extracted by a rapid RNA isolation method using Trizol reagent (GIBCO) as per manufacturer's instructions. For half-life measurements, transcription was inhibited by addition of 20 ug/ml actinomycin D. RNA was isolated at different times and analyzed for cdc2 gene expression. 20 ug of total cellular RNA was electrophoresed through 1% formamide-agarose gels and blotted onto Nytran membranes. The blots were prehybridized and probed with random primer 32p-labelled murine cdc2 cDNA (Paul Nurse). Loading of RNA was determined by probing with glyceraldehyde-3-phosphate dehyrogenase (GAPDH) cDNA. Autoradiography was done by Phosphoimager SF (Molecular Dynamics) using storage phosphor imaging.

Nuclear Run-on

Nuclear run-on assay was performed using 32P-labelled RNA to probe filter-bound cdc2 and GAPDH single strand cDNA inserts. Quantification of transcription was determined by scanning phosphor images using Multiquant software program (Molecular Dynamics).

Tumorigenicty and Experimental Metastasis Assay

C3 cells were serum starved, then cultured in presence of serum and GST or GST-HM for 48-hours and released from the substratum in Hanks. For assessing the tumorigenicity of the treated cells, 3×10$^5$ viable cells were injected subcutaneously into the right hind leg of syngeneic C3H/HeN Mice. The mice were maintained for 6–8 weeks after which tumors were removed, weighed and pieces processed for histology using conventional paraffin embedding techniques. For experimental metastasis assays, 4×10$^3$ treated cells were injected into the tail vein of syngeneic C3H/HeN mice. The mice were maintained for 16–18 days, euthanased and their lungs were stained by Boulin solution (picric acid, formaldehyde and acetic acid [15:5.:1]), removed and metastatic foci were counted under dissecting microscope.

As seen from FIG. 54A, when C3 cell cultures were treated with RHAMM, cells were arrested and accumulated in G2/M phase. The decrease in cell proliferation brought about by RHAMM treatment is seen clearly in FIG. 54B. RHAMM-treated C3 cells proceeded to cell death.

RHAMM treated cells showed dose dependent inhibition or p34$^{cdc2}$ expression, as seen in FIG. 55A. At 10 µg/ml, expression was greatly reduced.

The results shown in FIGS. 56A to D indicate that treatment of cells with RHAMM give degradation of cdc2 mRNA without alteration of transcription.

The tumorigenic and metastatic characteristics of RHAMM-treated ras-transformed C3 cells are set out in Table 5. Treatment of C3 cells with RHAMM prior to inoculation reduced the incidence of tumours in inoculated mice by 50%, and in the cases where RHAMM-treatod C3 cells did form tumours, latency was increased and ultimate tumour size was reduced compared to controls.

Pre-treatment with RHAMM also greatly reduced the metastatic capability of C3 cells.

The results shown in FIGS. 54 to 57 were from studies using RHAMM II. Similar results were seen with all soluble RHAMM proteins tested.

REFERENCES

Aruffo, A., Stamenkovic, I., Melnick, M., Underhill, C. B. and Seed, B. (1990) Cell, 61, 1303–1313.

Altschul S F, Gish W, Miller W, Myers E W, Lipman D J: Basic local alignment search tool. J Mol Biol 215:403–410, 1990.

Bae S-N, Arand G, Azzam H, Pavasant P, Torri J, Frandsen T L, Thompson E W: Molecular and celluar analysis of basement membrane invasion by human breast cells in Matrigel-based in vitro assay. Breast Cancer Res Treat 24:241–255, 1993

Bertrand, R. and Delpech, B. (1985). J. Neurochem., 45, 434–439.

Boudreaux, N., Turley, E. A. and Rabinovitch, M. (1991) Devel. Biol., 143, 235–247.

Branch, D R, Turner, A R and Guilbert, L J: Synergestic stimulation of macrophage proliferaton by the monokines factor-alpha and colony-stimulang factor-I. Blood 1989, 73:307–311

Brand, T., MacLellan, W. R., and Schneider, M. D. (1993). A dominant-negative receptor for type β transfoming growth factors created by deletion of the kinase domain. J. Biol. Chem., 268:11500–11503.

Burridge, K., Fath, K., Kelly, T., Nuckolls, G. and Turner, C. (1988). Focal adhesions: trans-membrane junctions between the extracellular matrix and the cytoskeleton Ann. Rev. Cell. Biol. 4:487–525.

Casscells, W: Migration of smooth muscle and endothelial cells: Critical events in restenosis. Cirulation 1992, 86: 723–729

Chirgwin J M, Przybyla A E, Maconald R J, Rutter W J: Isolation of biologically active ribonucleic acid from sources enriched in ribonuclease. Biochemistry 18:5294–5299, 1979.

Dalchau, R., Kirkley, J. and Fabre, J. W. (1980) Eur. J. Immunol., 10, 745–749.

de Wet, I. R, Fukushima, M., Dewji, N. N., Wilcox, E, O'Brien, S. md Helinski, D. R (1984). DNA, 3, 437–443.

Dickson R B, Lippman M E: Molecular determinants of growth, angiogenesis, and metastasts in breast cancer. Semin Oncol 19:286–298, 1992.

Douillard, T. Y. and Hoffman, T. (1983). Methods in Enzymology, 92, 168–174.

Egan, S. E., Wright, J. A, Jarolim, L., Yanagihara, K., Bassin R. H. and Greenberg, A. H. 1987. Transformation by oncogenes encoding protein kinases induces the metastatic phenotype. Science 238:202–205.

Evans, S. C., Lopez, L. C. and Shur, B. D. (1993). Dominant negative muation in cell surfce β1, 4-galactosyltransfcrase inhibits cell-cell and cell-matrix interactions. J. Cell Biol. 120:1045–1057.

Forsberg, N. and Gustafson, S., (1991) Biochem. Biophys. Acta., 1078, 12–18.

Gunning, P., Leavitt, J., Muscat, G., Ng, S. Y. and Kedes, L. (1987) A human β acton expression vector system directs high-level accumulation of antisense transcripts. Proc. Natl. Acad. Sci. USA 84:4831–4835.

Hardwick, C., Hoare, K., Owens, R., Hohn, H. P., Hook, M., Moore, D., Cripps, V., Austen, L., Nance, D. M. and Turley, E. A. (1992) J. Cell Biol., 117, 1343–1350.

Harris J R, Lippman M E, Veronesi U, Willett W: Breast cancer. New Eng J Med 327:319–328.

Hoare, K., Savini R. C., Wang, C., Yang, B. and Turley, E. A. (1993). Identification of hyaluronan binding proteins using a biotinyiated hyaluronan probe. Conn. Tis. Res. 30:117–126.

Huber, C., Houot, A-M., Corvol, P. ad Soubrier, F. (1991) J. Biol. Chem., 266, 15377–15383.

Iozzo, R. V. (1985) Lab. Invest., 53, 373–396.

Kashles, O., Yarden, Y., Fischer, R., Ullrich, A. and Schlessinger, J. (1991). A dominant negative mutation suppresses the function of normal epidermal growth factor receptors by hetero dimerization. Mol. Cell Biol. 11:1454–1463.

Khalil, N., Bereznay, O., Sporn, M. and Greenberg, A. H. (1989), J. Exp. Med., 170:727–737.

Kingston, R. E., Chomczynski and P., and Sacchi, N. (1993). Guanidinium method for total RNA preparation. Cur. Prop. Mol. Biol., (eds. Alsbel F. M; Brent, R., Kingston, R., Moore, D. D., Seidman, J. G., Smith, J. A. and Struhl, K.) John Wiley and Sons, N.Y. p.421–428.

Klewes, L., Turley, E. A. and Prehm, P. (1993). The hyaluronate synthase from a eukaryotic cell line. Biochem. J. 290:791–795.

Knudson W, Biswas C, Li X-Q, Nemec R E, Toole B P: The role and regulation of tumour associated hyaluronan. In Biology of Hyaluronan (Evered D, Whelan J eds), Ciba Foundation Symposium 143. Chichester: John Wiley and Sons, 1989, pp 150–169

Laemmli U K: Cleavage of structural proteins during assembly of the head of bacteriophage T4. Nature 227:680–685, 1970

Majack, R A and Clowes, A W: Inhibition of vascular smooth muscle cell migration by heparin-like glycosaminoglycans. J Cell Physiol 1984, 118: 253–256

Price J E: The biology of metastic breast cancer. Cancer 66:1313–1320, 1990

Rampyari, R. H., McGary, C. T. and Weigel, P. H. (1988) J. Biol. Chem., 263, 16661–16668.

Ripellino, J A, Killinger, M M, Margolis, R U and Margolis, R K: The hyaluronic acid binding region as a specific probe for the localization of hyaluronic acid in tissue sectons. J Hisotchem Cytochem 1985, 33: 1066–1086

Sambrook, J., Fritsch, E. F and Maniatis, T. (1989) Molecular Cloing:A Laboratory Manual, 2nd ed., Cold Spring Harbor Laboratory Press, Cold Spring Harbor, N.Y.

Samuel S. K., Hurta, R. A. R., Spearman, M. A., Wright, J. A., Turley, E. A. and Greenberg, A. H. (1993) J. Cell. Biol., 123, 749–758.

Shi Y, Kornovski, B S, Savani, R C and Turley, E A: A rapid multiwell colorometric assay for chemotaxis. J Immunol Methods 1993, 164: 149–154

Schol S L: Cell proliferation and migration on collagen substrata. In Vitro. J Cell Sci 41:159–175, 1980

Screaton, G. R., Bell, M. V., Jackson, D. G., Cornelis, F. B., Gerth, U. and Bell, J. I. (1992) Proc. Natl. Acad. Sci. USA, 89, 12160–12164.

Sommers C L, Thompson E W, Torri J A. Kemler R, Gelmann E P, Byas S W: Cell adhesion molecule uvolmorulin expression in human breast cancer cell lines: Relationship to morphology and invasive capacities. Cell Growth & Differention 2:365–372, 1991

Stamenkovic, I., Amiot, M., Pesando, J. M. and Seed, B. (1989) Cell, 56, 1057–1062.

Stamenkovic, I., Aruffo, A., Amiot, M. and Seed, B. (1991) EMBO J., 10, 343–348.

Stevenson, M M, Kongshovn, A L and Skamene, E: Genetic linkage of resistance to Listeria monocytogenes with macrophage inflammatory responses. J Immunol 1981, 127: 402

Thompson E W, Paik S, Brünner N, Sommers C L, Zugmaier G, Clarke R, Shima, T B, Torri J, Donahue S, Lippman M E, Martim R, Dickson R B: Association of increased basement membrane invasiveness with absence of oestrogen receptor and expression vimentin in human breast cancer cell lines. J Cell physiol 150:534–544, 1992

Toole, B. P., Goldberg, R. L., Chi-Rosso, G., Underhill, C. B. and Orkin, R. (1984) In. Role off Extacellular Matrix in Development. Treistad, editor. Alan R. Liss Inc., New York, 43–66.

Turley, E. A. (1984) Cancer Metastasis Rev., 3, 325–339.

Turley, E. A., Tretiak, M. and Tanguay, K. (1987). Effect of glycosaminoglycons and enzymes on the integrity of human placental amnion as a barrier to cell invasion. *J.N.C.I.* 78:787–795.

Turley, E. A., Austen, L., Vandeligt, K. and Clary, C. (1991) J. Cell. Biol., 112, 1041–1047.

Turley, E. A. (1992) Cancer Metastsis Rev., 11, 21–30.

Wang, X., O'Hanlon, T. P., Young, R. F. and Lay, J. T. Y. (1990) Glycobiology, 1, 25–31.

Wang C., Tammi M, Tammi R: Distribution of hyaluronan and its CD44 receptor in the epithelia of human skin appendages. Histochemistry 98:105–112, 1992

Woods, A. and Couchnan, J. R. (1988). Focal adhesions and cell matrix interactions. *Collagen Cell. Res.* 8:155–182.

Yang, B., Zhang, L. and Turley, E. A. (1993) J. Biol. Chem., 268, 8617–8623.

Yang, B., Yang, B., Savani, R. C. and Turley, E. A. (1994). Identification of a common hyaluronan binding motif in the hyaluronan proteins RHAMM, CD44 and link protein. *EMBO J.* 13:286–296.

TABLE 1

Identification of Exons and Introns
Nucleotide sequence of the exon-intronjunctions in the mouse RHAMM gene.

| Exon No/Size (bp) | cDNA Position of exons in RHAMM I | Intron No. | Donor | Acceptor | Intron Size (kb) | Method |
|---|---|---|---|---|---|---|
| 1A(116) | −140−−24 | 1 | GA/tactta | tgatgt/GG | 1.60 | sequencing |
| 1B(124) | −64−−60 | 2 | GG/gtgagt | gtgcag/AG | 0.09 | sequencing |
| 2(101) | 61–161 | 3 | CT/catgtg | atacag/CT | 6.50 | PCR |
| 3(176) | 162–337 | 4 | AG/gtactg | ttacag/AC | 0.38 | sequencing |
| 4(149) | 338–486 | 5 | AG/gtagct | atgcag/GA | 0.52 | sequencing |
| 5(216) | 487–701 | 6 | GA/gtttgt | ctttag/GA | 0.80 | PCR |
| 6(368) | 702–1070 | 7 | AG/gtatt | tataag/CT | 1.80 | PCR |
| 7(147) | 1071–1217 | 8 | AG/gtgagt | ctaagg/GA | 0.29 | sequencing |
| 8(153) | 1218–1370 | 9 | AG/gtaagt | atacag/AA | 0.12 | sequencing |
| 9(97) | 1371–1470 | 10 | AG/gtttgt | ttccag/CA | 1.30 | PCR |
| 10(179) | 1471–1647 | 11 | CG/gtttgt | tcacag/GA | 2.20 | PCR |
| 11(152) | 1648–1801 | 12 | AG/gtaaaa | cttcag/GC | 0.90 | PCR |
| 12(1099) | 1802–2904 | | | | | |

Consensus splice sites: Donor: AG/gtat/gt; Acceptor: ttacag
Minus one (−1) in the cDNA position indicates the first nucleotide before the initiation methionine of RHAMM I

TABLE 2

CHARACTERISTICS OF RHAMM TRANSFECTED 10T½ CLONES.

| Cell Line | Densitometry of RHAMM Western Analysis | FACS* Mean Fluorescent Intensity | Rate of Motility ($\mu$M/hr ± SEM) Control | Rate of Motility ($\mu$M/hr ± SEM) Anti-RHAMM Antibody | Nuclear Foci/Dish | Overlap Ratio |
|---|---|---|---|---|---|---|
| a) 10T½ fibroblast | 0.31 | 2.4 | 10.0 ± 0.85 | 8.6 ± 1.2 | 0 | 0.01 |
| C3 fibrosarcoma | 1.35 | 85.0 | 35.1 ± 2.2 | 10.2 ± 1.4 | >60 | 0.45 |
| b) Genomic RHAMM Transfectants | | | | | | |
| Vector | 0.54 | 2.5 | 10.6 ± 0.9 | 9.9 ± 0.4 | 0 | 0.02 |
| G2 | 1.29 | 82.5 | 36.6 ± 4.4 | N.D. | >60 | 0.36 |
| G6 | 2.20 | 43.0 | 31.8 ± 2.0 | N.D. | 45 | 0.25 |
| G10 | 1.08 | 74.8 | 25.6 ± 1.7 | 10.9 ± 1.7 | >60 | 0.49 |
| G12 | 2.77 | 116.0 | 36.1 ± 2.2 | 11.7 ± 0.5 | >60 | 0.42 |
| c) RHAMM I-2A cDNA Transfectants | | | | | | |
| Vector | 0.35 | 3.9 | 9.8 ± 0.5 | 9.8 | 0 | 0.01 |
| I-2A-5 | 2.65 | 74.8 | 24.5 ± 2.3 | 10.1 ± 2.1 | >60 | 0.41 |
| MR10T½-4 | 1.56 | 81.3 | 11.1 ± 0.6 | 9.3 ± 1.2 | 0 | 0.01 |

TABLE 2-continued

CHARACTERISTICS OF RHAMM TRANSFECTED 10T½ CLONES.

| Cell Line | Densitometry of RHAMM Western Analysis | FACS* Mean Fluorescent Intensity | Rate of Motility ($\mu$M/hr ± SEM) Control | Anti-RHAMM Antibody | Nuclear Foci/Dish | Overlap Ratio |
|---|---|---|---|---|---|---|

*Corrected for background fluorescence in the presence of normal IgG$_1$; ND: Not determined; 10T½ cells were transfected with either genomic RHAMM (intron 2 - exon 12) for clones G2, G6, G10 and G12, RHAMM cDNA (RHAMM I-2A, Entwistle et al, 1994) for clone I-2A-5 or RHAMM cDNA mutated in its HA binding domains clone MR10T½-4 as outlined in FIG. 4a. Characteristics were determined as outlined in methods. Motility rate was obtained by tracking 100 cells.

TABLE 3

TUMORIGENIC PROPERTIES OF RHAMM TRANSFECTED CELLS

| Cell Line* | Number of Colonies/Plate** | Subcutaneous Tumors |
|---|---|---|
| 10T½-Vector Control | 13 ± 4 | 0/4 |
| G6 | ND | 4/4 |
| G10 | 150 ± 7 | 4/4 |
| G12 | 249 ± 16 | 4/4 |
| I-2a-5 | ND | 4/4 |
| MR10T½-4 | ND | 0/4 |
| C3 fibrosarcoma | 77 ± 9 | 4/4 |

*Cell lines described in Table 1.
**The values represent the mean of triplicate samples ± S.E.M.

TABLE 4

SUPPRESSION OF TRANSFORMATION BY EXPRESSION OF RHAMM MUTATED IN ITS HA BINDING DOMAIN

| Cell Line* | Growth in Soft Agar Colonies ± S.E. | Nuclear Overlap Ratio | Nuclear Overlap Foci/Dish | Rate of Motility $\mu$M/hr ± S.E. |
|---|---|---|---|---|
| 10T½ | 0 | 0.01 | 0 | 9.5 ± 1.3 |
| C3-Vector Control | 77 ± 9 | 0.47 | >60 | 27.5 ± 1.2 |
| MRC3-4D | 0 | 0.005 | 0 | 3.5 ± 0.8 |
| MRC3-5B | 1 ± 1 | 0.004 | 0 | 1.8 ± 0.5 |
| MRC3-5C | 0 | 0.005 | 0 | 2.0 ± 0.6 |

*The H-ras transformed C3 fibrosarcoma was transfected either with empty vector (C3-vector control) or with RHAMM II (Entwistle et al., 1994) mutated in its HA-binding domain (MRC3-4D, MRC3-5B, MRC3-5 while 10T½ is the non transformed parental line of the C3.

TABLE 5

Tumorigenic and Metastatic Characteristics of RHAMM-Treated C3 Cells in Syngeneic C3H/HeN Mice

| Treatment | Tumorigenicity[a] Frequency | Latency (Days) | Tumor size (cm$^2$) Day 25 | Expt. Metastases[b] Frequency | No. |
|---|---|---|---|---|---|
| Control | 4/4 | 5 | 166 ± 16 | 4/4 | >300 |
| GST | 4/4 | 5 | 198 ± 39 | 4/4 | >300 |
| GST-RHAMM | 2/4 | 22 | 90 ± 0.7 | 3/4 | <10 |

[a]Results are reported for subcutaneous injection of 3 × 10$^5$ cells.
[b]Data were obtained after i.v. injection of 4 × 10$^5$ cells.

We claim:

1. An isolated protein comprising the amino acid sequence of FIG. 2 (Sequence ID NO:2).

2. The protein of claim 1 further comprising the amino acid sequence V S I E K E K I D E K C E T E K L L E Y I Q E I S (SEQ ID No:4) inserted between amino acid 54 and amino acid 55 of FIG. 2 (SEQ ID No:11).

3. A peptide having the amino acid sequence V S I E K E K I D E K C E T E K L L E Y I Q E I S (SEQ ID NO:4).

* * * * *